(12) United States Patent
Kawanishi

(10) Patent No.: US 8,021,819 B2
(45) Date of Patent: *Sep. 20, 2011

(54) SULFONIUM COMPOUND, PHOTOSENSITIVE COMPOSITION CONTAINING THE COMPOUND AND PATTERN-FORMING METHOD USING THE PHOTOSENSITIVE COMPOSITION

(75) Inventor: Yasutomo Kawanishi, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 63 days.

This patent is subject to a terminal disclaimer.

(21) Appl. No.: 11/703,100

(22) Filed: Feb. 7, 2007

(65) Prior Publication Data

US 2007/0184384 A1  Aug. 9, 2007

(30) Foreign Application Priority Data

Feb. 7, 2006  (JP) ............................... P2006-029870

(51) Int. Cl.
- G03C 1/00 (2006.01)
- G03F 1/00 (2006.01)
- G03F 7/00 (2006.01)
- C07D 343/00 (2006.01)
- C07D 335/08 (2006.01)

(52) U.S. Cl. ............ 430/270.1; 430/322; 430/325; 430/326; 430/922; 549/16; 549/26

(58) Field of Classification Search .............. 430/270.1; 526/222; 528/90; 546/202; 549/15, 17, 549/29, 41, 43, 16, 26
See application file for complete search history.

(56) References Cited

U.S. PATENT DOCUMENTS

| | | | |
|---|---|---|---|
| 5,731,364 A * | 3/1998 | Sinta et al. ................ | 522/31 |
| 6,548,221 B2 | 4/2003 | Uetani et al. | |
| 6,680,157 B1 | 1/2004 | Fedynyshyn | |
| 7,344,821 B2 * | 3/2008 | Mizutani ................. | 430/270.1 |
| 7,405,308 B2 * | 7/2008 | Crivello .................... | 549/17 |
| 7,615,330 B2 * | 11/2009 | Kamimura et al. ...... | 430/270.1 |
| 7,718,344 B2 * | 5/2010 | Kamimura et al. ...... | 430/270.1 |
| 7,851,130 B2 * | 12/2010 | Kawanishi et al. ...... | 430/270.1 |
| 2004/0265733 A1 * | 12/2004 | Houlihan et al. ........ | 430/270.1 |
| 2005/0064333 A1 | 3/2005 | Crivello | |
| 2005/0079441 A1 | 4/2005 | Takahashi | |
| 2005/0176969 A1 * | 8/2005 | Herlihy et al. .......... | 549/3 |
| 2005/0209365 A1 * | 9/2005 | Ookubo et al. .......... | 523/160 |
| 2006/0194147 A1 | 8/2006 | Kawanishi | |

FOREIGN PATENT DOCUMENTS

| | | |
|---|---|---|
| EP | 1-480-078 A1 | 11/2004 |
| EP | 1 693 705 A2 | 8/2006 |
| JP | 06-199770 A | 7/1994 |
| JP | 2002-148788 A | 5/2002 |
| JP | 2005-501040 A | 1/2005 |
| JP | 2005-115016 A | 4/2005 |
| JP | 2005-263897 A | 9/2005 |
| JP | 2006-328297 A | 12/2006 |
| JP | 2007-094356 A | 4/2007 |
| JP | 2003-121999 A | 4/2011 |
| WO | 03/008404 A2 | 1/2003 |
| WO | WO 03/008404 A2 | 1/2003 |
| WO | WO 03008404 A2 * | 1/2003 |

OTHER PUBLICATIONS

European Search Report dated Apr. 17, 2007.
Japanese Patent Office, Office Action, dated Mar. 15, 2011, issued in Application No. 2006-029870.

* cited by examiner

*Primary Examiner* — Cynthia Kelly
*Assistant Examiner* — Connie P Johnson
(74) *Attorney, Agent, or Firm* — Sughrue Mion, PLLC

(57) ABSTRACT

A photosensitive composition, which comprises a compound represented by formula (I):

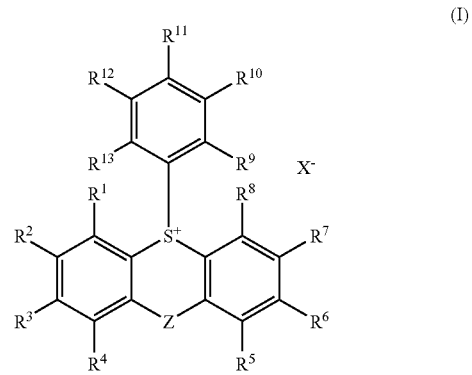

wherein $R^1$ to $R^{13}$ each independently represents a hydrogen atom or a substituent, and at least one of $R^1$ to $R^{13}$ is a substituent containing an alcoholic hydroxyl group; Z represents a single bond or a divalent linking group; and $X^-$ represents a counter anion; and a pattern-forming method using the photosensitive composition.

20 Claims, 1 Drawing Sheet

SULFONIUM COMPOUND, PHOTOSENSITIVE COMPOSITION CONTAINING THE COMPOUND AND PATTERN-FORMING METHOD USING THE PHOTOSENSITIVE COMPOSITION

This is a non-provisional application claiming priority from Japanese patent application No. P2006-029870 filed on Feb. 7, 2006, which is incorporated herein by reference.

BACKGROUND OF THE INVENTION

1. Field of the Invention

The present invention relates to a photosensitive composition capable of changing the property by reaction upon irradiation with actinic ray or radiation (X-ray, electron beam, EUV, etc.), a compound for use in the photosensitive composition, and a pattern-forming method using the photosensitive composition. More specifically, the invention relates to a photosensitive composition for use in a manufacturing process of semiconductors, e.g., IC, the manufacture of circuit substrates for liquid crystals, thermal heads and the like, other photo-fabrication processes, lithographic printing plates, and acid-curable compositions, and also the invention relates to a compound for use in the photosensitive composition, and a pattern-forming method using the photosensitive composition.

2. Description of the Related Art

Chemical amplification resist compositions are pattern-forming materials capable of generating an acid at the area irradiated with radiation such as a far ultraviolet ray, changing the solubility in a developer of the area irradiated with the actinic radiation and the non-irradiated area by the reaction with the acid as a catalyst, and forming a pattern on a substrate.

When a KrF excimer laser is used as the exposure light source, since resins having poly(hydroxystyrene) that is small in absorption in the region of 248 nm as a fundamental skeleton are mainly used, the compositions are high sensitivity, high resolution and good patterns can be formed as compared with conventionally used naphthoquinonediazide/novolak resins.

On the other hand, when a light source of further shorter wavelength, e.g., an ArF excimer laser (193 nm), is used as the exposure light source, since compounds containing an aromatic group substantially show large absorption in the region of 193 nm, even the chemical amplification resist compositions are not sufficient.

To cope with this problem, resists for an ArF excimer laser containing a resin having an alicyclic hydrocarbon structure have been developed.

Regarding an acid generator that is the main constituent of chemical amplification resists, triphenylsulfonium salts are generally known (e.g., refer to U.S. Pat. No. 6,548,221).

However, these acid generators are still insufficient in various points, so that photosensitive compositions that are improved in sensitivity, resolution, a pattern form, and roughness are desired.

Further, when light sources such as electron beams, X-rays and EUV are used, exposure is carried out under vacuum, so that compounds having a low boiling point such as solvents and resist materials decomposed by high energy are volatilized to thereby contaminate the exposure apparatus, i.e., outgassing is a serious problem. In recent years, various investigations are in progress on the reduction of outgassing, and a variety of trials are suggested, e.g., restraint of volatilization of low molecular weight compounds by forming a top coat layer (e.g., refer to EP 1480078), and addition of a radical trapping agent capable of inhibiting decomposition of a polymer (e.g., refer to U.S. Pat. No. 6,680,157). Some contrivances of outgassing are also required in connection with acid generators.

SUMMARY OF THE INVENTION

Accordingly, an object of the present invention is to provide a photosensitive composition excellent in sensitivity, resolution, roughness, a pattern shape, and outgassing characteristics, another object is to provide a compound for use in the photosensitive composition, and a further object is to provide a pattern-forming method using the photosensitive composition.

The above objects of the invention can be solved according to the following constitutions by a novel sulfonium compound represented by formula (I).

(1) A photosensitive composition, which comprises a compound (A) represented by formula (I):

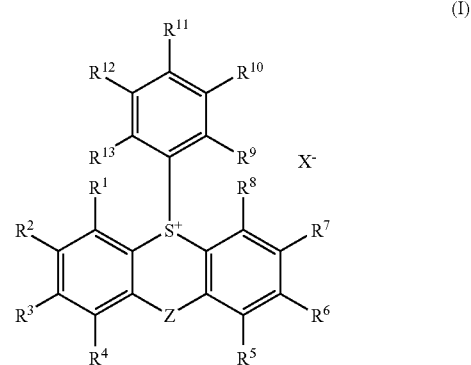

wherein $R^1$ to $R^{13}$ each independently represents a hydrogen atom or a substituent, and at least one of $R^1$ to $R^{13}$ is a substituent containing an alcoholic hydroxyl group;

Z represents a single bond or a divalent linking group; and $X^-$ represents a counter anion.

(2) The photosensitive composition as described in (1) above, which further comprises a resin (B) capable of decomposing by an action of an acid to increase solubility in an alkali developing solution.

(3) The photosensitive composition as described in (1) or (2) above, which further comprises:

a resin (C) soluble in an alkali developing solution; and an acid crosslinking agent (D) capable of crosslinking with the resin soluble in an alkali developing solution by an action of an acid.

(4) The photosensitive composition as described in any of (1) to (3) above, which is exposed with X-ray, electron beam or EUV.

Further, the preferred exemplary embodiments of the invention are described below.

(5) The positive photosensitive composition as described in (2) above, wherein the resin (B) contains a hydroxystyrene structural unit.

(6) The positive photosensitive composition as described in (2) above, wherein the resin (B) contains a repeating unit having a monocyclic or polycyclic hydrocarbon structure.

(7) The positive photosensitive composition as described in (2) above,
wherein the resin (B) contains a repeating unit having an alcoholic hydroxyl group.

(8) The positive photosensitive composition as described in (7) above,
wherein the repeating unit having an alcoholic hydroxyl group of the resin (B) is a repeating unit containing at least one structure selected from a monohydroxyadamantane structure, a dihydroxyadamantane structure and a trihydroxyadamantane structure.

(9) The positive photosensitive composition as described in (2) above,
wherein the resin (B) is a resin containing a repeating unit having a lactone structure.

(10) The positive photosensitive composition as described in (2) above,
wherein the resin (B) is a resin containing at least one methacrylate repeating unit and at least one acrylate repeating unit.

(11) The positive photosensitive composition as described in (2) above,
wherein the resin (B) has a fluorine atom on a main chain or side chain.

(12) The positive photosensitive composition as described in (2) above,
wherein the resin (B) has a hexafluoro-2-propanol structure.

(13) The positive photosensitive composition as described in any of (5) to (12) above, which further comprises a dissolution inhibiting compound (E) capable of decomposing by an action of an acid to increase solubility in an alkali developing solution and having a molecular weight of 3,000 or less.

(14) The positive photosensitive composition as described in any of (5) to (13) above, which further comprises at least one of a basic compound (F) and a fluorine and/or silicon surfactant (G).

(15) The positive photosensitive composition as described in (5) above,
wherein the resin (B) contains at least one repeating unit selected from 2-alkyl-2-adamantyl(meth)acrylate and dialkyl (1-adamantyl)methyl(meth)-acrylate, at least one repeating unit having a lactone structure and at least one repeating unit having 2 or more hydroxyl groups.

(16) The photosensitive composition as described in (15) above,
wherein the resin (B) further contains a repeating unit having a carboxyl group.

(17) The photosensitive composition as described in (5) above,
wherein the resin (B) contains at least one repeating unit selected from 2-alkyl-2-adamantyl(meth)acrylate and dialkyl (1-adamantyl)methyl(meth)acrylate and at least one repeating unit having a hydroxystyrene structure.

(18) A pattern-forming method, which comprises:
forming a photosensitive film with a photosensitive composition as described in any of (1) to (17) above; and
exposing and developing the photosensitive film.

DETAILED DESCRIPTION OF THE INVENTION

Figure 1:
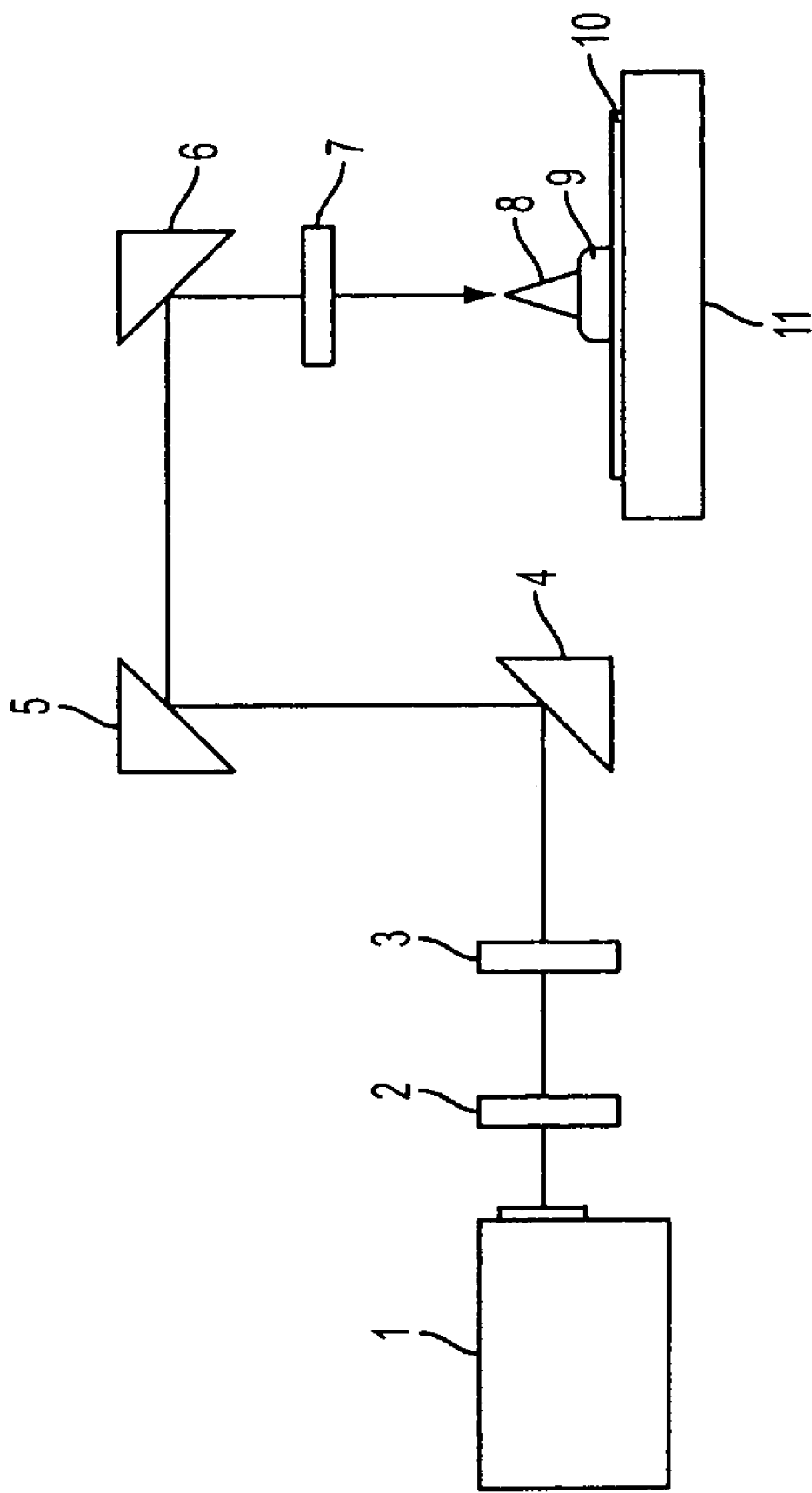
FIG. 1 is a schematic drawing of a laboratory apparatus of two-beam interference exposure,
wherein 1 denotes laser; 2 denotes diaphragm; 3 denotes shutter; 4, 5 and 6 denote reflection mirrors; 7 denotes condenser lens; 8 denotes prism; 9 denotes immersion liquid; 10 denotes wafer having an antireflection film and a resist film; and 11 denotes wafer stage.

The invention is described in detail below.
In the description of a group (an atomic group) in the specification of the invention, the description not referring to substitution or unsubstitution includes both a group not having a substituent and a group having a substituent. For example, "an alkyl group" includes not only an alkyl group having no substituent (an unsubstituted alkyl group) but also an alkyl group having a substituent (a substituted alkyl group).

The present invention is based on the finding of a novel compound represented by formula (I) capable of generating an acid (hereinafter also referred to as "acid generator A1") upon irradiation with actinic ray or radiation that is useful for a photosensitive composition.

A photosensitive composition containing acid generator A1 may be either a positive or negative photosensitive composition.

A positive photosensitive composition in the invention, preferably a positive resist composition, contains acid generator (A), and resin (B) capable of decomposing by the action of an acid to increase solubility in an alkali developing solution, and if necessary, dissolution inhibiting compound (E) capable of decomposing by the action of an acid to increase solubility in an alkali developing solution having a molecular weight of 3,000 or less.

A negative photosensitive composition in the invention, preferably a negative resist composition, contains acid generator (A), resin (C) soluble in an alkali developing solution, and acid crosslinking agent (D) capable of crosslinking with the resin soluble in an alkali developing solution by the action of an acid.

[1] Compound Represented by Formula (I) (Acid Generator A1):

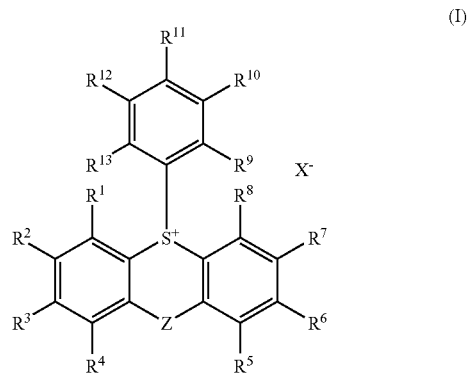

In formula (I), $R^1$ to $R^{13}$ each independently represents a hydrogen atom or a substituent, and at least one of $R^1$ to $R^{13}$ is a substituent containing an alcoholic hydroxyl group.
Z represents a single bond or a divalent linking group.
$X^-$ represents a counter anion.
The alcoholic hydroxyl group in the invention means a hydroxyl group bonding to the carbon atom of an alkyl group.
When $R^1$ to $R^{13}$ each independently represents a substituent containing an alcoholic hydroxyl group, each of $R^1$ to $R^{13}$ is represented by —W—Y, where Y is an alkyl group substituted with a hydroxyl group, and W is a single bond or a divalent linking group.

As the alkyl group represented by Y, a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclopentyl group, a cyclohexyl group, an adamantyl group, a norbornyl group, and a boronyl group can be exemplified, preferably an ethyl group, a propyl group, an isopropyl group, an n-butyl group, an isobutyl group, and a sec-butyl group, and more preferably an ethyl group, a propyl group, and an isopropyl group. Y especially preferably has a structure of —$CH_2CH_2OH$.

The divalent linking group represented by W is not especially restricted, and, for example, divalent groups obtained by substituting an arbitrary hydrogen atom of a monovalent group with a single bond can be exemplified, and as such monovalent groups, e.g., an alkoxyl group, an acyloxy group, a carbamoyloxy group, an alkoxycarbonyloxy group, an aryloxycarbonyloxy group, an acylamino group, an amino-carbonylamino group, an alkoxycarbonylamino group, an aryloxycarbonylamino group, a sulfamoylamino group, an alkylsulfonylamino group, an arylsulfonylamino group, an alkylthio group, an arylthio group, a sulfamoyl group, an alkylsulfinyl group, an arylsulfinyl group, an alkylsulfonyl group, an arylsulfonyl group, an acyl group, an aryloxycarbonyl group, an alkoxycarbonyl group, and a carbamoyl group can be exemplified.

W preferably represents a single bond, or a divalent group obtained by substituting an arbitrary hydrogen atom of an alkoxyl group, an acyloxy group, an acyamino group, an alkylsulfonylamino group, an arylsulfonylamino group, an alkylthio group, an alkylsulfonyl group, an acyl group, an alkoxycarbonyl group, or a carbamoyl group with a single bond, and more preferably a single bond, or a divalent group obtained by substituting an arbitrary hydrogen atom of an acyloxy group, an alkylsulfonyl group, an acyl group, or an alkoxycarbonyl group with a single bond.

When $R^1$ to $R^{13}$ each independently represents a substituent containing an alcoholic hydroxyl group, the number of carbon atoms contained in the substituent is preferably from 2 to 10, more preferably from 2 to 6, and especially preferably from 2 to 4.

The substituent containing an alcoholic hydroxyl group represented by $R^1$ to $R^{13}$ may have two or more alcoholic hydroxyl groups. The number of the alcoholic hydroxyl groups of the substituent containing an alcoholic hydroxyl group represented by $R^1$ to $R^{13}$ is from 1 to 6, preferably from 1 to 3, and more preferably 1.

The number of alcoholic hydroxyl groups of the compound represented by formula (I) is from 1 to 10 in total of $R^1$ to $R^{13}$, preferably from 1 to 6, and more preferably from 1 to 3.

When each of $R^1$ to $R^{13}$ does not contain an alcoholic hydroxyl group, $R^1$ to $R^{13}$ each independently represents a hydrogen atom or a substituent, and any substituent may be used with no particular restriction, e.g., a halogen atom, an alkyl group (including a cycloalkyl group, a bicycloalkyl group, a tricycloalkyl group), an alkenyl group (including a cycloalkenyl group, a bicycloalkenyl group), an alkynyl group, an aryl group, a heterocyclic group, a cyano group, a nitro group, a carboxyl group, an alkoxyl group, an aryloxy group, a silyloxy group, a heterocyclic oxy group, an acyloxy group, a carbamoyloxy group, an alkoxycarbonyloxy group, an aryloxycarbonyloxy group, an amino group (including an anilino group), an ammonio group, an acylamino group, an aminocarbonylamino group, an alkoxycarbonylamino group, an aryloxycarbonylamino group, a sulfamoylamino group, an alkyl-and arylsulfonylamino group, a mercapto group, an alkylthio group, an arylthio group, a heterocyclic thio group, a sulfamoyl group, a sulfo group, an alkyl-and arylsulfinyl group, an alkyl-and arylsulfonyl group, an acyl group, an aryloxycarbonyl group, an alkoxy-carbonyl group, a carbamoyl group, an aryl-and heterocyclic azo group, an imido group, a phosphino group, a phosphinyl group, a phosphinyloxy group, a phosphinylamino group, a phosphono group, a silyl group, a hydrazino group, a ureido group, a boronic acid group (—$B(OH)_2$), a phosphato group (—$OPO(OH)_2$), a sulfato group (—$OSO_3H$), and other known substituents are exemplified as the substituents.

Further, contiguous two of $R^1$ to $R^{13}$ can also form a ring together (e.g., hydrocarbon rings of aromatic groups or non-aromatic groups, heterocyclic rings, and polycyclic condensed rings can be formed by combination of these rings, e.g., a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a quinolizine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthene ring, a phenoxthine ring, a phenothiazine ring, and a phenazine ring are exemplified).

When each of $R^1$ to $R^{13}$ does not contain an alcoholic hydroxyl group, $R^1$ to $R^{13}$ each preferably represents a hydrogen atom, a halogen atom, an alkyl group (including a cycloalkyl group, a bicycloalkyl group and a tricycloalkyl group), an alkenyl group (including a cycloalkenyl group and a bicycloalkenyl group), an alkynyl group, an aryl group, a cyano group, a carboxyl group, an alkoxyl group, an aryloxy group, an acyloxy group, a carbamoyloxy group, an acylamino group, an aminocarbonylamino group, an alkoxycarbonylamino group, an aryloxycarbonylamino group, a sulfamoylamino group, an alkyl-or arylsulfonylamino group, an alkylthio group, an arylthio group, a sulfamoyl group, an alkyl-or arylsulfonyl group, an aryloxycarbonyl group, an alkoxycarbonyl group, a carbamoyl group, an imido group, a silyl group, or a ureido group.

When each of $R^1$ to $R^{13}$ does not contain an alcoholic hydroxyl group, $R^1$ to $R^{13}$ each more preferably represents a hydrogen atom, a halogen atom, an alkyl group (including a cycloalkyl group, a bicycloalkyl group, and a tricycloalkyl group), a cyano group, an alkoxyl group, an acyloxy group, an acylamino group, an aminocarbonylamino group, an alkoxycarbonylamino group, an alkyl-or arylsulfonylamino group, an alkylthio group, a sulfamoyl group, an alkyl-or arylsulfonyl group, an alkoxycarbonyl group, or a carbamoyl group.

Further, when each of $R^1$ to $R^{13}$ does not contain an alcoholic hydroxyl group, $R^1$ to $R^{13}$ each especially preferably represents a hydrogen atom, an alkyl group (including a cycloalkyl group, a bicycloalkyl group, and a tricycloalkyl group), a halogen atom, or an alkoxyl group.

In formula (I), at least one of $R^1$ to $R^{13}$ contains an alcoholic hydroxyl group, and preferably at least one of $R^9$ to $R^{13}$ contains an alcoholic hydroxyl group.

Z represents a single bond or a divalent linking group, and as the divalent linking group, e.g., an alkylene group, an arylene group, a carbonyl group, a sulfonyl group, a carbonyloxy group, a carbonylamino group, a sulfonamido group, an ether group, a thioether group, an amino group, a disulfide group, an acyl group, an alkylsulfonyl group, —CH=CH—, —C≡C—, an aminocarbonylamino group, and an aminosulfonylamino group are exemplified, which groups may have a substituent. As the substituents of these groups, the substituents as described in $R^1$ to $R^{13}$ are exemplified. Z preferably represents a single bond, or a group not having an electron attractive property, e.g., an alkylene group, an arylene group, an ether group, a thioether group, an amino group, —CH=CH—, —C≡C—, an aminocarbonylamino group, or an aminosulfonylamino group, more preferably a single bond, an ether group, or a thioether group, and especially preferably a single bond.

The compound represented by formula (I) has a counter anion $X^{-1}$. As the anion, an organic anion is preferred. The organic anion is an anion containing at least one carbon atom. Further, the organic anion is preferably a non-nucleophilic anion. A non-nucleophilic anion is an anion having extremely low ability of causing a nucleophilic reaction and capable of restraining the aging decomposition due to an intramolecular nucleophilic reaction.

As the non-nucleophilic anions, e.g., a sulfonate anion, a carboxylate anion, a sulfonylimide anion, a bis(alkyl-sulfonyl)imide anion, and a tris(alkylsulfonyl)methyl anion can be exemplified.

As the non-nucleophilic sulfonate anions, e.g., an alkylsulfonate anion, an arylsulfonate anion, and a camphorsulfonate anion are exemplified. As the non-nucleophilic carboxylate anions, e.g., an alkylcarboxylate anion, an arylcarboxylate anion and an aralkylcarboxylate anion are exemplified.

The alkyl moiety in the alkylsulfonate anion may be an alkyl group or a cycloalkyl group, preferably an alkyl group having from 1 to 30 carbon atoms and a cycloalkyl group having from 3 to 30 carbon atoms, e.g., a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclopentyl group, a cyclohexyl group, an adamantyl group, a norbornyl group, and a boronyl group can be exemplified.

The aryl group in the arylsulfonate anion is preferably an aryl group having from 6 to 14 carbon atoms, e.g., a phenyl group, a tolyl group, and a naphthyl group can be exemplified.

As the substituents of the alkyl group, cycloalkyl group and aryl group of the alkylsulfonate anion and arylsulfonate anion, e.g., a nitro group, a halogen atom (a fluorine atom, a chlorine atom, a bromine atom, and an iodine atom), a carboxyl group, a hydroxyl group, an amino group, a cyano group, an alkoxyl group (preferably having from 1 to 15 carbon atoms), a cycloalkyl group (preferably having from 3 to 15 carbon atoms), an aryl group (preferably having from 6 to 14 carbon atoms), an alkoxycarbonyl group (preferably having from 2 to 7 carbon atoms), an acyl group (preferably having from 2 to 12 carbon atoms), and an alkoxycarbonyloxy group (preferably having from 2 to 7 carbon atoms) can be exemplified. As for the aryl group and cyclic structure of each group, an alkyl group (preferably having from 1 to 15 carbon atoms) can further be exemplified as the substituent.

As the alkyl moiety in the alkylcarboxylate anion, the same alkyl groups and cycloalkyl groups as in the alkyl-sulfonate anion can be exemplified. As the aryl group in the arylcarboxylate anion, the same aryl groups as in the arylsulfonate anion can be exemplified. As the aralkyl group in the aralkylcarboxylate anion, preferably an aralkyl group having from 6 to 12 carbon atoms, e.g., a benzyl group, a phenethyl group, a naphthylmethyl group, a naphthylethyl group, and a naphthylmethyl group can be exemplified.

As the substituents of the alkyl group, cycloalkyl group, aryl group and aralkyl group in the alkylcarboxylate anion, arylcarboxylate anion and aralkylcarboxylate anion, e.g., the same halogen atoms, alkyl groups, cycloalkyl groups, alkoxyl groups and alkylthio groups as in the arylsulfonate anion can be exemplified. As the sulfonylimide anion, e.g., a saccharin anion can be exemplified.

The alkyl group in the bis(alkylsulfonyl)imide anion and tris(alkylsulfonyl)methyl anion is preferably an alkyl group having from 1 to 5 carbon atoms, e.g., a methyl group, an ethyl group, a propyl group, an isopropyl group, an n-butyl group, an isobutyl group, a sec-butyl group, a pentyl group and a neopentyl group are exemplified. As the substituents on these alkyl groups, e.g., a halogen atom, an alkyl group substituted with a halogen atom, an alkoxyl group, and an alkylthio group can be exemplified.

As other non-nucleophilic anions, e.g., fluorinated phosphorus, fluorinated boron and fluorinated antimony can be exemplified.

As the counter anion $X^-$ of the compound represented by formula (I), a sulfonate anion is preferred, and an aryl-sulfonate anion is more preferred.

As counter anions, specifically a methanesulfonate anion, a trifluoromethanesulfonate anion, a pentafluoroethanesulfonate anion, a heptafluoropropanesulfonate anion, a perfluorobutanesulfonate anion, a perfluorohexanesulfonate anion, a perfluorooctanesulfonate anion, a pentafluorobenzenesulfonate anion, a 3,5-bistrifluoromethylbenzenesulfonate anion, a 2,4,6-triisopropylbenzenesulfonate anion, a perfluoroethoxyethanesulfonate anion, a 2,3,5,6-tetra-fluoro-4-dodecyloxybenzenesulfonate anion, a p-toluenesulfonate anion, and a 2,4,6-trimethylbenzenesulfonate anion are exemplified.

The addition amount of the compound represented by formula (I) is preferably from 0.1 to 20 mass % as the total amount on the basis of all the solids content of the photosensitive composition, more preferably from 0.5 to 10 mass %, and still more preferably from 3 to 8 mass %. (In this specification, mass ratio is equal to weight ratio.)

The molecular weight of the compound represented by formula (I) is preferably from 200 to 2,000, and especially preferably from 400 to 1,000.

The compound represented by formula (I) can be synthesized according to the method of condensation reaction of a benzene derivative containing a hydroxyl group protected with a protective group in the substituent and a cyclic sulfoxide compound to form a sulfonium salt, and deprotecting the protective group of the hydroxyl group.

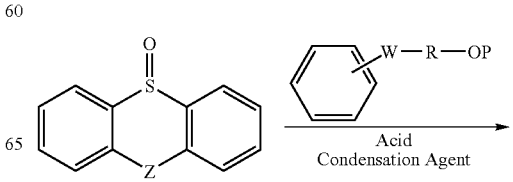

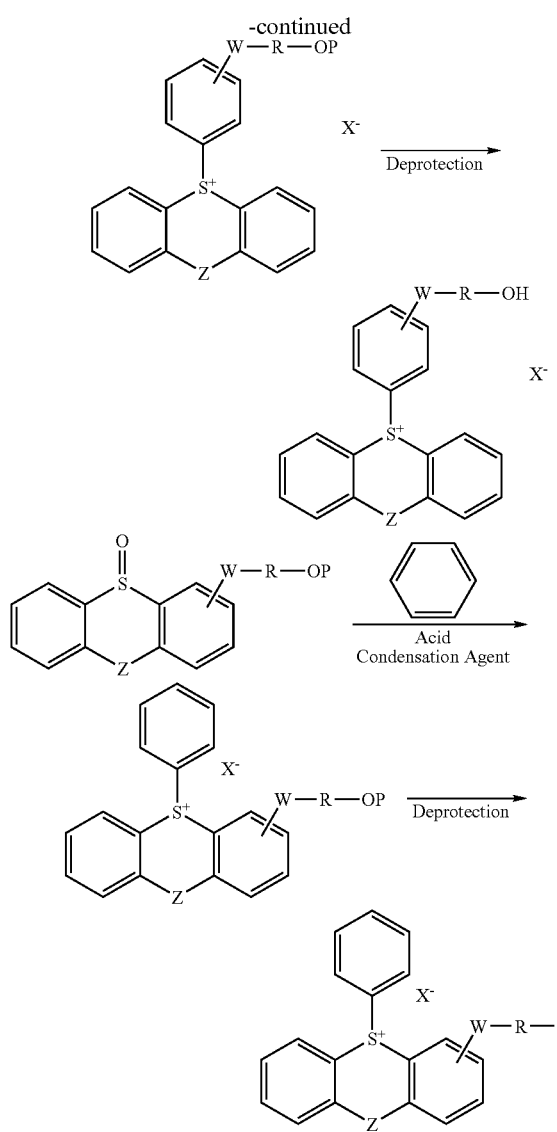

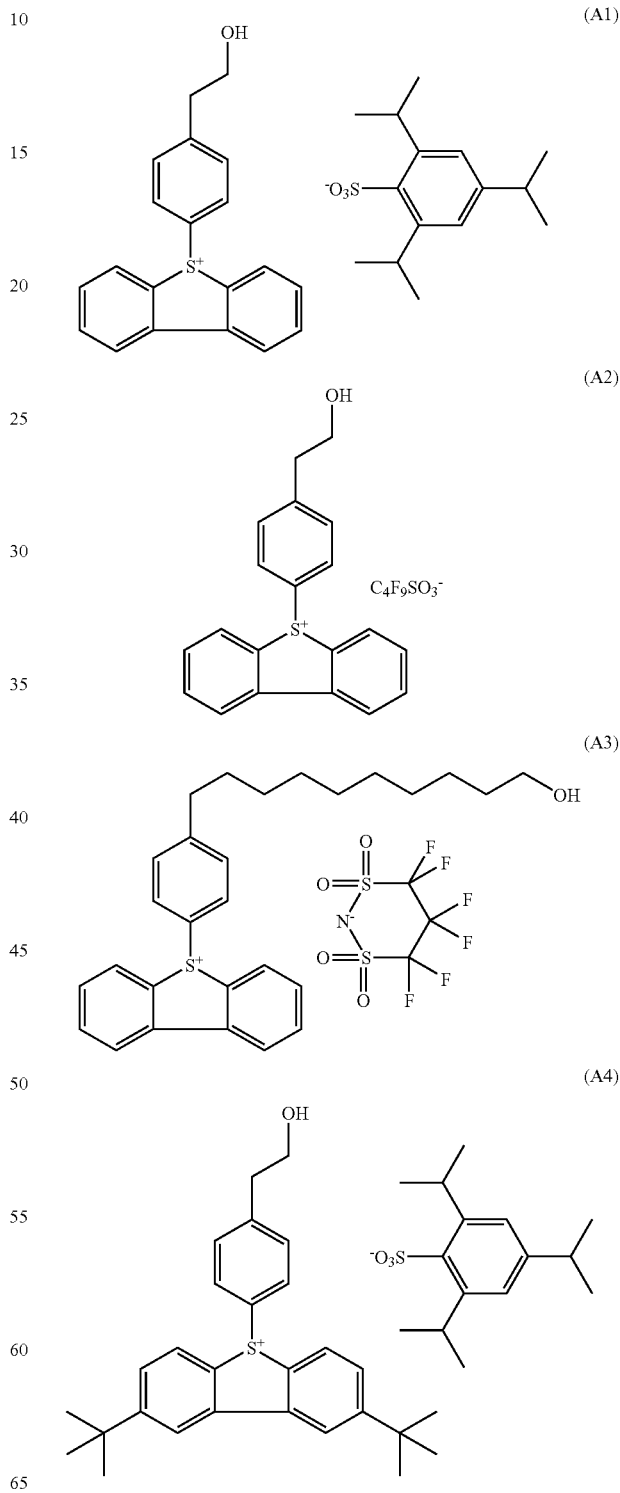

In the above reaction scheme, W represents a divalent linking group, R represents an alkylene group, and P represents a protective group.

As the acids for use in the reaction to form a sulfonium salt, methanesulfonic acid, ethanesulfonic acid, propanesulfonic acid, butanesulfonic acid, pentanesulfonic acid, trifluoromethanesulfonic acid, benzenesulfonic acid, p-toluenesulfonic acid, p-ethylbenzenesulfonic acid, and nonafluorobutanesulfonic acid are exemplified, and the conjugate base of the acid used becomes the anion of the sulfonium. As the condensation agent for use in the reaction to form sulfonium, acid anhydride is exemplified and strong acid anhydrides, e.g., trifluoroacetic anhydride, polyphosphoric anhydride, methanesulfonic anhydride, trifluoromethanesulfonic anhydride, p-toluenesulfonic anhydride, nonafluorobutanesulfonic anhydride, tetrafluorosuccinic anhydride, hexafluoroglutaric anhydride, chlorodifluoroacetic anhydride, pentafluoropropionic anhydride, and heptafluorobutanoic anhydride are exemplified.

As protective group P of a hydroxyl group, ether and ester are exemplified, e.g., methyl ether, aryl ether, benzyl ether, acetic ester, benzoic ester, and carbonic ester are exemplified.

Counter anion $X^-$ can be converted to a desired anion by the addition of the conjugate acid of an objective anion through an ion exchange resin.

The specific examples of the compounds represented by formula (I) are shown below, but the invention is not restricted to these compounds.

(A5)
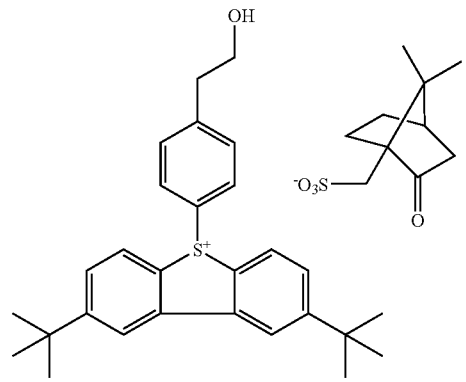
(A6)
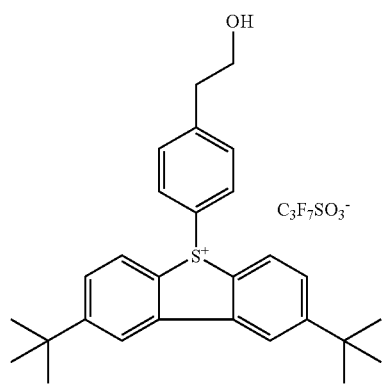
(A7)
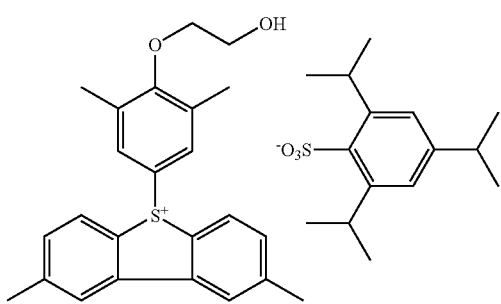
(A8)
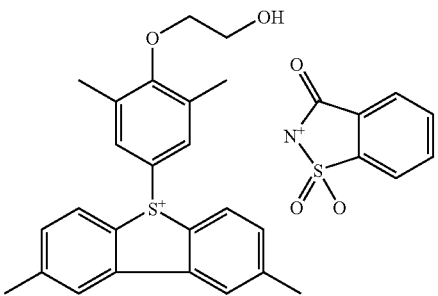
(A9)
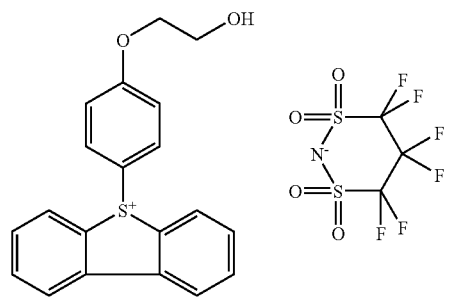
(A10)
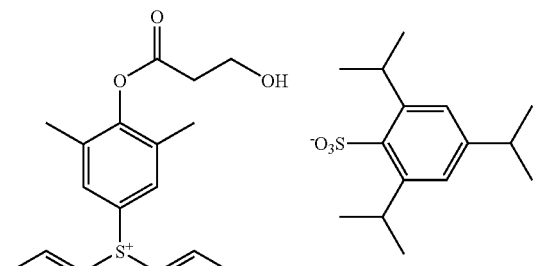
(A11)
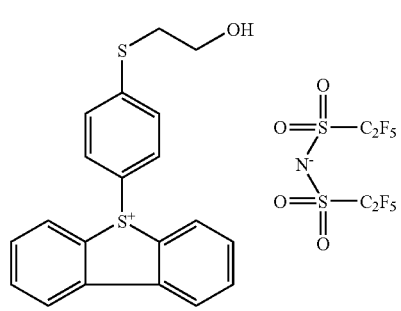
(A12)
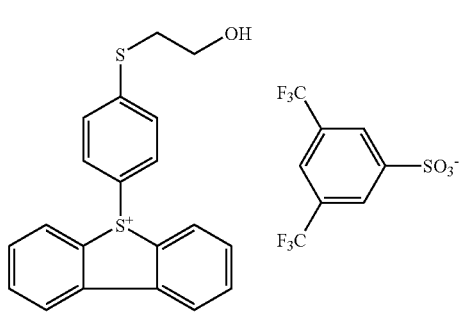
(A13)
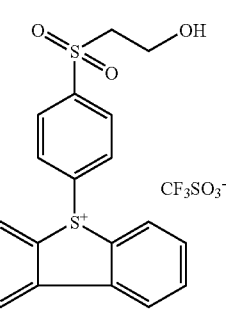
(A14)
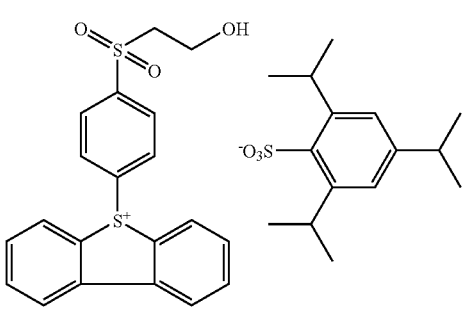

(A15)
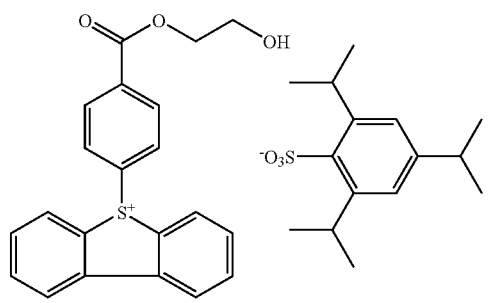
(A16)
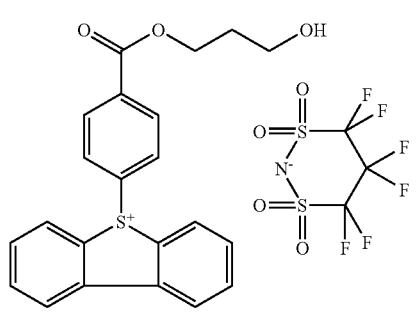
(A17)
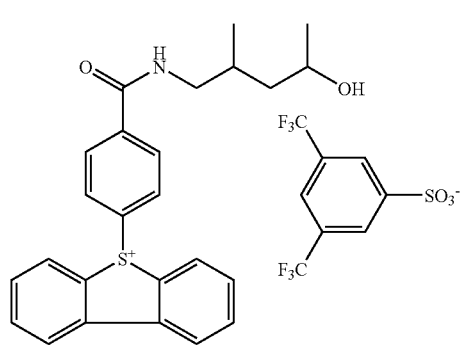
(A18)
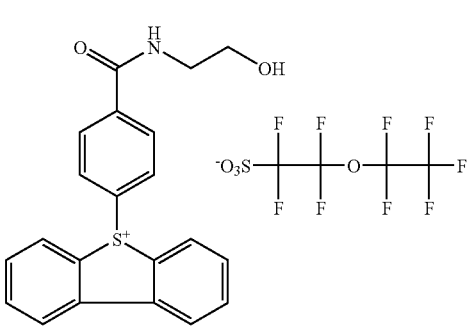
(A19)
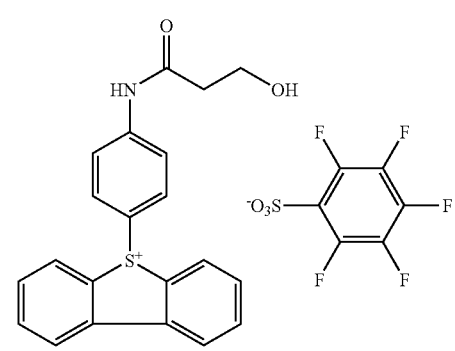
(A20)
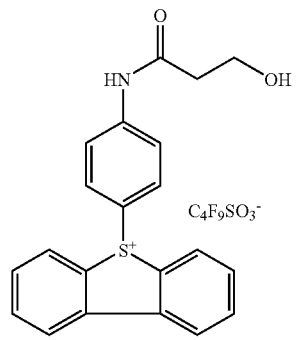
(A21)
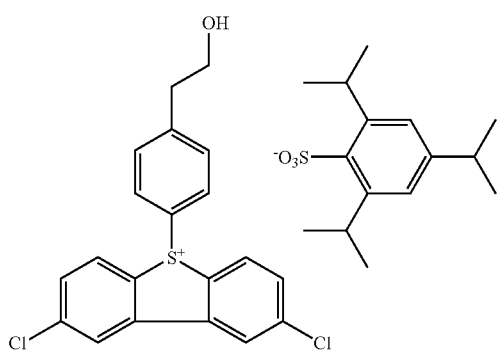
(A22)
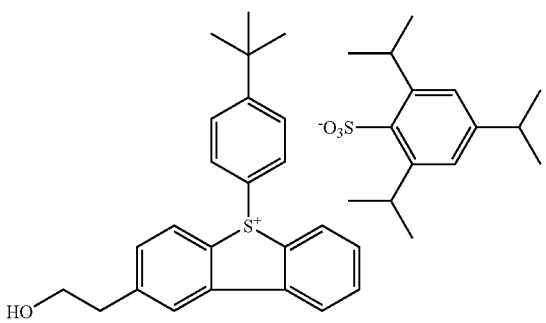
(A23)
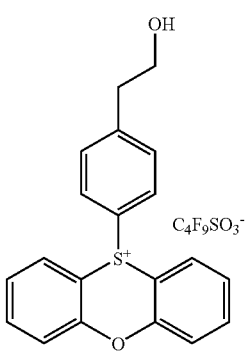

(A24) 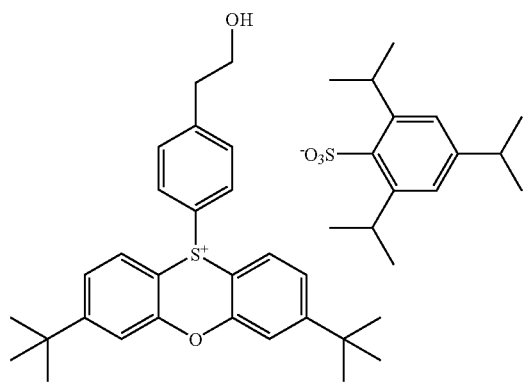
(A25) 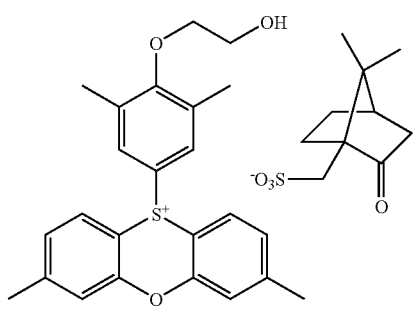
(A26) 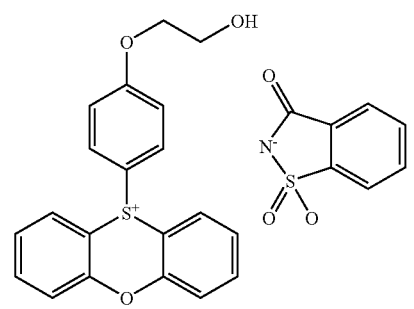
(A27) 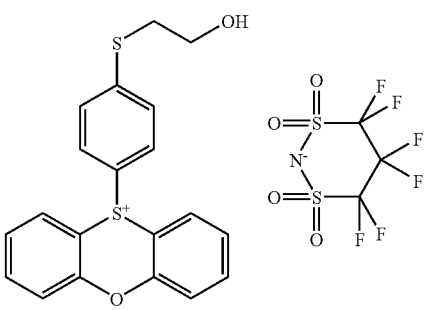
(A28) 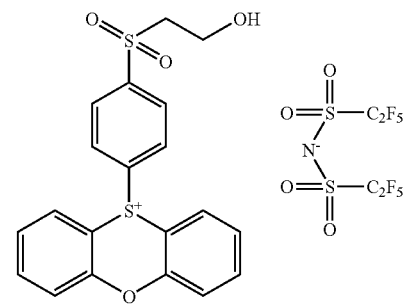
(A29) 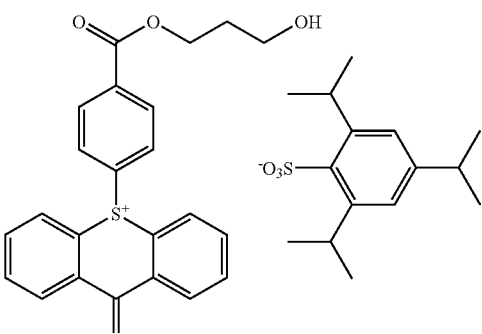
(A30) 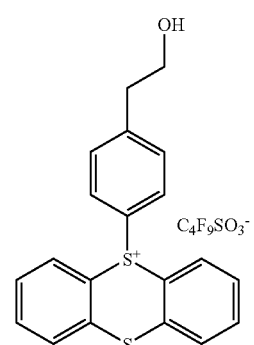
(A31) 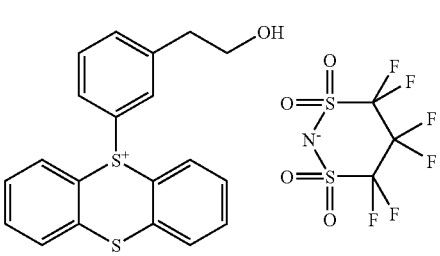
(A32) 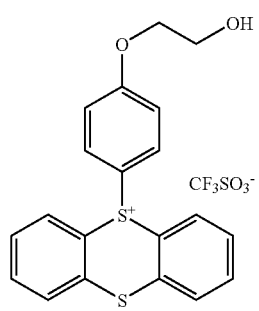
(A33) 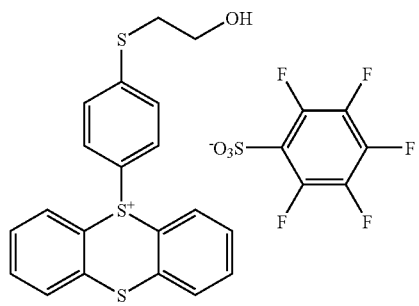

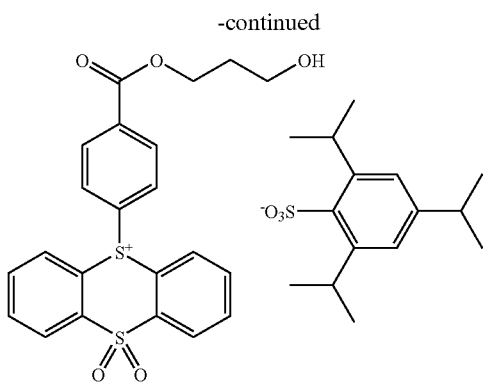
(A34)

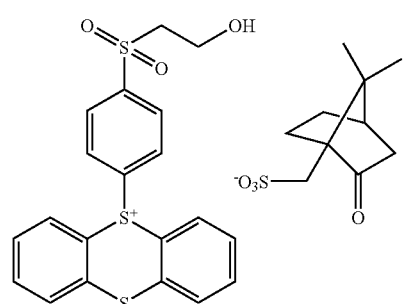
(A35)

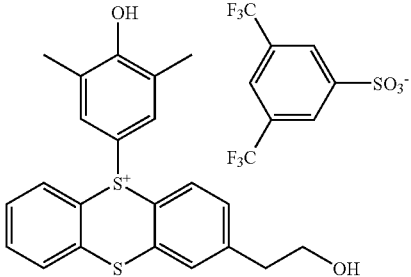
(A36)

[2] Compound Capable of Generating an Acid Upon Irradiation with Actinic Ray or Radiation (Acid Generator A2):

A photosensitive composition in the invention may use other acid generators in combination with acid generator A1. Acid generators other than acid generator A1 are hereinafter referred to as acid generator A2.

As acid generator A2, photocationic polymerization photoinitiators, photoradical polymerization photoinitiators, photo-decoloring agents and photo-discoloring agents of dyestuffs, well-known compounds capable of generating an acid upon irradiation with actinic ray or radiation that are used in micro-resists and the like, and the mixtures of these compounds can be optionally selected and used.

For example, diazonium salt, phosphonium salt, sulfonium salt, iodonium salt, imidosulfonate, oximesulfonate, diazodisulfone, disulfone, and o-nitrobenzylsulfonate are exemplified as acid generator A2.

Further, compounds obtained by introducing a group or a compound capable of generating an acid upon irradiation with actinic ray or radiation to the main chain or side chain of polymers, for example, the compounds disclosed in U.S. Pat. No. 3,849,137, German Patent 3,914,407, JP-A-63-26653, JP-A-55-164824, JP-A-62-69263, JP-A-63-146038, JP-A-63-163452, JP-A-62-153853, JP-A-63-146029, etc., can be used.

The compounds generating an acid by the action of light as disclosed in U.S. Pat. No. 3,779,778, EP 126712, etc., can also be used.

As preferred compounds among the compounds capable of generating an acid upon irradiation with actinic ray or radiation, compounds represented by any of the following formula (ZI), (ZII) or (ZIII) can be exemplified.

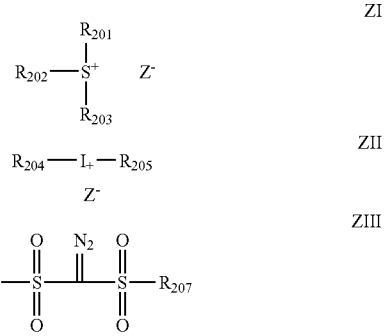

In formula (ZI), $R_{201}$, $R_{202}$ and $R_{203}$ each independently represents an organic group.

The number of carbon atoms of the organic groups represented by $R_{201}$, $R_{202}$ and $R_{203}$ is generally from 1 to 30, and preferably from 1 to 20.

Two of $R_{201}$, $R_{202}$ and $R_{203}$ may be bonded to each other to form a cyclic structure, and an oxygen atom, a sulfur atom, an ester bond, an amido bond or a carbonyl group may be contained in the ring. As the group formed by bonding two of $R_{201}$, $R_{202}$ and $R_{203}$, an alkylene group (e.g., a butylene group, a pentylene group) can be exemplified.

$Z^-$ represents a non-nucleophilic anion.

The examples of the non-nucleophilic anions represented by $Z^-$ include, e.g., a sulfonate anion, a carboxylate anion, a sulfonylimide anion, a bis(alkylsulfonyl)imide anion, and a tris(alkylsulfonyl)methyl anion.

A non-nucleophilic anion is an anion having extremely low ability of causing a nucleophilic reaction and capable of restraining the aging decomposition due to an intramolecular nucleophilic reaction, so that the aging stability of a resist can be improved with a non-nucleophilic anion.

As sulfonate anions, e.g., an aliphatic sulfonate anion, an aromatic sulfonate anion and a camphor sulfonate anion are exemplified.

As carboxylate anions, e.g., an aliphatic carboxylate anion, an aromatic carboxylate anion and an aralkylcarboxylate anion are exemplified.

The aliphatic moiety in the aliphatic sulfonate anion may be an alkyl group or a cycloalkyl group, preferably an alkyl group having from 1 to 30 carbon atoms and a cycloalkyl group having from 3 to 30 carbon atoms, e.g., a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclopentyl group, a cyclohexyl group, an adamantyl group, a norbornyl group, and a boronyl group are exemplified.

The aromatic group in the aromatic sulfonate anion is preferably an aryl group having from 6 to 14 carbon atoms, e.g., a phenyl group, a tolyl group, and a naphthyl group are exemplified.

The alkyl group, cycloalkyl group and aryl group in the aliphatic sulfonate anion and aromatic sulfonate anion may have a substituent. As the substituents of the alkyl group, cycloalkyl group and aryl group in the aliphatic sulfonate anion and aromatic sulfonate anion, e.g., a nitro group, a halogen atom (a fluorine atom, a chlorine atom, a bromine atom, and an iodine atom), a carboxyl group, a hydroxyl group, an amino group, a cyano group, an alkoxyl group (preferably having from 1 to 15 carbon atoms), a cycloalkyl group (preferably having from 3 to 15 carbon atoms), an aryl group (preferably having from 6 to 14 carbon atoms), an alkoxycarbonyl group (preferably having from 2 to 7 carbon atoms), an acyl group (preferably having from 2 to 12 carbon atoms), an alkoxycarbonyloxy group (preferably having from 2 to 7 carbon atoms), etc., are exemplified. As for the aryl group and the cyclic structure of each group, an alkyl group (preferably having from 1 to 15 carbon atoms) can further be exemplified as the substituent.

As the aliphatic moiety in the aliphatic carboxylate anion, the same alkyl group and cycloalkyl group as in the aliphatic sulfonate anion can be exemplified.

As the aromatic group in the aromatic carboxylate anion, the same aryl group as in the aromatic sulfonate anion can be exemplified.

As the aralkyl group in the aralkylcarboxylate anion, preferably an aralkyl group having from 6 to 12 carbon atoms, e.g., a benzyl group, a phenethyl group, a naphthylmethyl group, and a naphthylethyl group can be exemplified.

The alkyl group, cycloalkyl group, aryl group, and aralkyl group in the aliphatic carboxylate anion, aromatic carboxylate anion and aralkylcarboxylate anion may have a substituent. As the substituents of the alkyl group, cycloalkyl group, aryl group and aralkyl group in the aliphatic carboxylate anion, aromatic carboxylate anion and aralkylcarboxylate anion, e.g., the same halogen atom, alkyl group, cycloalkyl group, alkoxyl group and alkylthio group as in the aromatic sulfonate anion can be exemplified.

As the sulfonylimide anion, e.g., a saccharin anion can be exemplified.

The alkyl group in the bis(alkylsulfonyl)imide anion and tris(alkylsulfonyl)methyl anion is preferably an alkyl group having from 1 to 5 carbon atoms, e.g., a methyl group, an ethyl group, a propyl group, an isopropyl group, an n-butyl group, an isobutyl group, a sec-butyl group, a pentyl group, a neopentyl group, etc., are exemplified. As the substituents of these alkyl groups, a halogen atom, an alkyl group substituted with a halogen atom, an alkoxyl group, an alkylthio group, etc., can be exemplified, and an alkyl group substituted with a fluorine atom is preferred.

As other non-nucleophilic anions, e.g., fluorinated phosphorus, fluorinated boron and fluorinated antimony can be exemplified.

As the non-nucleophilic anions represented by $Z^-$, an aliphatic sulfonate anion in which the $\alpha$-position of the sulfonic acid is substituted with a fluorine atom, an aromatic sulfonate anion substituted with a fluorine atom or a group having a fluorine atom, a bis(alkylsulfonyl)imide anion having an alkyl group substituted with a fluorine atom, and a tris(alkylsulfonyl)methide anion having an alkyl group substituted with a fluorine atom are preferred. More preferred non-nucleophilic anions are an aliphatic perfluorosulfonate anion having from 4 to 8 carbon atoms, and a benzenesulfonate anion having a fluorine atom, and still more preferred non-nucleophilic anions are a nonafluorobutanesulfonate anion, a perfluorooctanesulfonate anion, a pentafluorobenzenesulfonate anion, and a 3,5-bis(trifluoromethyl)benzenesulfonate anion.

As the examples of the organic groups represented by $R_{201}$, $R_{202}$ and $R_{203}$, the corresponding groups in the later-described compounds represented by formula (ZI-1), (ZI-2) or (ZI-3) can be exemplified.

The compound represented by formula (ZI) may be a compound having a plurality of structures represented by formula (ZI). For instance, compound (ZI) may be a compound having a structure that at least one of $R_{201}$, $R_{202}$ and $R_{203}$ of a compound represented by formula (ZI) is bonded to at least one of $R_{201}$, $R_{202}$ and $R_{203}$ of another compound represented by formula (ZI).

The following compounds (ZI-1), (ZI-2) and (ZI-3) can be exemplified as more preferred components (ZI).

Compound (ZI-1) is an arylsulfonium compound that at least one of $R_{201}$ to $R_{203}$ in formula (ZI) represents an aryl group, i.e., a compound having arylsulfonium as a cation.

All of $R_{201}$ to $R_{203}$ of the arylsulfonium compound may be aryl groups, or a part of $R_{201}$ to $R_{203}$ may be an aryl group and the remainder may be an alkyl group or a cycloalkyl group.

As the arylsulfonium compounds, e.g., a triarylsulfonium compound, a diarylalkylsulfonium compound, an aryldialkylsulfonium compound, a diarylcycloalkylsulfonium compound, and an aryldicycloalkylsulfonium compound are exemplified.

As the aryl groups of the arylsulfonium compound, a phenyl group and a naphthyl group are preferred, and the more preferred group is a phenyl group. The aryl group may be an aryl group having a heterocyclic structure having an oxygen atom, a nitrogen atom or a sulfur atom. As the aryl group having a heterocyclic structure, e.g., a pyrrole residue (a group formed by eliminating one hydrogen atom from pyrrole), a furan residue (a group formed by eliminating one hydrogen atom from furan), a thiophene residue (a group formed by eliminating one hydrogen atom from thiophene), an indole residue (a group formed by eliminating one hydrogen atom from indole), a benzofuran residue (a group formed by eliminating one hydrogen atom from benzofuran), and a benzothiophene residue (a group formed by eliminating one hydrogen atom from benzothiophene) can be exemplified. When the arylsulfonium compound has two or more aryl groups, these two or more aryl groups may be the same or different.

As the alkyl group or the cycloalkyl group that the arylsulfonium compound has according to necessity, a straight chain or branched alkyl group having from 1 to 15 carbon atoms and a cycloalkyl group having from 3 to 15 carbon atoms are preferred, e.g., a methyl group, an ethyl group, a propyl group, an n-butyl group, a sec-butyl group, a t-butyl group, a cyclopropyl group, a cyclobutyl group and a cyclohexyl group can be exemplified.

The aryl group, alkyl group and cycloalkyl group represented by $R_{201}$, $R_{202}$ and $R_{203}$ may have a substituent and, e.g., an alkyl group (e.g., having from 1 to 15 carbon atoms), a cycloalkyl group (e.g., having from 3 to 15 carbon atoms), an aryl group (e.g., having from 6 to 14 carbon atoms), an alkoxyl group (e.g., having from 1 to 15 carbon atoms), a halogen atom, a hydroxyl group, and a phenylthio group are exemplified as the substituents. The preferred substituents are a straight chain or branched alkyl group having from 1 to 12 carbon atoms, a cycloalkyl group having from 3 to 12 carbon atoms, and a straight chain, branched or cyclic alkoxyl group having from 1 to 12 carbon atoms, and the more preferred substituents are an alkyl group having from 1 to 4 carbon atoms and an alkoxyl group having from 1 to 4 carbon atoms. The substituent may be substituted on any one of three of $R_{201}$ to $R_{203}$, or may be substituted on all of the three. When $R_{201}$, $R_{202}$ and $R_{203}$ each independently represents an aryl group, it is preferred that the substituent be substituted on the p-position of the aryl group.

Compound (ZI-2) is described below.

Compound (ZI-2) is a compound in the case where $R_{201}$, $R_{202}$ and $R_{203}$ in formula (ZI) each independently represents an organic group not containing an aromatic ring. The aromatic ring also includes an aromatic ring containing a hetero atom.

The organic groups not containing an aromatic ring represented by $R_{201}$ to $R_{203}$ generally have from 1 to 30 carbon atoms, and preferably from 1 to 20 carbon atoms.

$R_{201}$, $R_{202}$ and $R_{203}$ each preferably represents an alkyl group, a cycloalkyl group, an allyl group, or a vinyl group, more preferably a straight chain or branched 2-oxoalkyl group, a 2-oxocycloalkyl group or an alkoxycarbonylmethyl group, and especially preferably a straight or branched 2-oxoalkyl group.

The alkyl group and cycloalkyl group represented by $R_{201}$ to $R_{203}$ are preferably a straight chain or branched alkyl group having from 1 to 10 carbon atoms (e.g., a methyl group, an ethyl group, a propyl group, a butyl group, a pentyl group), and a cycloalkyl group having from 3 to 10 carbon atoms (e.g., a cyclopentyl group, a cyclohexyl group, a norbornyl group). The alkyl group is more preferably a 2-oxoalkyl group or an alkoxycarbonylmethyl group. The cycloalkyl group is more preferably a 2-oxocycloalkyl group.

The 2-oxoalkyl group may be either a straight chain or branched group, and a group having >C=O on the 2-position of the above alkyl group can be exemplified as a preferred group.

The 2-oxocycloalkyl group is preferably a group having >C=O on the 2-position of the above cycloalkyl group.

As the alkoxyl group in the alkoxycarbonylmethyl group, preferably an alkoxyl group having from 1 to 5 carbon atoms (e.g., a methoxy group, an ethoxy group, a propoxy group, a butoxy group, a pentoxy group) can be exemplified.

$R_{201}$ to $R_{203}$ may further be substituted with a halogen atom, an alkoxyl group (e.g., having from 1 to 5 carbon atoms), a hydroxyl group, a cyano group, or a nitro group.

Compound (ZI-3) is a compound represented by the following formula (ZI-3), which compound has a phenacylsulfonium salt structure.

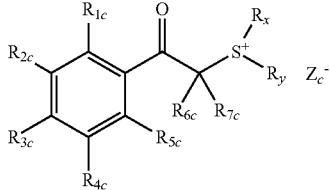

(ZI-3)

In formula (ZI-3), $R_{1c}$, $R_{2c}$, $R_{3c}$, $R_{4c}$ and $R_{5c}$ each independently represents a hydrogen atom, an alkyl group, a cycloalkyl group, an alkoxyl group, or a halogen atom.

$R_{6c}$ and $R_{7c}$ each independently represents a hydrogen atom, an alkyl group or a cycloalkyl group.

$R_x$ and $R_y$ each independently represents an alkyl group, a cycloalkyl group, an allyl group, or a vinyl group.

Any two or more of $R_{1c}$ to $R_{5c}$, $R_{6c}$ and $R_{7c}$, and $R_x$ and $R_y$ may be bonded to each other to form cyclic structures, respectively, and the cyclic structures may contain an oxygen atom, a sulfur atom, an ester bond, or an amido bond. As the groups formed by any two or more of $R_{1c}$ to $R_{5c}$, $R_{6c}$ and $R_{7c}$, and $R_x$ and $R_y$, a butylene group, a pentylene group, etc., can be exemplified.

$Z_c^-$ represents a non-nucleophilic anion, and the same non-nucleophilic anions as represented by $Z^-$ in formula (ZI) can be exemplified.

The alkyl groups represented by $R_{1c}$ to $R_{7c}$ may be either straight chain or branched, e.g., an alkyl group having from 1 to 20 carbon atoms, preferably a straight chain or branched alkyl group having from 1 to 12 carbon atoms (e.g., a methyl group, an ethyl group, a straight chain or branched propyl group, a straight chain or branched butyl group, a straight chain or branched pentyl group) can be exemplified. As the cycloalkyl groups represented by $R_{1c}$ to $R_{7c}$, a cycloalkyl group having from 3 to 8 carbon atoms (e.g., a cyclopentyl group and a cyclohexyl group) can be exemplified.

The alkoxyl groups represented by $R_{1c}$ to $R_{5c}$ may be any of straight chain, branched and cyclic, e.g., an alkoxyl group having from 1 to 10 carbon atoms, preferably a straight chain or branched alkoxyl group having from 1 to 5 carbon atoms (e.g., a methoxy group, an ethoxy group, a straight chain or branched propoxy group, a straight chain or branched butoxy group, a straight chain or branched pentoxy group), a cyclic alkoxyl group having from 3 to 8 carbon atoms (e.g., a cyclopentyloxy group, a cyclohexyloxy group) can be exemplified.

It is preferred that any of $R_{1c}$ to $R_{5c}$ represents a straight chain or branched alkyl group, a cycloalkyl group, or a straight chain, branched or cyclic alkoxyl group, it is more preferred that the sum total of the carbon atoms of $R_{1c}$ to $R_{5c}$ is from 2 to 15, by which the solubility in a solvent increases and generation of particles during preservation can be restrained.

As the alkyl group and cycloalkyl group represented by $R_x$ and $R_y$, the same alkyl groups and cycloalkyl groups represented by $R_{1c}$ to $R_{7c}$ can be exemplified, and a 2-oxoalkyl group, a 2-oxocycloalkyl group and an alkoxycarbonylmethyl group are more preferred.

As the 2-oxoalkyl group and the 2-oxocycloalkyl group, groups respectively having >C=O on the 2-position of the alkyl group and the cycloalkyl group represented by $R_{1c}$ to $R_{7c}$ can be exemplified.

As the alkoxyl group of the alkoxycarbonylmethyl group, the same alkoxyl groups as those represented by $R_{1c}$ to $R_{5c}$ can be exemplified.

$R_x$ and $R_y$ each preferably represents an alkyl group or a cycloalkyl group having 4 or more carbon atoms, more preferably 6 or more carbon atoms, and still more preferably an alkyl group or a cycloalkyl group having 8 or more carbon atoms.

In formulae (ZII) and (ZII), $R_{204}$, $R_{205}$, $R_{206}$ and $R_{207}$ each independently represents an aryl group, an alkyl group or a cycloalkyl group.

The aryl group represented by $R_{204}$ to $R_{207}$ is preferably a phenyl group or a naphthyl group, and more preferably a phenyl group. The aryl group represented by $R_{204}$ to $R_{207}$ may be an aryl group having a heterocyclic structure and having an oxygen atom, a nitrogen atom or a sulfur atom. As the aryl group having a heterocyclic structure, e.g., a pyrrole residue (a group formed by eliminating one hydrogen atom from pyrrole), a furan residue (a group formed by eliminating one hydrogen atom from furan), a thiophene residue (a group formed by eliminating one hydrogen atom from thiophene), an indole residue (a group formed by eliminating one hydrogen atom from indole), a benzofuran residue (a group formed by eliminating one hydrogen atom from benzofuran), and a benzothiophene residue (a group formed by eliminating one hydrogen atom from benzothiophene) can be exemplified.

The alkyl group and the cycloalkyl group represented by $R_{204}$ to $R_{207}$ are preferably a straight chain or branched alkyl group having from 1 to 10 carbon atoms (e.g., a methyl group, an ethyl group, a propyl group, a butyl group, a pentyl group), and a cycloalkyl group having from 3 to 10 carbon atoms (e.g., a cyclopentyl group, a cyclohexyl group, a norbornyl group).

The aryl group, alkyl group and cycloalkyl group represented by $R_{204}$ to $R_{207}$ may have a substituent. As the substituents that the aryl group, alkyl group and cycloalkyl group represented by $R_{204}$ to $R_{207}$ may have, e.g., an alkyl group (e.g., having from 1 to 15 carbon atoms), a cycloalkyl group (e.g., having from 3 to 15 carbon atoms), an aryl group (e.g., having from 6 to 15 carbon atoms), an alkoxyl group (e.g., having from 1 to 15 carbon atoms), a halogen atom, a hydroxyl group, and a phenylthio group can be exemplified.

$Z^-$ represents a non-nucleophilic anion, and the same non-nucleophilic anions as those represented by $Z^-$ in formula (ZI) can be exemplified.

As the compounds capable of generating an acid upon irradiation with actinic ray or radiation usable in the invention, the compounds represented by the following formula (ZIV), (ZV) or (ZVI) can further be exemplified.

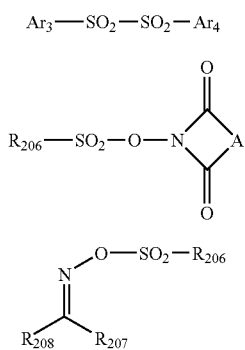

In formulae (ZIV), (ZV) and (ZVI), $Ar_3$ and $Ar_4$ each independently represents an aryl group.

$R_{206}$, $R_{207}$ and $R_{208}$ each independently represents an alkyl group, a cycloalkyl group or an aryl group.

A represents an alkylene group, an alkenylene group or an arylene group.

Of the compounds capable of generating an acid upon irradiation with actinic ray or radiation, more preferred compounds are the compounds represented by formulae (ZI), (ZII) and (ZIII).

Further, as the compounds capable of generating an acid upon irradiation with actinic ray or radiation, a compound capable of generating an acid having one sulfonic acid group or imido group is preferred, a compound capable of generating a monovalent perfluoroalkanesulfonic acid, a compound capable of generating an aromatic sulfonic acid substituted with a monovalent fluorine atom or a group containing a fluorine atom, and a compound capable of generating an imidic acid substituted with a monovalent fluorine atom or a group containing a fluorine atom are more preferred, and a sulfonium salt of a fluorine-substituted alkanesulfonic acid, a fluorine-substituted benzenesulfonic acid, or a fluorine-substituted imidic acid is still more preferred. As the compounds capable of generating an acid upon irradiation with actinic ray or radiation, a fluorine-substituted alkanesulfonic acid, a fluorine-substituted benzenesulfonic acid, and fluorine-substituted imidic acid each having pKa of generated acid of −1 or less are especially preferred, by which sensitivity is improved.

Of the compounds capable of generating an acid upon irradiation with actinic ray or radiation, especially preferred examples are shown below.

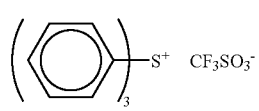 (z1)

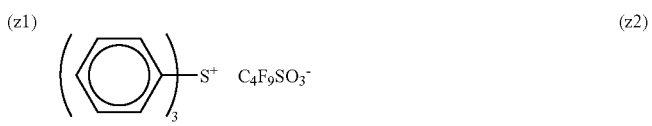 (z2)

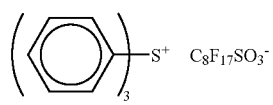 (z3)

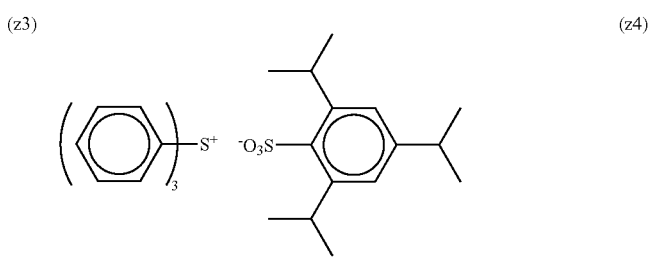 (z4)

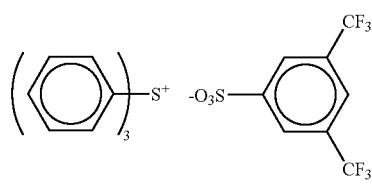 (z5)

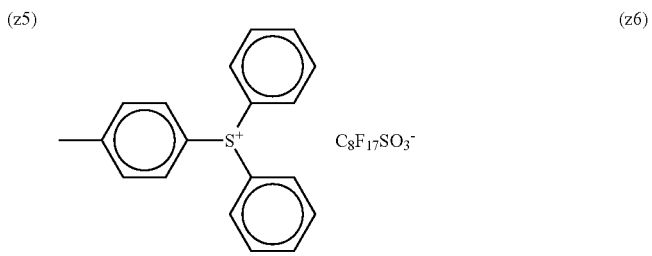 (z6)

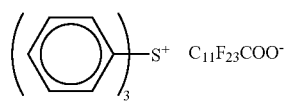 (z7)

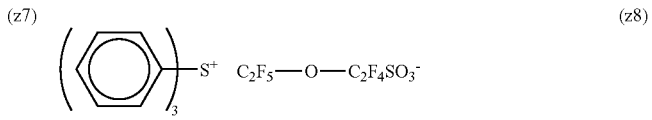 (z8)

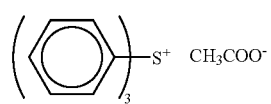
-continued
(z9)
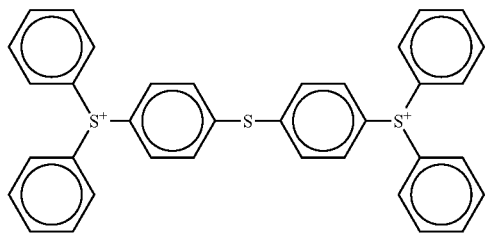
(z10)
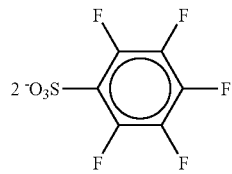
(z11)
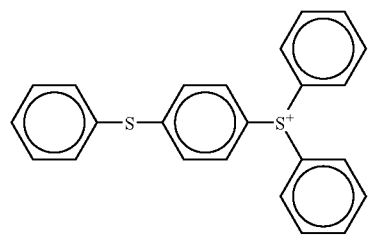 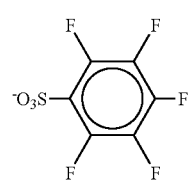
(z12)
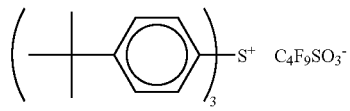
(z13)
(z14)
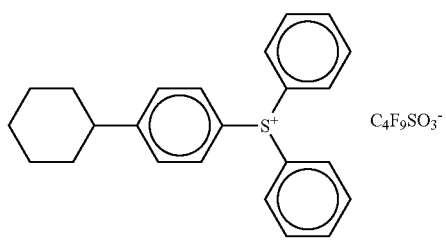
(z15)
(z16)
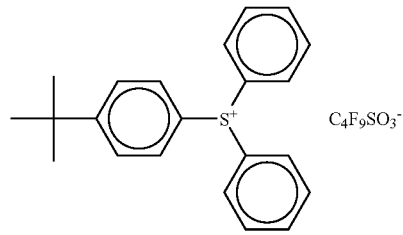 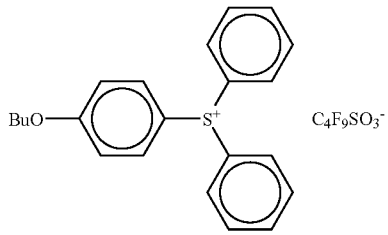
(z17)
(z18)
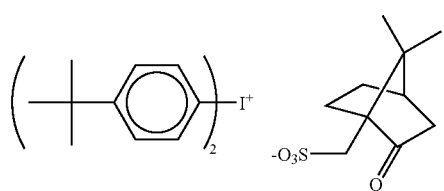 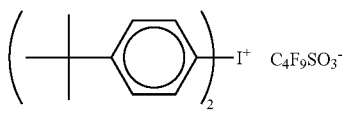
(z19)
(z20)
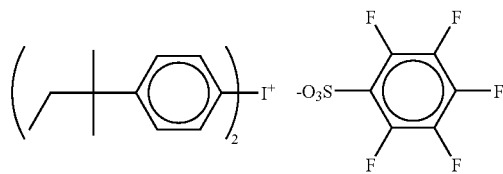 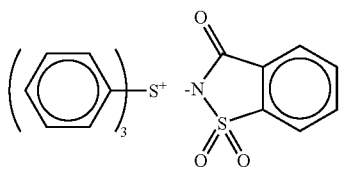
(z21)
(z22)
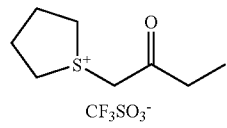 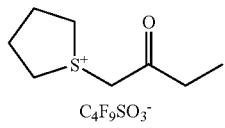

-continued
(z23) 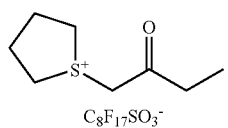
(z24) 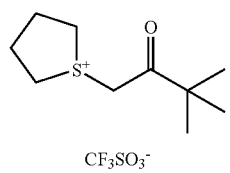
(z25) 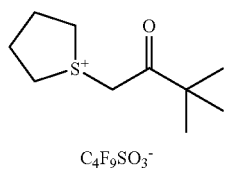
(z26) 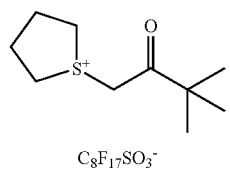
(z27) 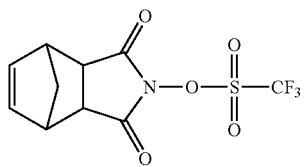
(z28) 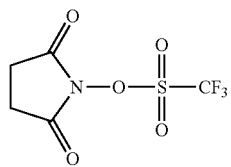
(z29) 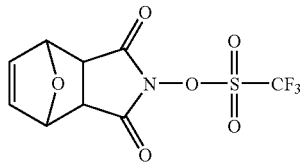
(z30) 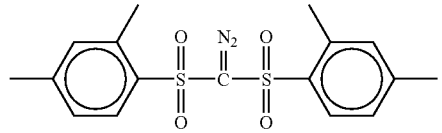
(z31) 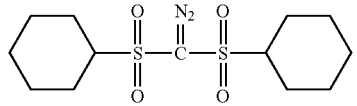
(z32) 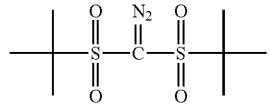
(z33) 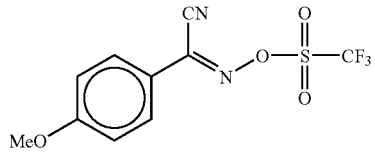
(z34) 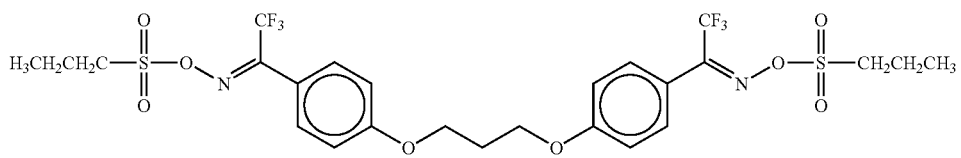
(z35) 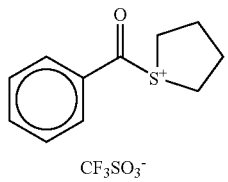
(z36) 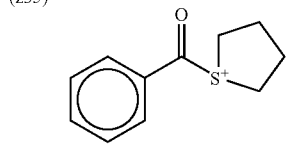
(z37) 
(z38) 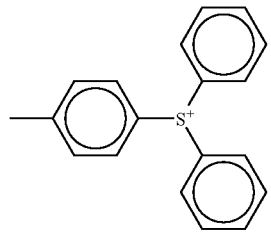

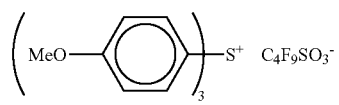
(z39)
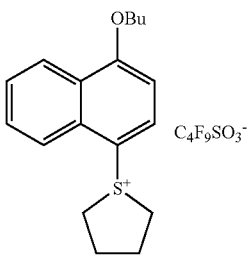
(z40)
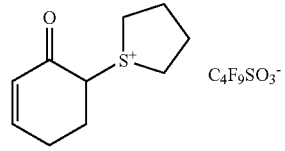
(z41)
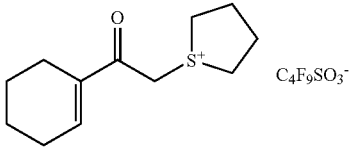
(z42)
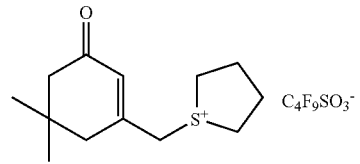
(z43)
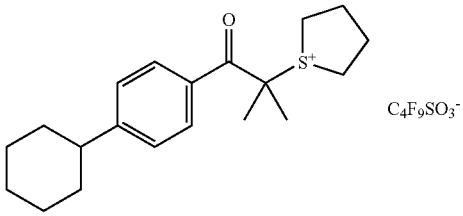
(z44)
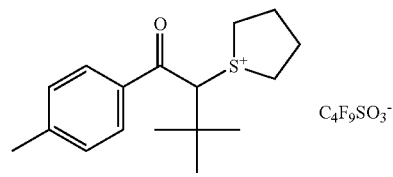
(z45)
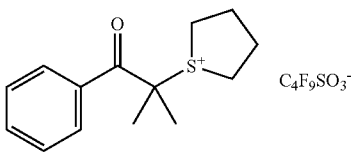
(z46)
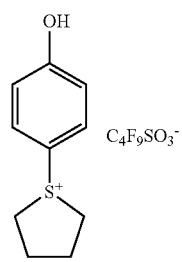
(z47)
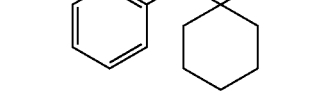
(z48)
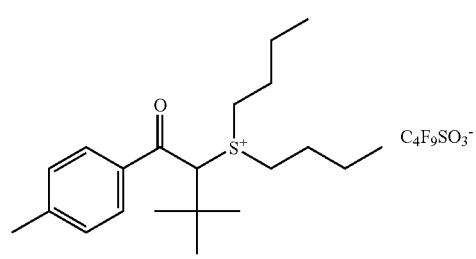
(z49)
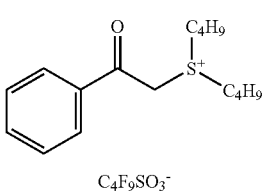
(z50)
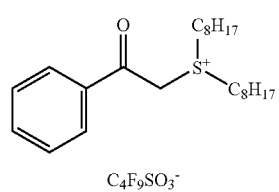
(z51)
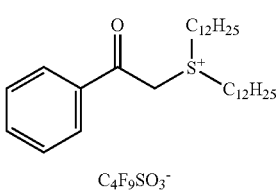
(z52)

-continued
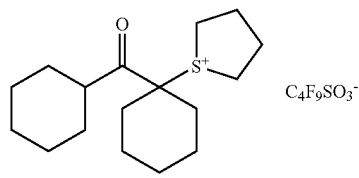 (z53)
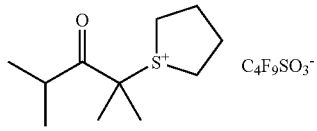 (z54)
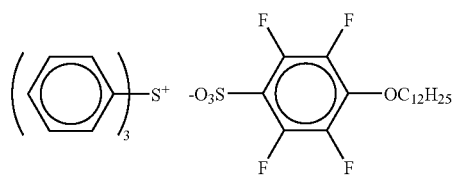 (z55)
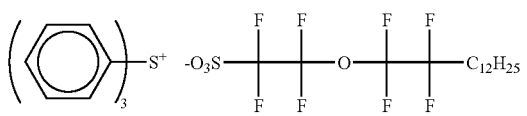 (z56)
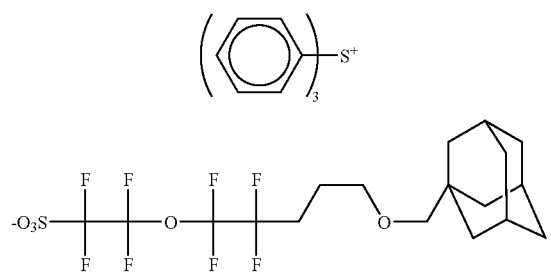 (z57)
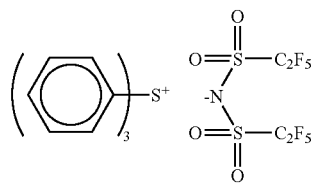 (z59)
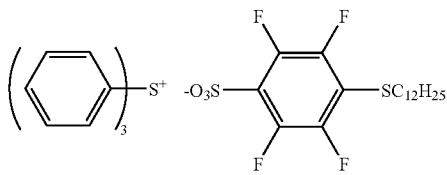 (z58)
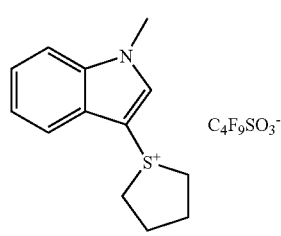 (z61)
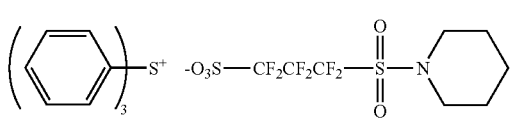 (z60)
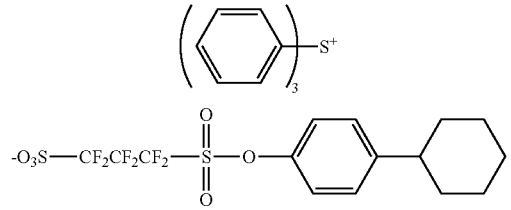 (z63)
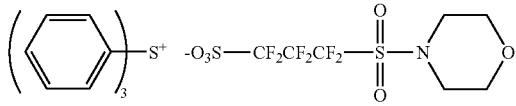 (z62)
(z64)
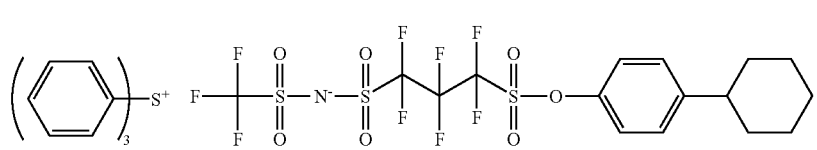 (z65)

Acid generator A2 can also be used alone or in combination two or more.

The amount of acid generator A2 is preferably 50 mass % or less to acid generator A1, and more preferably 30 mass % or less.

[3] Resin (B) capable of decomposing by the action of an acid to increase solubility in an alkali developing solution:

A resin capable of decomposing by the action of an acid to increase solubility in an alkali developing solution for use in a positive photosensitive composition in the invention is a resin having a group capable of decomposing by the action of an acid to generate an alkali-soluble group ("an acid decomposable group") on the main chain or side chain of the resin, or on both the main chain and side chain. Of these resins, a resin having an acid-decomposable group on the side chain is more preferred.

A preferred acid-decomposable group is a group obtained by substituting the hydrogen atom of an alkali-soluble group such as a —COOH group or an —OH group with a group capable of desorption by the action of an acid.

A preferred acid-decomposable group in the invention is an acetal group or a tertiary ester group.

The parent resin in the case where the acid-decomposable group is bonded as the side chain is an alkali-soluble resin having an —OH group or a —COOH group on the side chain. For example, the later-described alkali-soluble resins can be exemplified.

The alkali dissolution rate of such alkali-soluble resins is preferably 170 Å/sec or more when measured with 0.261N tetramethylammonium hydroxide (TMAH) at 23° C., and especially preferably 330 Å/sec or more.

From this point of view, particularly preferred alkali-soluble resins are o-, m-, p-poly(hydroxystyrene) and copolymers thereof, hydrogenated poly(hydroxystyrene), halogen- or alkyl-substituted poly(hydroxystyrene), a partially O-alkylated or O-acylated product of poly-(hydroxystyrene), styrene-hydroxystyrene copolymers, α-methylstyrene-hydroxystyrene copolymers, alkali-soluble resins having a hydroxystyrene structural unit such as hydrogenated novolak resins, (meth)acrylic acid, and alkali-soluble resins containing a repeating unit having a carboxyl group such as norbornenecarboxylic acid.

As repeating units having a preferred acid-decomposable group, e.g., t-butoxycarbonyloxystyrene, 1-alkoxyethoxystyrene, and (meth)acrylic acid tertiary alkyl ester are exemplified, and 2-alkyl-2-adamantyl(meth)acrylate and dialkyl (1-adamantyl)methyl(meth)acrylate are more preferred.

Components (B) for use in the invention can be obtained, as disclosed in EP 254853, JP-A-2-25850, JP-A-3-223860 and JP-A-4-251259, by reacting an alkali-soluble resin with the precursor of an acid-decomposable group, or copolymerizing an alkali-soluble resin monomer to which an acid-decomposable group is bonded with various monomers.

When the positive photosensitive composition of the invention is irradiated with KrF excimer laser beams, electron beams, X-rays, or high energy rays of wavelength of 50 nm or lower (e.g., EUV), it is preferred for a resin of component (B) to have a hydroxystyrene repeating unit, more preferably a copolymer of hydroxystyrene/hydroxystyrene protected with an acid-decomposable group, or hydroxystyrene/(meth) acrylic acid tertiary alkyl ester.

The specific examples of component (B) for use in the invention are shown below, but the invention is not restricted thereto.

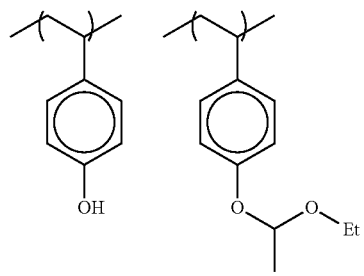

(R-1)

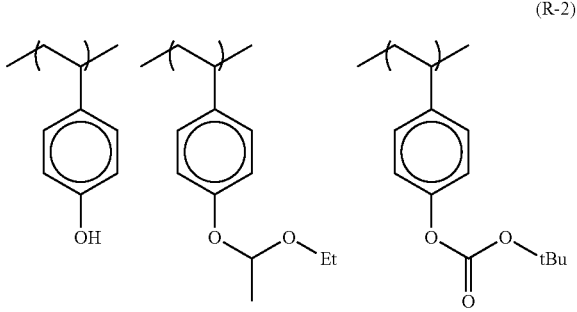

(R-2)

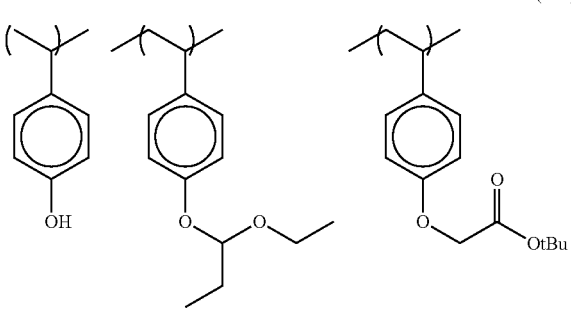

(R-3)

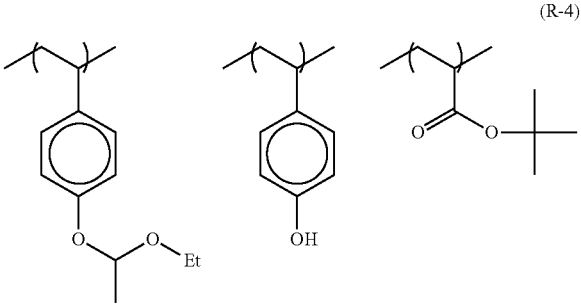

(R-4)

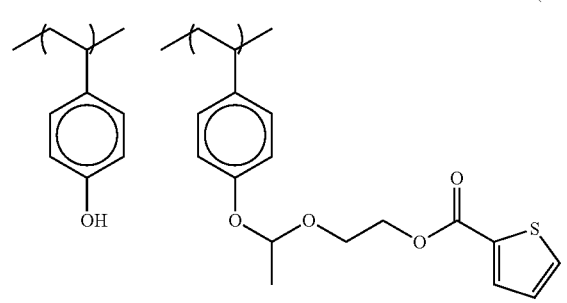

(R-5)

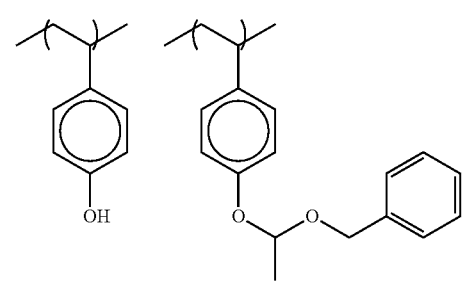
(R-6)
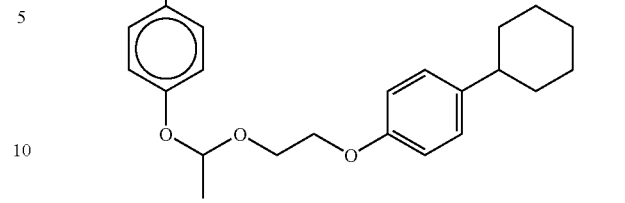
(R-7)
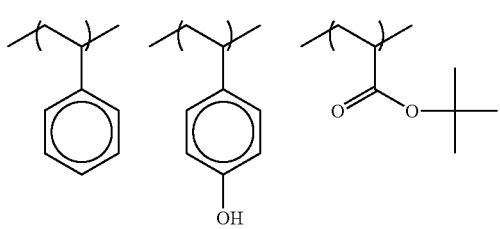
(R-8)
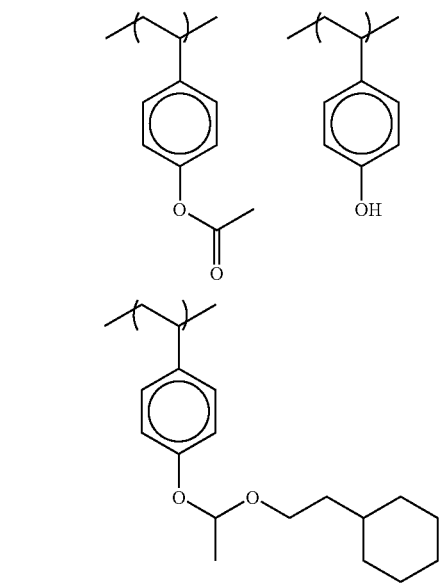
(R-9)
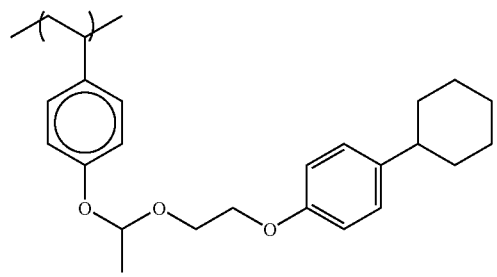
(R-11)
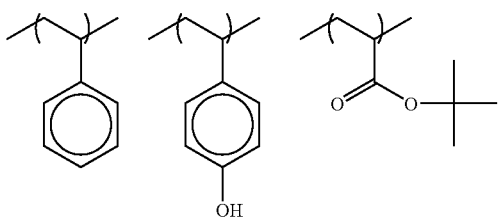
(R-12)
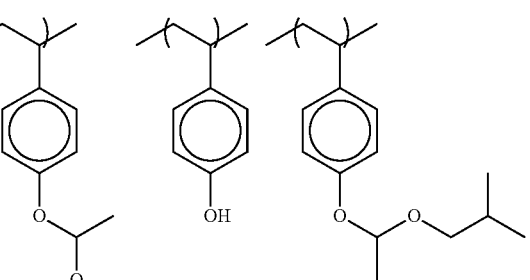
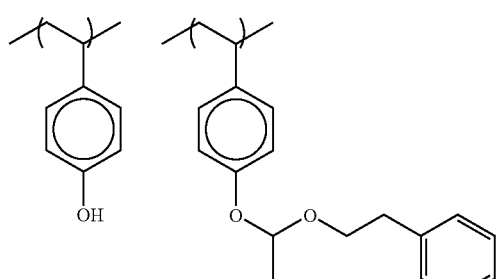
(R-10)
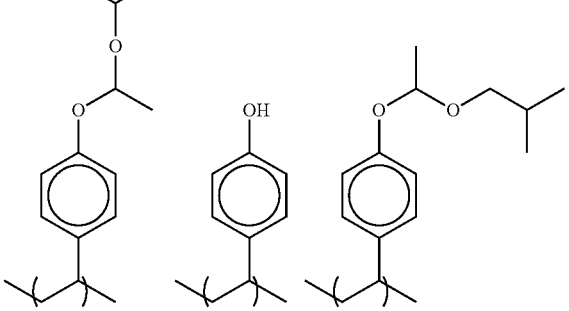
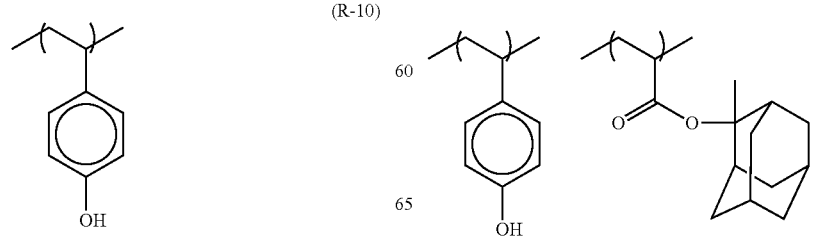
(R-13)

-continued

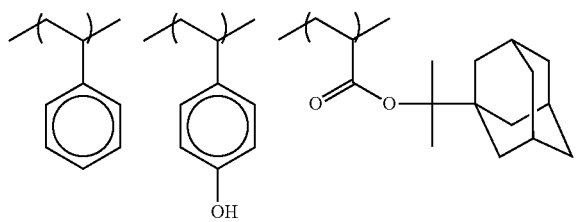

(R-14)

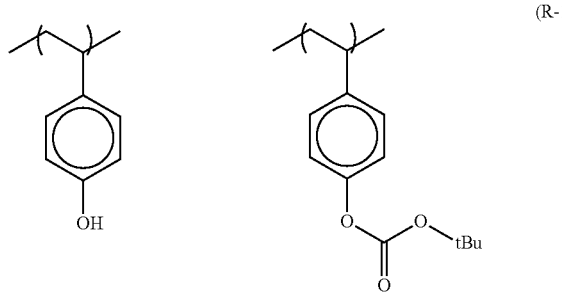

(R-15)

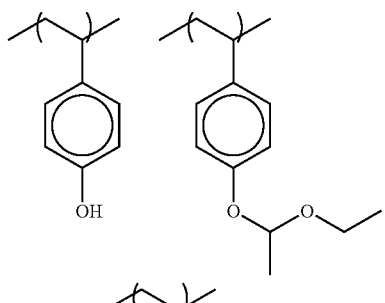

(R-16)

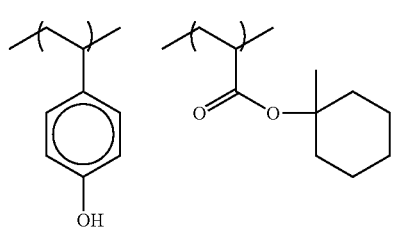

(R-17)

In the above specific examples, tBu means a t-butyl group.

The content of an acid-decomposable group is expressed by B/(B+S), taking the number of the acid-decomposable groups in a resin as (B), and the number of alkali-soluble groups not protected with acid-eliminable groups as (S). The content is preferably from 0.01 to 0.7, more preferably from 0.05 to 0.50, and still more preferably from 0.05 to 0.40.

When the positive photosensitive composition in the invention is irradiated with ArF excimer laser beams, it is preferred that the resin of component (B) is a resin having a monocyclic or polycyclic alicyclic hydrocarbon structure and capable of decomposing by the action of an acid to thereby increase the solubility in an alkali developing solution.

As a resin having a monocyclic or polycyclic alicyclic hydrocarbon structure and capable of decomposing by the action of an acid to thereby increase the solubility in an alkali developing solution (hereinafter also referred to as "an alicyclic hydrocarbon acid-decomposable resin"), a resin containing at least one repeating unit selected from the group consisting of a repeating unit having a partial structure containing alicyclic hydrocarbon represented by any of the following formulae (pI) to (pV), and a repeating unit represented by the following formula (II-AB) is preferred.

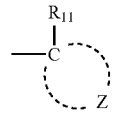

(pI)

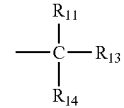

(pII)

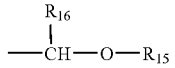

(pIII)

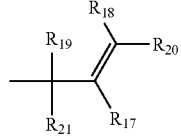

(pIV)

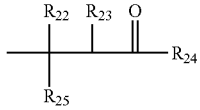

(pV)

In formulae (pI) to (pV), $R_{11}$ represents a methyl group, an ethyl group, an n-propyl group, an isopropyl group, an n-butyl group, an isobutyl group, or a sec-butyl group; and Z represents an atomic group necessary to form a cycloalkyl group together with a carbon atom.

$R_{12}$, $R_{13}$, $R_{14}$, $R_{15}$ and $R_{16}$ each independently represents a straight chain or branched alkyl group or a cycloalkyl group each having from 1 to 4 carbon atoms, provided that at least one of $R_{12}$ to $R_{14}$, or either $R_{15}$ or $R_{16}$ represents a cycloalkyl group.

$R_{17}$, $R_{18}$, $R_{19}$, $R_{20}$ and $R_{21}$ each independently represents a hydrogen atom, a straight chain or branched alkyl group or a cycloalkyl group each having from 1 to 4 carbon atoms, provided that at least one of $R_{17}$ to $R_{21}$ represents a cycloalkyl group, and either $R_{19}$ or $R_{21}$ represents a straight chain or branched alkyl group or a cycloalkyl group each having from 1 to 4 carbon atoms.

$R_{22}$, $R_{23}$, $R_{24}$ and $R_{25}$ each independently represents a hydrogen atom, a straight chain or branched alkyl group or a cycloalkyl group each having from 1 to 4 carbon atoms, provided that at least one of $R_{22}$ to $R_{25}$ represents a cycloalkyl group, and $R_{23}$ and $R_{24}$ may be bonded to each other to form a ring.

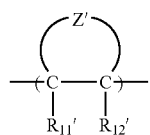
(II-AB)

In formula (II-AB), $R_{11}'$ and $R_{12}'$ each independently represents a hydrogen atom, a cyano group, a halogen atom, or an alkyl group.

Z' contains bonded two carbon atoms (C—C) and represents an atomic group to form an alicyclic structure.

Formula (II-AB) is more preferably represented by the following formula (II-AB1) or (II-AB2).

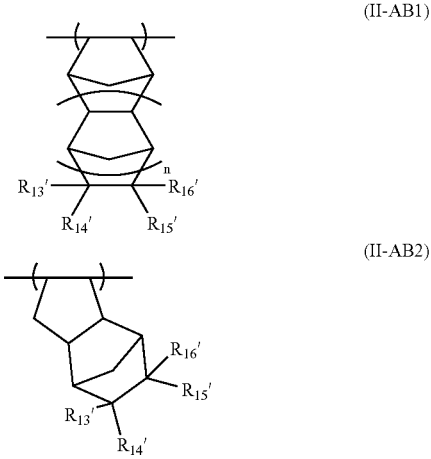

In formulae (II-AB1) and (II-AB2), $R_{13}'$, $R_{14}'$, $R_{15}'$ and $R_{16}'$ each independently represents a hydrogen atom, a halogen atom, a cyano group, a hydroxyl group, —COOH, —COOR$_5$, a group decomposable by the action of an acid, —C(=O)—X-A'-R$_{17}'$, an alkyl group, or a cycloalkyl group. At least two of $R_{13}'$ to $R_{16}'$ may be bonded to form a ring.

$R_5$ represents an alkyl group, a cycloalkyl group, or a group having a lactone structure.

X represents an oxygen atom, a sulfur atom, —NH—, —NHSO$_2$— or —NHSO$_2$NH—.

A' represents a single bond or a divalent linking group.

$R_{17}'$ represents —COOH, —COOR$_5$, —CN, a hydroxyl group, an alkoxyl group, —CO—NH—R$_6$, —CO—NH—SO$_2$—R$_6$, or a group having a lactone structure.

$R_6$ represents an alkyl group or a cycloalkyl group.

n represents 0 or 1.

The alkyl group represented by $R_{12}$ to $R_{25}$ in formulae (pI) to (pV) is a straight chain or branched alkyl group having from 1 to 4 carbon atoms, e.g., a methyl group, an ethyl group, a propyl group, an n-butyl group, a sec-butyl group, and a t-butyl group are exemplified.

The cycloalkyl group represented by $R_{11}$ to $R_{25}$ or the cycloalkyl group formed by Z and carbon atoms may be monocyclic or polycyclic. Specifically, groups having a monocyclic, bicyclic, tricyclic or tetracyclic structure having 5 or more carbon atoms can be exemplified. The number of carbon atoms of the groups is preferably from 6 to 30, and especially preferably from 7 to 25. These cycloalkyl groups may have a substituent.

As preferred cycloalkyl groups, an adamantyl group, a noradamantyl group, a decalin residue, a tricyclodecanyl group, a tetracyclododecanyl group, a norbornyl group, a cedrol group, a cyclopentyl group, a cyclohexyl group, a cycloheptyl group, a cyclooctyl group, a cyclodecanyl group, and a cyclododecanyl group can be exemplified. More preferred cycloalkyl groups are an adamantyl group, a norbornyl group, a cyclohexyl group, a cyclopentyl group, a tetracyclododecanyl group, and a tricyclodecanyl group.

These alkyl groups and cycloalkyl groups may further have a substituent. As further substituents of the alkyl groups and cycloalkyl groups, an alkyl group (having from 1 to 4 carbon atoms), a halogen atom, a hydroxyl group, an alkoxyl group (having from 1 to 4 carbon atoms), a carboxyl group, and an alkoxycarbonyl group (having from 2 to 6 carbon atoms) can be exemplified. These alkyl group, alkoxyl group and alkoxycarbonyl group may further have a substituent. As the substituents that these alkyl group, alkoxyl group and alkoxycarbonyl group may further have, a hydroxyl group, a halogen atom and an alkoxyl group are exemplified.

The structures represented by formulae (pI) to (pV) in the resin can be used for the protection of alkali-soluble groups. As the alkali-soluble groups, various groups well known in this technical field can be exemplified.

Specifically, the structures in which the hydrogen atoms of carboxylic acid group, a sulfonic acid group, a phenol group and a thiol group are substituted with the structures represented by formulae (pI) to (pV) are exemplified, and preferably the structures in which the hydrogen atoms of carboxylic acid group and a sulfonic acid group are substituted with the structures represented by formulae (pI) to (pV) are exemplified.

As the repeating unit having the alkali-soluble group protected with the structure represented by any of the above formulae (pI) to (pV), a repeating unit represented by the following formula (pA) is preferred.

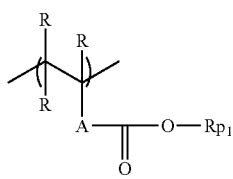
(pA)

In formula (pA), R represents a hydrogen atom, a halogen atom, or a straight chain or branched alkyl group having from 1 to 4 carbon atoms, and a plurality of R's may be the same or different.

A represents a single group or the combination of two or more groups selected from the group consisting of a single bond, an alkylene group, an ether group, a thioether group, a carbonyl group, an ester group, an amido group, a sulfonamido group, a urethane group, and a urea group. A single bond is preferred.

$R_{p1}$ represents a group represented by any of formulae (pI) to (pVI).

The repeating unit represented by (pA) is most preferably a repeating unit by 2-alkyl-2-adamantyl(meth)acrylate and dialkyl(1-adamantyl)methyl(meth)acrylate.

The specific examples of the repeating units represented by formula (pA) are shown below, but the invention is not restricted thereto.

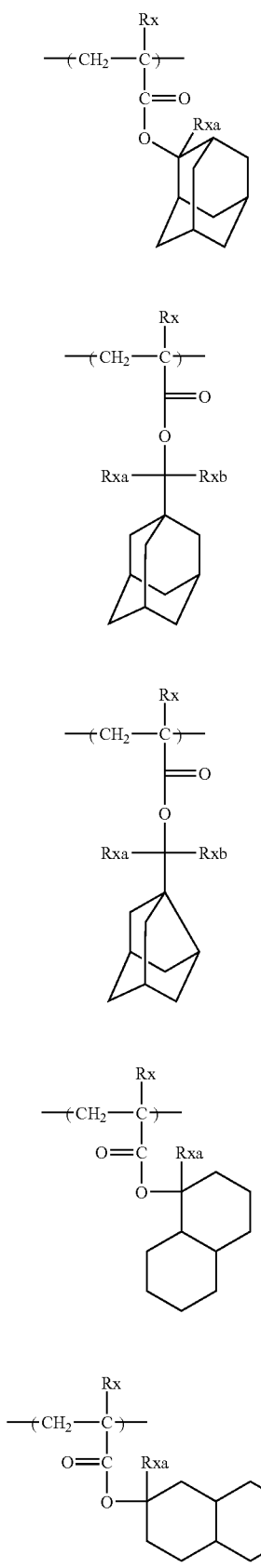
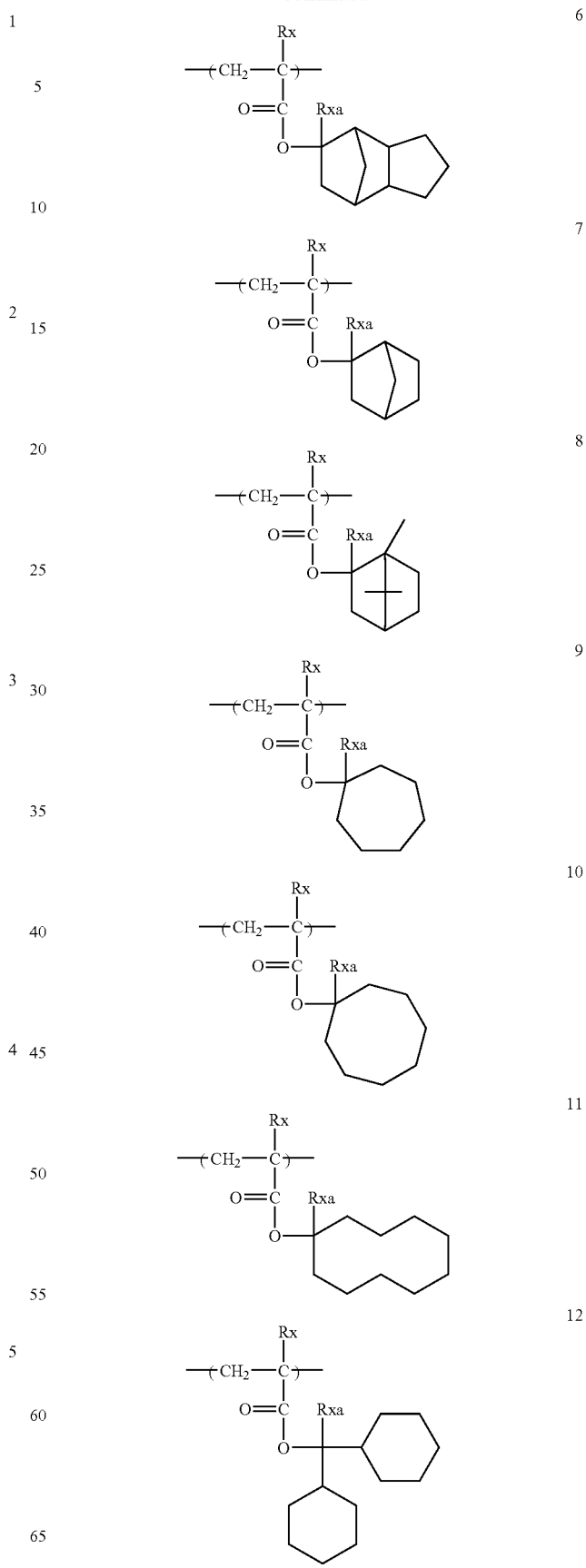

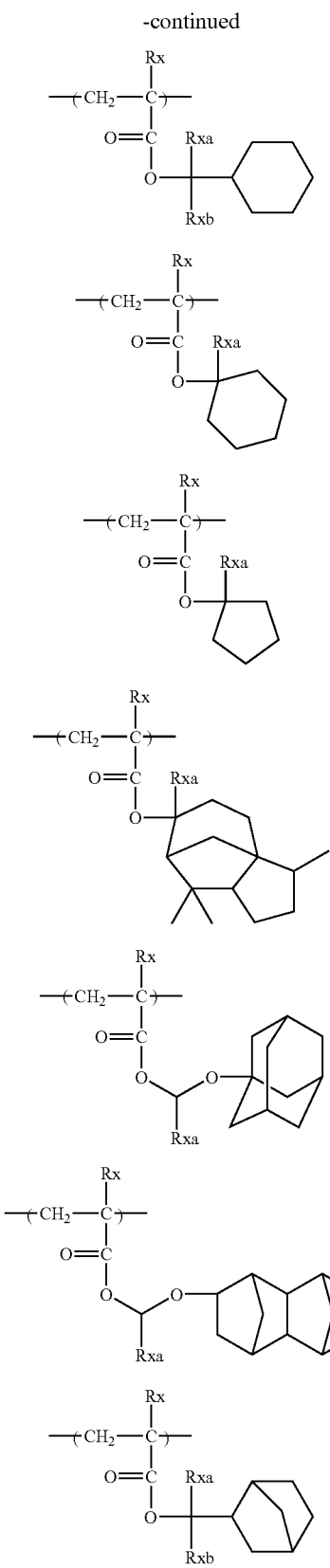

In each of the above structural formulae, Rx represents H, CH$_3$, CF$_3$ or CH$_2$OH; Rxa and Rxb each independently represents an alkyl group having from 1 to 4 carbon atoms.

As the halogen atoms represented by R$_{11}$' and R$_{12}$' in formula (II-AB), a chlorine atom, a bromine atom, a fluorine atom and an iodine atom are exemplified.

As the alkyl group represented by R$_{11}$' and R$_{12}$', a straight chain or branched alkyl group having from 1 to 10 carbon atoms is preferred, e.g., a methyl group, an ethyl group, an n-propyl group, an isopropyl group, a straight chain or branched butyl group, pentyl group, hexyl group and heptyl group are exemplified.

The atomic group represented by Z' to form an alicyclic structure is an atomic group to form a repeating unit having an alicyclic hydrocarbon structure in the resin, which may have a substituent, and an atomic group to form a repeating unit having a bridged alicyclic hydrocarbon structure is especially preferred.

As the skeleton of the alicyclic hydrocarbon formed, the same cycloalkyl groups as the cycloalkyl groups represented by R$_{12}$ to R$_{25}$ in formulae (pI) to (pV) are exemplified.

The skeleton of the alicyclic hydrocarbon structure may have a substituent, and as the substituents, the groups represented by R$_{13}$' to R$_{16}$' in formula (II -AB1) or (II-AB2) can be exemplified.

In the alicyclic hydrocarbon-based acid-decomposable resin in the invention, a group capable of decomposing by the action of an acid can be contained in at least one repeating unit of a repeating unit having a partial structure containing alicyclic hydrocarbon represented by any of formulae (pI) to (pV), a repeating unit represented by formula (II-AB), and a repeating unit of the later-described copolymer component.

Various substituents of R$_{13}$' to R$_{16}$' in formula (II-AB1) or (II -AB2) can also be the substituents of the atomic group to form an alicyclic hydrocarbon structure in formula (II-AB), or of the atomic group Z to form a bridged alicyclic hydrocarbon structure.

The specific examples of the repeating units represented by formula (II-AB1) or (II-AB2) are shown below, but the invention is not restricted thereto.

[II-1]
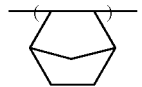

[II-2]
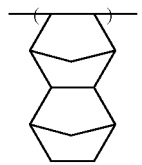

[II-3]
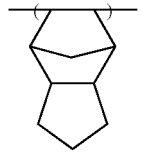

[II-4]
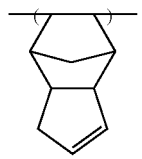

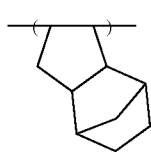 [II-5]
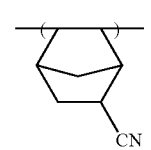 [II-6]
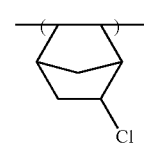 [II-7]
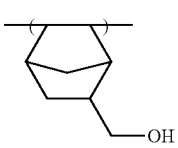 [II-8]
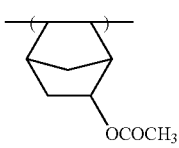 [II-9]
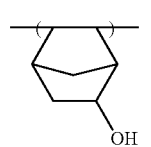 [II-10]
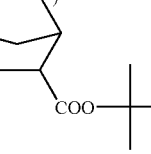 [II-11]
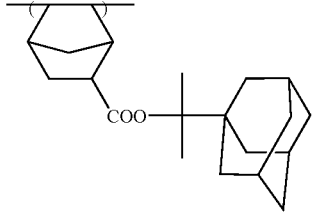 [II-12]
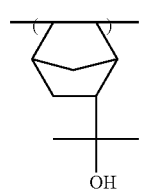 [II-13]
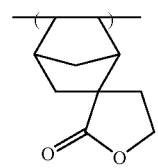 [II-14]
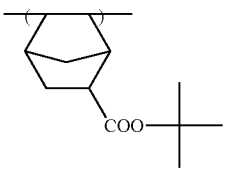 [II-15]
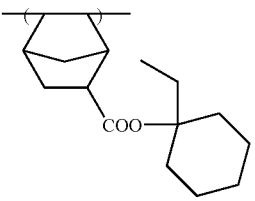 [II-16]
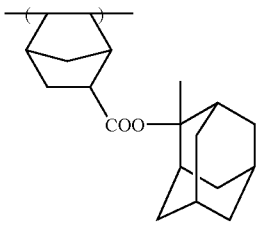 [II-17]
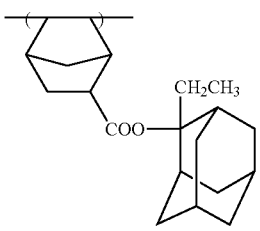 [II-18]
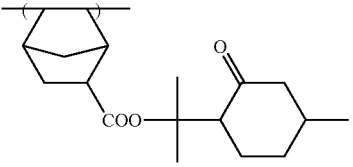 [II-19]
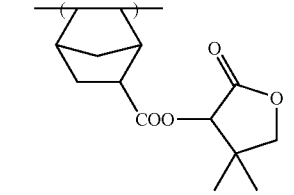 [II-20]
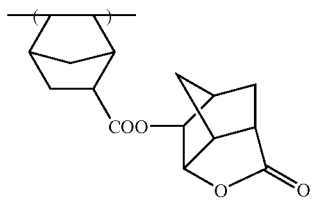 [II-21]

[II-22] 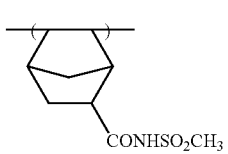

[II-23] 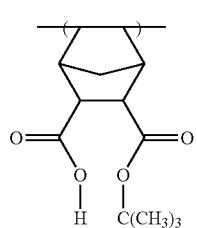

[II-24] 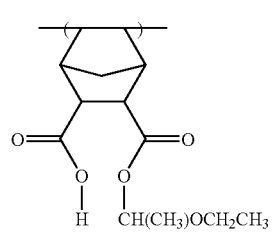

[II-25] 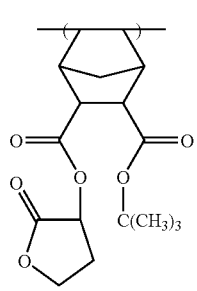

[II-26] 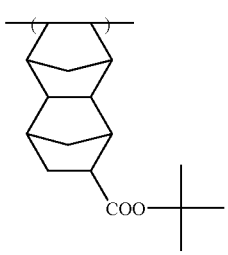

[II-27] 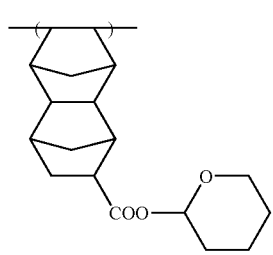

[II-28] 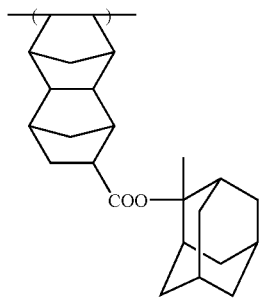

[II-29] 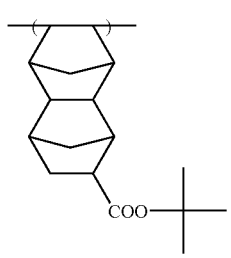

[II-30] 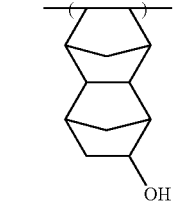

[II-31] 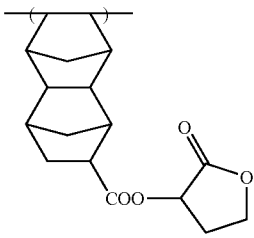

[II-32] 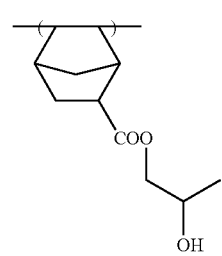

It is preferred for the alicyclic hydrocarbon-based acid-decomposable resin in the invention to contain a repeating unit having a lactone group. As the lactone group, any group having a lactone structure can be used, but preferably groups having a 5-to 7-membered ring lactone structure, e.g., 5- to 7-membered ring lactone structures condensed with other ring structures in the form of forming a bicyclo structure or a spiro structure are preferred. It is more preferred for the alicyclic hydrocarbon-based acid-decomposable resin in the invention to contain a repeating unit having a group having a lactone structure represented by any of the following formulae (LC1-1) to (LC1-16). A group having a lactone structure may be directly bonded to the main chain of the repeating unit. Preferred lactone structures are (LC1-1), (LC1-4) (LC1-

5), (LC1-6), (LC1-13) and (LC1-14). By the use of a specific lactone structure, line edge roughness and development defect are bettered.
LC1-1
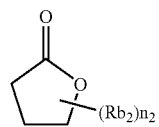
LC1-2
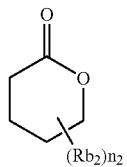
LC1-3
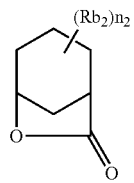
LC1-4
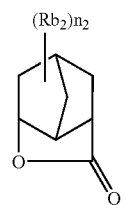
LC1-5
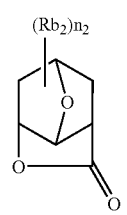
LC1-6
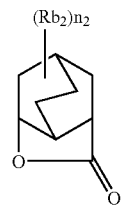
LC1-7
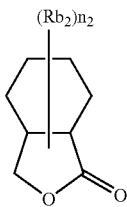
LC1-8
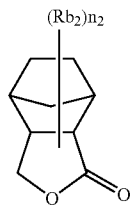
LC1-9
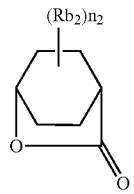
LC1-10
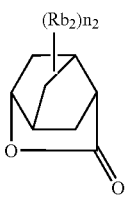
LC1-11
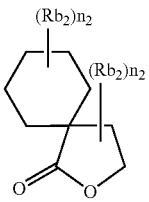
LC1-12
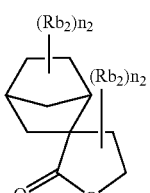
LC1-13
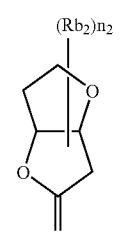
LC1-14
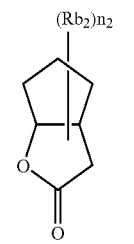

LC1-15

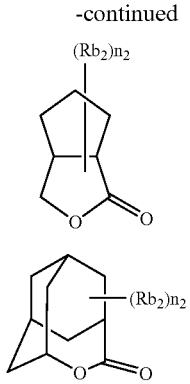

LC1-16

The lactone structure moiety may have or may not have a substituent (Rb$_2$). As preferred substituent (Rb$_2$), an alkyl group having from 1 to 8 carbon atoms, a cycloalkyl group having from 3 to 7 carbon atoms, an alkoxyl group having from 1 to 8 carbon atoms, an alkoxycarbonyl group having from 1 to 8 carbon atoms, a carboxyl group, a halogen atom, a hydroxyl group, a cyano group, and an acid-decomposable group are exemplified. n$_2$ represents an integer of from 0 to 4. When n$_2$ is an integer of 2 or more, a plurality of Rb$_2$ may be the same or different, and a plurality of Rb$_2$ may be bonded to each other to form a ring.

As the repeating units having a group having a lactone structure represented by any of formulae (LC1-1) to (LC1-16), a repeating unit represented by formula (II-AB1) or (II-AB2) in which at least one of R$_{13}$' to R$_{16}$' is a group having a lactone structure represented by any of formulae (LC1-1) to (LC1-16) (for example, R$_5$ of —COOR$_5$ is a group represented by any of formulae (LC1-1) to (LC1-16)), or a repeating unit represented by the following formula (AI) can be exemplified.

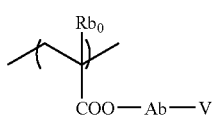

(AI)

In formula (AI), Rb$_0$ represents a hydrogen atom, a halogen atom, or an alkyl group having from 1 to 4 carbon atoms.

As the alkyl group represented by Rb$_0$, e.g., a methyl group, an ethyl group, a propyl group, an n-butyl group, a sec-butyl group, a t-butyl group, etc., can be exemplified. The alkyl group represented by Rb$_0$ may have a substituent. As the preferred substituents that the alkyl group represented by Rb$_0$ may have, e.g., a hydroxyl group and a halogen atom are exemplified.

As the halogen atom represented by Rb$_0$, a fluorine atom, a chlorine atom, a bromine atom and an iodine atom can be exemplified. Rb$_0$ preferably represents a hydrogen atom or a methyl group.

Ab represents an alkylene group, a divalent linking group having a monocyclic or polycyclic alicyclic hydrocarbon structure, a single bond, an ether group, an ester group, a carbonyl group, a carboxyl group, or a divalent linking group combining these groups. Ab preferably represents a single bond or a linking group represented by -Ab$_1$-CO$_2$—.

Ab$_1$ represents a straight chain or branched alkylene group, or a monocyclic or polycyclic cycloalkylene group, and preferably a methylene group, an ethylene group, a cyclohexyl residue, an adamantyl residue, or a norbornyl residue.

V represents a group represented by any of formulae (LC1-1) to (LC1-16).

Repeating units having a lactone structure generally have optical isomers, and any optical isomer may be used. One kind of optical isomer may be used alone, or a plurality of optical isomers may be used as mixture. When one kind of optical isomer is mainly used, the optical purity (ee) of the optical isomer is preferably 90 or more, and more preferably 95 or more.

The specific examples of the repeating units having a group having a lactone structure are shown below, but the invention is not limited thereto.

(In the formulae, Rx represents H, CH$_3$, CH$_2$OH or CF$_3$.)

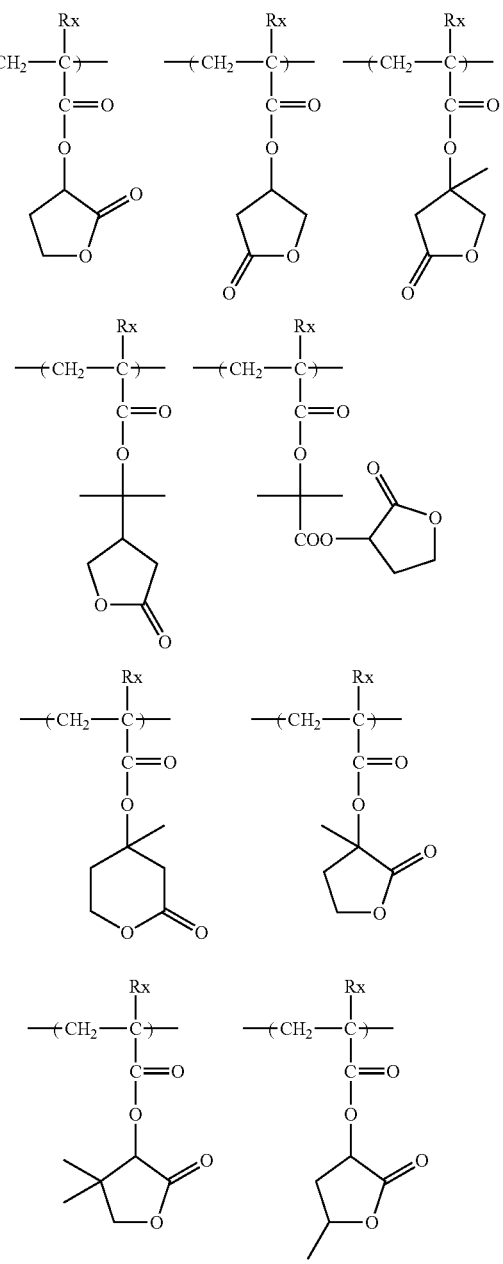

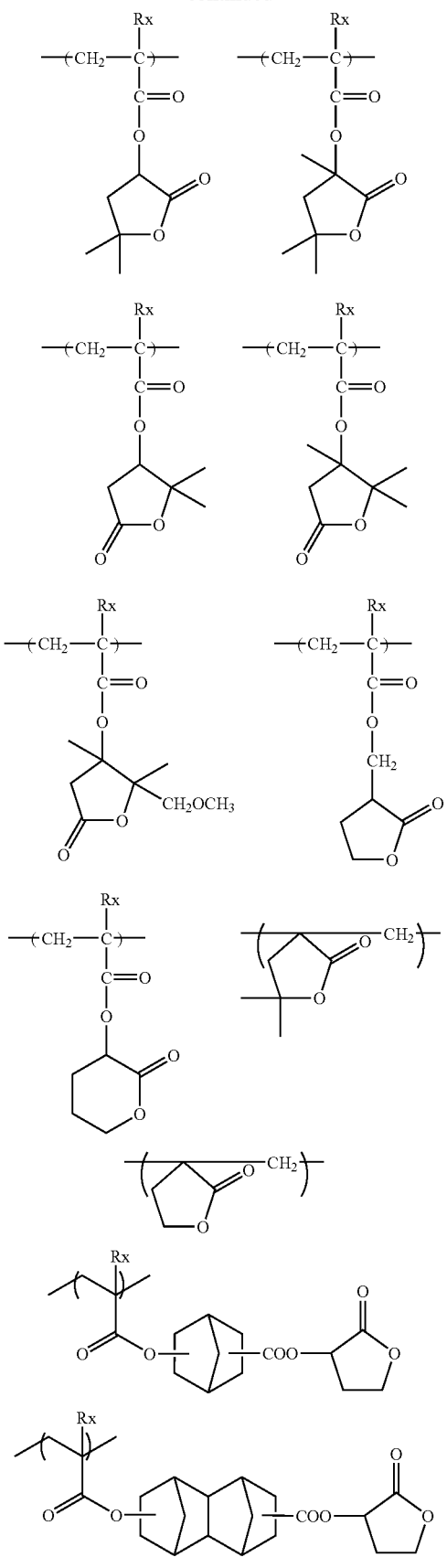
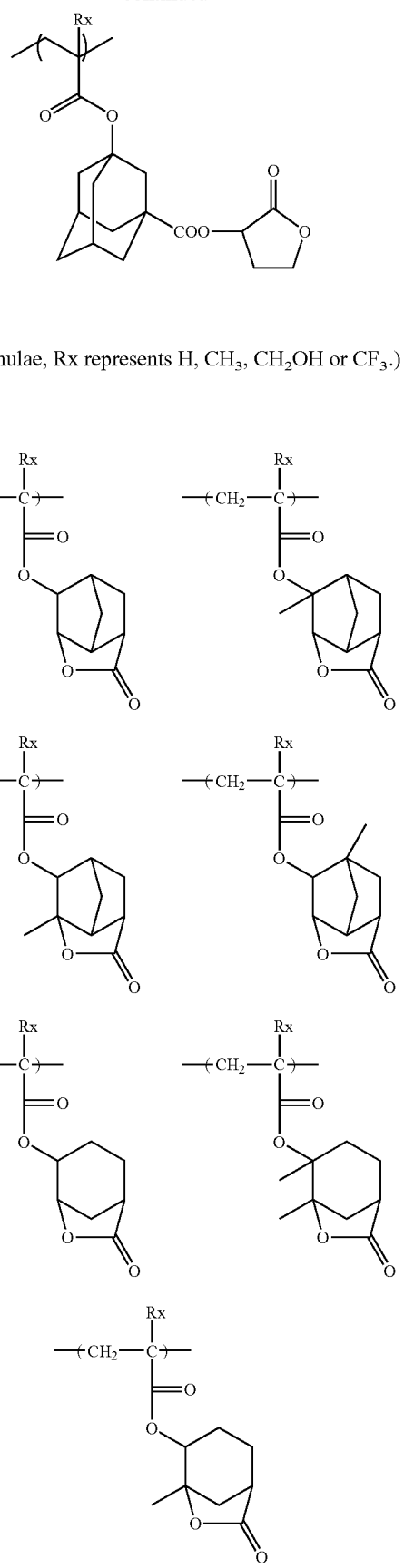
(In the formulae, Rx represents H, CH$_3$, CH$_2$OH or CF$_3$.)

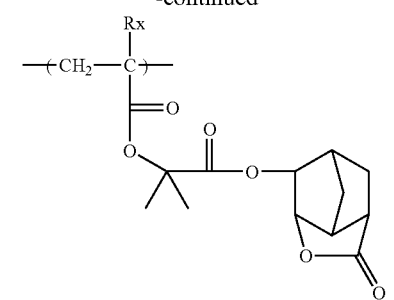
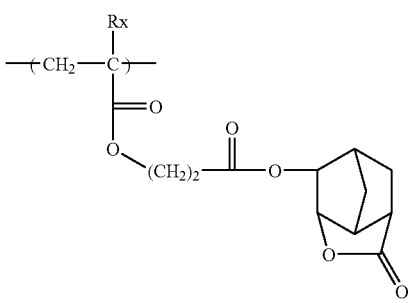
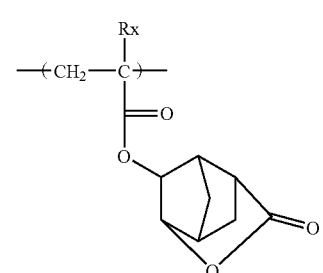
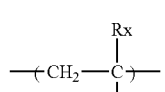 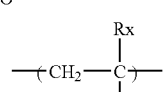
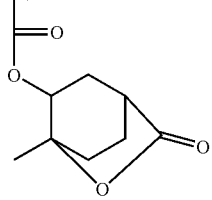
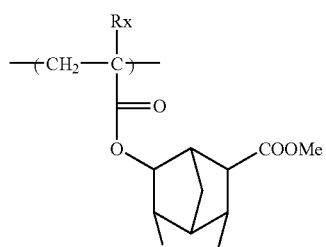
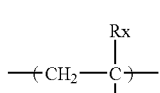
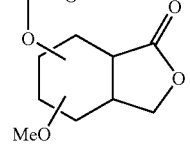
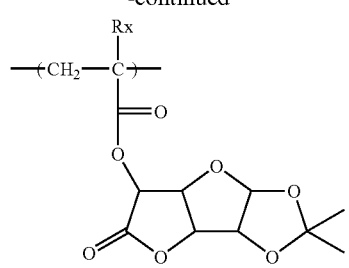
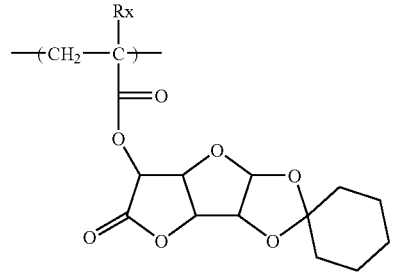
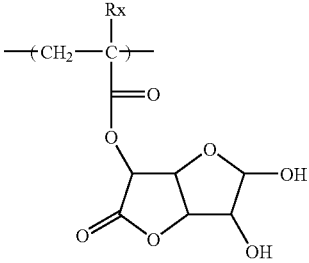
(In the formulae, Rx represents H, CH$_3$, CH$_2$OH or CF$_3$.)
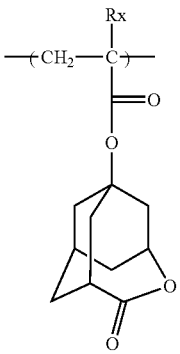 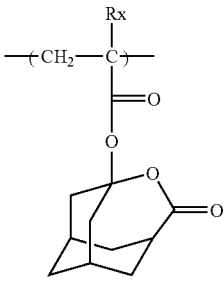
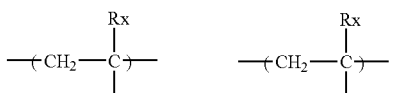
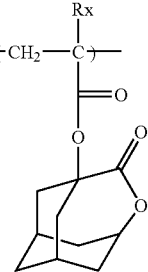 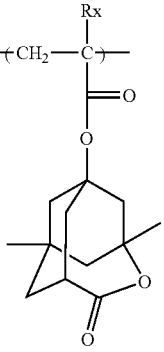

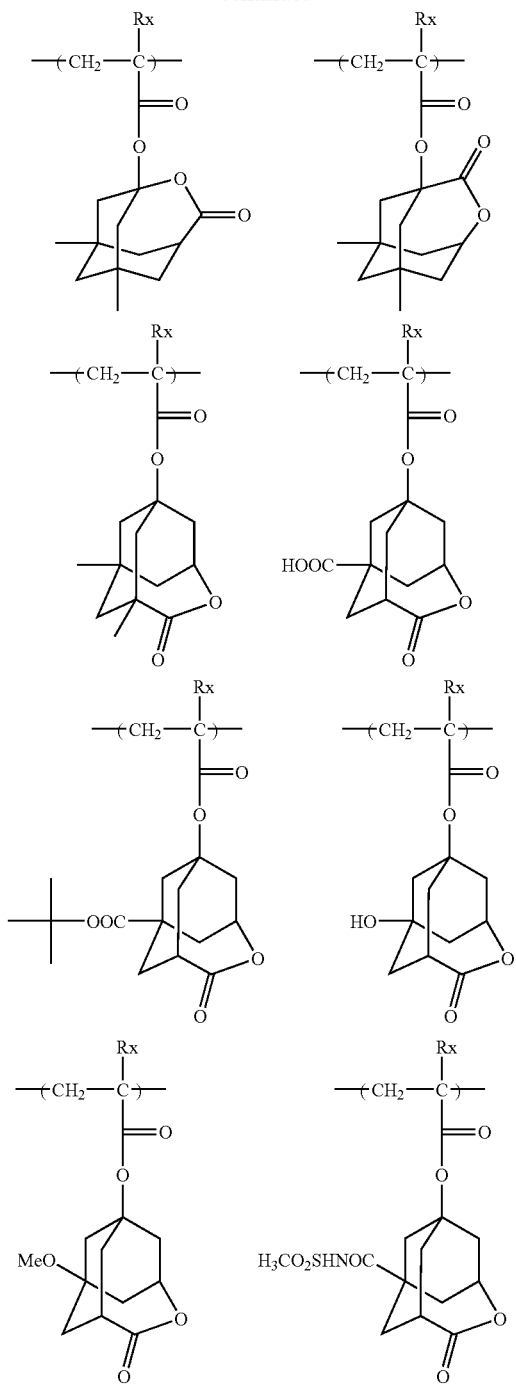

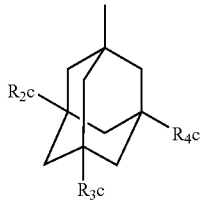

(VIIa)

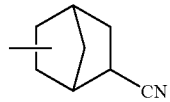

(VIIb)

In formula (VIIa), $R_{2c}$, $R_{3c}$ and $R_{4c}$ each independently represents a hydrogen atom, a hydroxyl group, or a cyano group, provided that at least one of $R_{2c}$, $R_{3c}$ and $R_{4c}$ represents a hydroxyl group or a cyano group. Preferably one or two of $R_{2c}$, $R_{3c}$ and $R_{4c}$ represent a hydroxyl group and the remainder represents a hydrogen atom. More preferably two of $R_{2c}$, $R_{3c}$ and $R_{4c}$ represent a hydroxyl group and the remainder represents a hydrogen atom.

The group represented by formula (VIIa) is preferably dihydroxy or monohydroxy, and more preferably dihydroxy.

As the repeating unit having the group represented by formula (VIIa) or (VIIb), a repeating unit represented by formula (II-AB1) or (II-AB2) in which at least one of $R_{13}'$ to $R_{16}'$ is a group having a structure represented by formula (VIIa) or (VIIb) (for example, $R_5$ of —$COOR_5$ is a group represented by formula (VIIa) or (VIIb)), or a repeating unit represented by the following formula (AIIa) or (AIIb) can be exemplified.

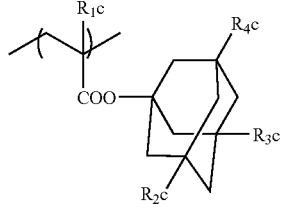

(AIIa)

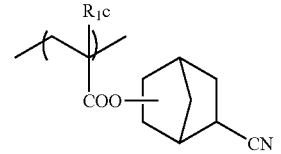

(AIIb)

It is preferred for the alicyclic hydrocarbon-based acid-decomposable resin in the invention to have a repeating unit having an alicyclic hydrocarbon structure substituted with a polar group, by which adhesion with a substrate and affinity with a developing solution are improved. As the polar group, a hydroxyl group and a cyano group are preferred.

The hydroxyl group as the polar group forms an alcoholic hydroxyl group.

As the alicyclic hydrocarbon structure substituted with a polar group, structures represented by the following formula (VIIa) or (VIIb) are preferred.

In formulae (AIIa) and (AIId), ), $R_{1c}$ represents a hydrogen atom, a methyl group, a trifluoromethyl group, or a hydroxymethyl group.

$R_{2c}$, $R_{3c}$ and $R_{4c}$ each has the same meaning as $R_{2c}$, $R_{3c}$ and $R_{4c}$ in formula (VIIa).

The specific examples of the repeating units having an alicyclic hydrocarbon structure substituted with a polar group represented by formulae (AIIa) to (AIId) are shown below, but the invention is not restricted thereto.

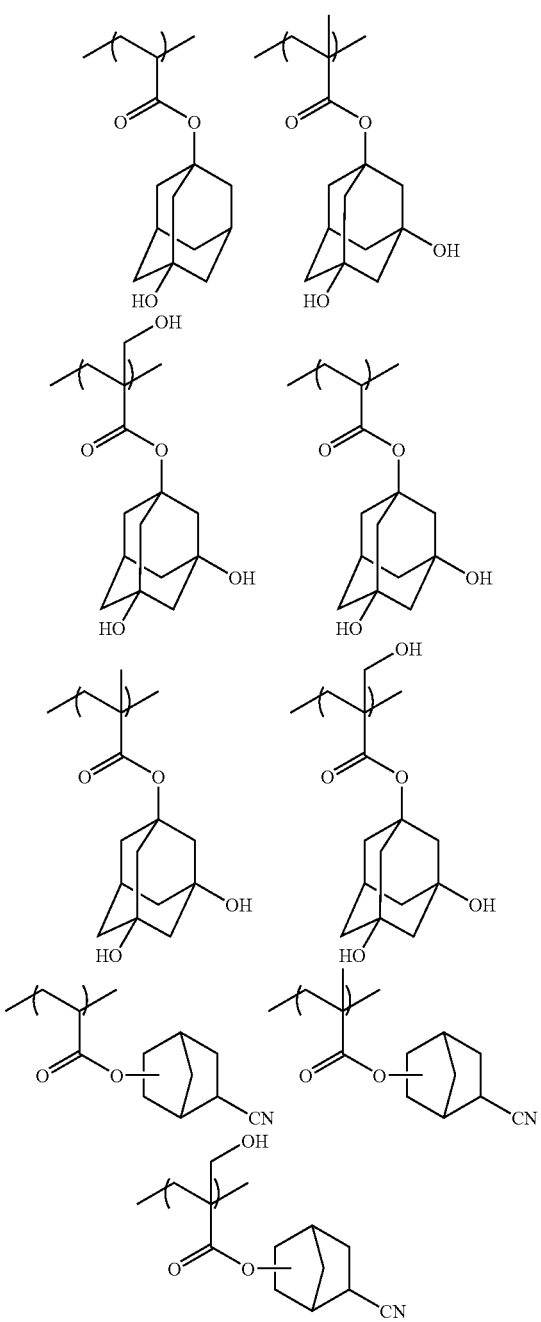

The alicyclic hydrocarbon-based acid-decomposable resin in the invention may have a repeating unit represented by the following formula (VIII).

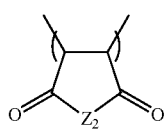
(VIII)

In formula (VIII), $Z_2$ represents —O— or —N($R_{41}$)—. $R_{41}$ represents a hydrogen atom, a hydroxyl group, an alkyl group, or —OSO$_2$—$R_{42}$. $R_{42}$ represents an alkyl group, a cycloalkyl group, or a camphor residue. The alkyl group represented by $R_{41}$ and $R_{42}$ may be substituted with a halogen atom (preferably a fluorine atom) and the like.

As the specific examples of the repeating units represented by formula (VIII), the following compounds are exemplified, but the invention is not restricted thereto.

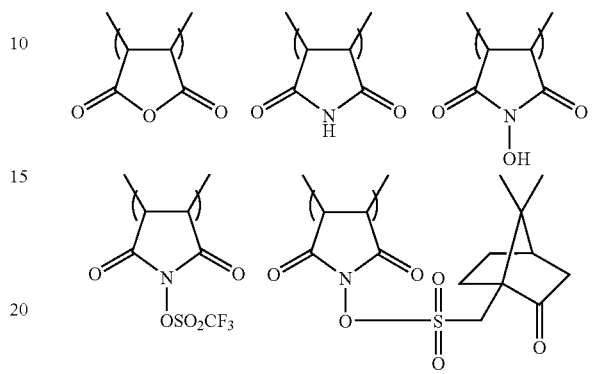

It is preferred for the alicyclic hydrocarbon-based acid-decomposable resin in the invention to have a repeating unit having an alkali-soluble group, and it is more preferred to have a repeating unit having a carboxyl group, by which the resolution in the use for contact hole is enhanced. As the repeating units having a carboxyl group, both a repeating unit having a carboxyl group directly bonded to the main chain of a resin such as a repeating unit by acrylic acid or methacrylic acid, and a repeating unit having a carboxyl group bonded to the main chain of a resin via a linking group are preferred, and the linking group may have a monocyclic or polycyclic hydrocarbon structure. The repeating unit by acrylic acid or methacrylic acid is most preferred.

The alicyclic hydrocarbon-based acid-decomposable resin in the invention may have a repeating unit having one to three groups represented by the following formula (F1), by which line edge roughness property is improved.

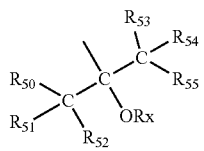
(F1)

In formula (F1), $R_{50}$, $R_{51}$, $R_{52}$, $R_{53}$, $R_{54}$ and $R_{55}$ each independently represents a hydrogen atom, a fluorine atom, or an alkyl group, provided that at least one of $R_{50}$ to $R_{55}$ represents a fluorine atom, or an alkyl group in which at least one hydrogen atom is substituted with a fluorine atom.

Rx represents a hydrogen atom or an organic group (preferably an acid-decomposable protective group, an alkyl group, a cycloalkyl group, an acyl group, or an alkoxycarbonyl group).

The alkyl group represented by $R_{50}$ to $R_{55}$ may be substituted with a halogen atom, e.g., a fluorine atom, or a cyano group, and preferably an alkyl group having from 1 to 3 carbon atoms, e.g., a methyl group and a trifluoromethyl group can be exemplified.

It is preferred that all of $R_{50}$ to $R_{55}$ represent a fluorine atom.

As the organic group represented by Rx, an acid-decomposable protective group, and an alkyl group, a cycloalkyl group, an acyl group, an alkylcarbonyl group, an alkoxycarbonyl group, an alkoxycarbonylmethyl group, an alkoxymethyl group, and a 1-alkoxyethyl group, each of which may have a substituent, are preferred.

The repeating unit having the group represented by formula (F1) is preferably a repeating unit represented by the following formula (F2).

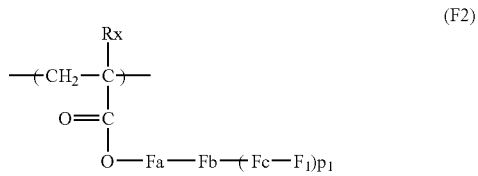

In formula (F2), Rx represents a hydrogen atom, a halogen atom, or an alkyl group having from 1 to 4 carbon atoms. As preferred substituents that the alkyl group represented by Rx may have, a hydroxyl group and a halogen atom are exemplified.

Fa represents a single bond or a straight chain or branched alkylene group, and preferably a single bond.

Fb represents a monocyclic or polycyclic hydrocarbon group.

Fc represents a single bond or a straight chain or branched alkylene group, and preferably a single bond or a methylene group.

$F_1$ represents a group represented by formula (F1).

$p_1$ represents from 1 to 3.

As the cyclic hydrocarbon group represented by Fb, a cyclopentyl group, a cyclohexyl group, or a norbornyl group is preferred.

The specific examples of the repeating units having the structure represented by formula (F1) are shown below.

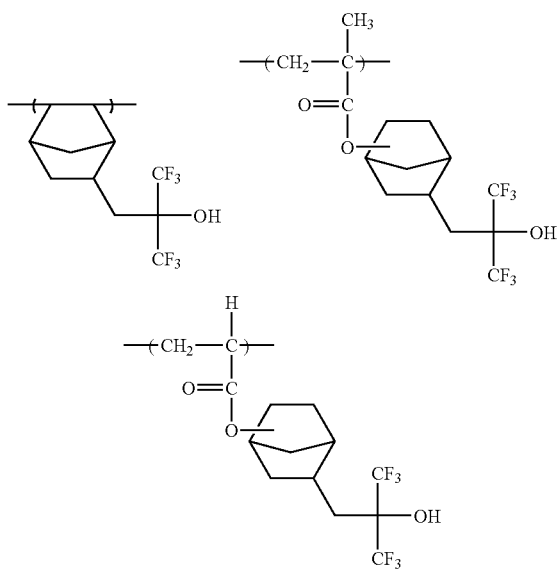

The alicyclic hydrocarbon-based acid-decomposable resin in the invention can contain various kinds of repeating structural units, besides the above repeating structural units, for the purpose of the adjustments of dry etching resistance, aptitude for standard developing solutions, adhesion to a substrate, resist profile, and further, general requisite characteristics of resists, e.g., resolution, heat resistance and sensitivity.

As these repeating structural units, the repeating structural units corresponding to the monomers shown below can be exemplified, but the invention is not restricted thereto.

By containing such various repeating structural units, fine adjustment of performances required of the alicyclic hydrocarbon-based acid-decomposable resin, in particular the following performances, becomes possible, that is, (1) Solubility in a coating solvent,
(2) A film-forming property (a glass transition point),
(3) Alkali developability,
(4) Decrease of layer thickness (hydrophobic-hydrophilic property, selection of an alkali-soluble group),
(5) Adhesion of an unexposed area to a substrate, and
(6) Dry etching resistance.

The examples of such monomers include compounds having one addition polymerizable unsaturated bond selected from acrylic esters, methacrylic esters, acrylamides, methacryl-amides, allyl compounds, vinyl ethers, vinyl esters, etc.

In addition to the aforementioned compounds, addition polymerizable unsaturated compounds copolymerizable with the monomers corresponding to the above various repeating structural units may be used for copolymerization.

In the alicyclic hydrocarbon-based acid-decomposable resin, the molar ratio of the content of each repeating structural unit is arbitrarily set to adjust dry etching resistance and aptitude for standard developing solutions of a resist, adhesion to a substrate, and resist profile, in addition, general requisite characteristics of a resist, e.g., resolution, heat resistance and sensitivity.

As preferred embodiments of the alicyclic hydrocarbon-based acid-decomposable resin in the invention, the following resins are exemplified.

(1) A resin containing a repeating unit having a partial structure containing the alicyclic hydrocarbon represented by any of formulae (pI) to (pV) (a side chain type), preferably a resin containing a (meth)acrylate repeating unit having the structure of any of formulae (pI) to (pV);

(2) A resin containing a repeating unit represented by formula (II-AB) (a main chain type); however, the following is further exemplified as embodiment (2):

(3) A resin containing a repeating unit represented by formula (II-AB), a maleic anhydride derivative and a (meth)acrylate structure (a hybrid type).

In the alicyclic hydrocarbon-based acid-decomposable resin, the content of a repeating unit having an acid-decomposable group is preferably from 10 to 60 mol % in the total repeating structural units, more preferably from 20 to 50 mol %, and still more preferably from 25 to 40 mol %.

In the alicyclic hydrocarbon-based acid-decomposable resin, the content of the repeating unit having a partial structure containing the alicyclic hydrocarbon represented by any of formulae (pI) to (pV) is preferably from 25 to 70 mol % in all the repeating structural units, more preferably from 35 to 65 mol %, and still more preferably from 40 to 60 mol %.

In the alicyclic hydrocarbon-based acid-decomposable resin, the content of the repeating unit represented by formula (II-AB) is preferably from 10 to 60 mol % in all the repeating structural units, more preferably from 15 to 55 mol %, and still more preferably from 20 to 50 mol %.

The content of the repeating unit having a lactone group is preferably from 10 to 70 mol % in all the repeating structural units, more preferably from 20 to 60 mol %, and still more preferably from 25 to 60 mol %.

The content of the repeating unit having the alicyclic hydrocarbon structure substituted with a polar group is preferably from 1 to 40 mol % in all the repeating structural units, more preferably from 5 to 30 mol %, and still more preferably from 5 to 20 mol %.

The content of the repeating structural units on the basis of the monomers of further copolymerization components in the resin can also be optionally set according to the desired resist performances, and the content is generally preferably 99 mol % or less to the total mol number of the repeating structural units having a partial structure containing the alicyclic hydrocarbon represented by any of formulae (pI) to (pV) and the repeating units represented by formula (II-AB), more preferably 90 mol % or less, and still more preferably 80 mol % or less.

When the composition in the invention is used for ArF exposure, it is preferred that the resin does not have an aromatic group from the aspect of the transparency to ArF rays.

The alicyclic hydrocarbon-based acid-decomposable resin for use in the invention is preferably such that all the repeating units consist of (meth)acrylate repeating units. In this case, any of the following cases can be used, that is, a case where all the repeating units consist of methacrylate, a case where all the repeating units consist of acrylate, and a case where the repeating units consist of mixture of methacrylate and acrylate, but it is preferred that acrylate repeating units account for 50 mol % or less of all the repeating units.

More preferred resins are terpolymers comprising from 25 to 50 mol % of the repeating unit having a partial structure containing the alicyclic hydrocarbon represented by any of formulae (pI) to (pV), from 25 to 50 mol % of the repeating unit having the lactone structure, and from 5 to 30 mol % of the repeating unit having the alicyclic hydrocarbon structure substituted with the polar group, and tetrapolymers further containing from 5 to 20 mol % of the repeating units having a carboxyl group or the structure represented by formula (F1).

The alicyclic hydrocarbon-based acid-decomposable resins for use in the invention can be synthesized according to ordinary methods (e.g., radical polymerization). For instance, as ordinary methods, a batch polymerization method of dissolving a monomer and an initiator in a solvent and heating the solution to perform polymerization, and a dropping polymerization method of adding a solution of a monomer and an initiator to a heated solvent over 1 to 10 hours by dropping are exemplified, and dropping polymerization is preferred. As reaction solvents, ethers, e.g., tetrahydrofuran, 1,4-dioxane, and diisopropyl ether, ketones, e.g., methyl ethyl ketone and methyl isobutyl ketone, an ester solvent, e.g., ethyl acetate, amide solvents, e.g., dimethylformamide and dimethyacetamide, and the later-described solvents capable of dissolving the composition of the invention, e.g., propyelne glycol monomethyl ether acetate, propylene glycol monomethyl ether, and cyclohexanone are exemplified. It is more preferred to use the same solvent in polymerization as the solvent used in the photosensitive composition in the invention, by which the generation of particles during preservation can be restrained.

It is preferred to perform polymerization reaction in the atmosphere of inert gas such as nitrogen or argon. Polymerization is initiated with commercially available radical polymerization initiators (e.g., azo initiators, peroxide and the like). As radical polymerization initiators, azo initiators are preferred, and azo initiators having an ester group, a cyano group, or a carboxyl group are preferred. As preferred initiators, azobisisobutyronitrile, azobisdimethylvaleronitrile, dimethyl-2,2'-azibis(2-methyl-propionate), etc., are exemplified. Initiators are added additionally or dividedly, if desired, and after termination of the reaction, the reaction product is put into a solvent and an objective polymer is recovered as powder or a solid state. The reaction concentration is from 5 to 50 mass %, and preferably from 10 to 30 mass %. The reaction temperature is generally from 10 to 150° C., preferably from 30 to 120° C., and more preferably from 60 to 100° C.

When the photosensitive composition according to the invention is used in the upper layer resist of a multilayer resist, it is preferred that the resin of component (B) should have a silicon atom.

As resins having a silicon atom and capable of decomposing by the action of an acid to thereby increase the solubility in an alkali developing solution, resins having a silicon atom at least on one side of the main chain and the side chain can be used. As resins having a siloxane structure on the side chain of resins, copolymer of, e.g., an olefin monomer having a silicon atom on the side chain, and a (meth)acrylic acid monomer having maleic anhydride and an acid decomposable group on the side chain.

As resins having a silicon atom, resins having a trialkylsilyl structure and a monocyclic or polycyclic siloxane structure are preferred, resins having repeating units having the structures represented by any of the following formulae (SS-1) to (SS-4) are more preferred, and (meth)acrylic ester repeating units having the structures represented by any of formulae (SS-1) to (SS-4), vinyl repeating units, and allyl repeating units are still more preferred.

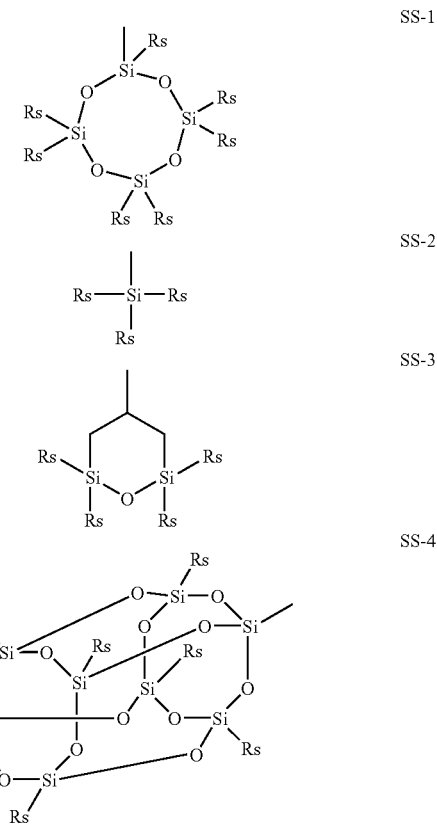

In formulae (SS-1) to (SS-4), Rs represents an alkyl group having from 1 to 5 carbon atoms, preferably a methyl group or an ethyl group.

It is preferred that resins having silicon atoms have two or more kinds of different repeating units having silicon atoms, resins having both (Sa) repeating unit having from 1 to 4 silicon atoms and (Sb) repeating unit having from 5 to 10 silicon atoms are more preferred, and resins having at least one repeating unit having a structure represented by any of formulae (SS-1) to (SS-3) and a repeating unit having a structure represented by formula (SS-4) are still more preferred.

When the positive photosensitive composition of the invention is irradiated with $F_2$ excimer laser beams, the resin of component (B) is preferably a resin having a structure wherein the main chain and/or side chain of the polymer skeleton are substituted with fluorine atoms and capable of decomposing by the action of an acid to increase the solubility in an alkali developing solution (hereinafter also referred to as "a fluorine-based acid-decomposable resin), the resin is more preferably a resin having a hydroxyl group the 1-position of which is substituted with a fluorine atom or a fluoroalkyl group, or having a group obtained by protecting a hydroxyl group the 1-position of which is substituted with a fluorine atom or a fluoroalkyl group with an acid-decomposable group. The especially preferred resin is a resin having a hexafluoro-2-propanol structure, or a resin having a structure that the hydroxyl group of hexafluoro-2-propanol is protected with an acid-decomposable group. By the incorporation of fluorine atoms, the transparency to the far ultraviolet rays, in particular to $F_2$ ray (157 nm) can be improved.

As the fluorine-based acid-decomposable resin, resins having at least one repeating unit represented by any of the following formulae (FA) to (FG) are preferably exemplified.

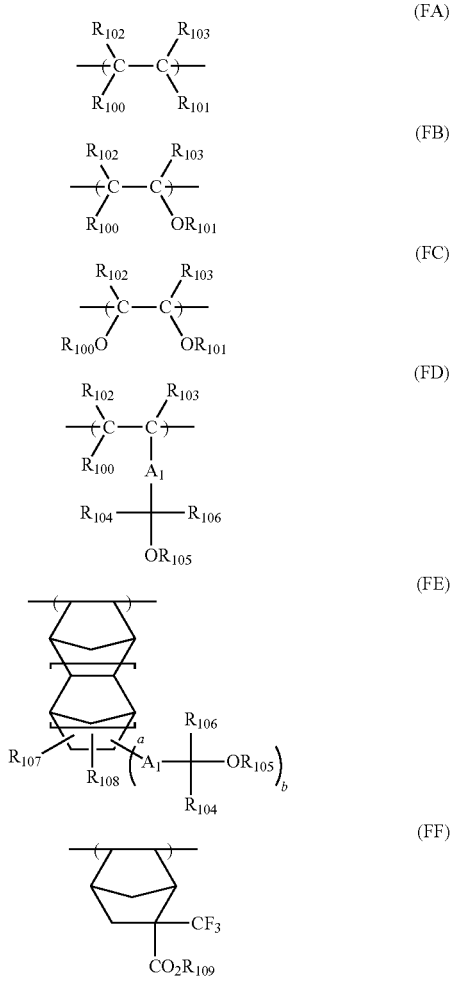

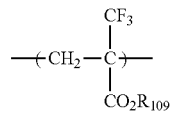

In the above formulae, $R_{100}$, $R_{101}$, $R_{102}$ and $R_{103}$ each independently represents a hydrogen atom, a fluorine atom, an alkyl group, or an aryl group.

$R_{104}$ and $R_{106}$ each independently represents a hydrogen atom, a fluorine atom, or an alkyl group, and at least one of $R_{104}$ and $R_{106}$ represents a fluorine atom or a fluoroalkyl group. Preferably both $R_{104}$ and $R_{106}$ represent a trifluoromethyl group.

$R_{105}$ represents a hydrogen atom, an alkyl group, a cycloalkyl group, an acyl group, an alkoxycarbonyl group, or a group decomposable by the action of an acid.

$A_1$ represents a single bond, a divalent linking group, e.g., an alkylene group, a cycloalkylene group, an alkenylene group, an arylene group, —OCO—, —COO—, —CON($R_{24}$)—, or a linking group containing a plurality of these groups. $R_{24}$ represents a hydrogen atom or an alkyl group.

$R_{107}$ and $R_{108}$ each independently represents a hydrogen atom, a halogen atom, an alkyl group, an alkoxyl group, an alkoxycarbonyl group, or a group decomposable by the action of an acid.

$R_{109}$ represents a hydrogen atom, an alkyl group, a cycloalkyl group, or a group decomposable by the action of an acid.

b represents 0, 1 or 2.

Further, $R_{100}$ and $R_{101}$ in formulae (FA) and (FC) may form a ring through an alkylene group (having from 1 to 5 carbon atoms) which may be substituted with a fluorine atom.

The repeating units represented by formulae (FA) to (FG) have at least 1, preferably 3 or more, fluorine atoms per one repeating unit.

In formulae (FA) to (FG), the alkyl group is an alkyl group having from 1 to 8 carbon atoms, specifically, a methyl group, an ethyl group, a propyl group, an n-butyl group, a sec-butyl group, a hexyl group, a 2-ethylhexyl group, and an octyl group are preferably exemplified.

The cycloalkyl group may be monocyclic or polycyclic. As the monocyclic cycloalkyl groups, those having from 3 to 8 carbon atoms, e.g., a cyclopropyl group, a cyclopentyl group, a cyclohexyl group, a cycloheptyl group, and a cyclooctyl group are preferably exemplified. As the polycyclic groups, preferably those having from 6 to 20 carbon atoms, e.g., an adamantyl group, a norbornyl group, an isobornyl group, a camphanyl group, a dicyclopentyl group, an α-pinel group, a tricyclodecanyl group, a tetracyclododecyl group, and an androstanyl group are exemplified. However, the carbon atoms in the monocyclic or polycyclic cycloalkyl groups may be substituted with hetero atoms such as an oxygen atom, etc.

The fluoroalkyl group is a fluoroalkyl group having from 1 to 12 carbon atoms, and specifically a trifluoromethyl group, a perfluoroethyl group, a perfluoropropyl group, a perfluorobutyl group, a perfluorohexyl group, a perfluorooctyl group, a perfluorooctylethyl group, and a perfluorododecyl group are preferably exemplified.

The aryl group is an aryl group having from 6 to 15 carbon atoms, and specifically a phenyl group, a tolyl group, a dimethylphenyl group, a 2,4,6-trimethylphenyl group, a naphthyl group, an anthryl group and a 9,10-dimethoxyanthryl group are preferably exemplified.

The alkoxyl group is an alkoxyl group having from 1 to 8 carbon atoms, and specifically a methoxy group, an ethoxy group, an n-propoxy group, an isopropoxy group, a butoxy group, a pentoxy group, an allyloxy group, and an octoxy group are preferably exemplified.

The acyl group is an acyl group having from 1 to 10 carbon atoms, and specifically a formyl group, an acetyl group, a propanoyl group, a butanoyl group, a pivaloyl group, an octanoyl group, and a benzoyl group are preferably exemplified.

As the alkoxycarbonyl group, an i-propoxycarbonyl group, a t-butoxycarbonyl group, a t-amyloxycarbonyl group, and a 1-methyl-1-cyclohexyloxycarbonyl group, preferably a secondary, and more preferably a tertiary alkoxycarbonyl group are exemplified.

As the halogen atom, e.g., a fluorine atom, a chlorine atom, a bromine atom and an iodine atom are exemplified.

As the alkylene group, preferably an alkylene group having from 1 to 8 carbon atoms, e.g., a methylene group, an ethylene group, a propylene group, a butylene group, a hexylene group, and an octylene group are exemplified.

As the alkenylene group, preferably an alkenylene group having from 2 to 6 carbon atoms, e.g., an ethenylene group, a propenylene group and a butenylene group are exemplified.

As the cycloalkylene group, preferably a cycloalkylene group having from 5 to 8 carbon atoms, e.g., a cyclopentylene group and a cyclohexylene group are exemplified.

As the arylene group, preferably an arylene group having from 6 to 15 carbon atoms, e.g., a phenylene group, a tolylene group and a naphthylene group are exemplified.

These groups may have a substituent, and the examples of the substituents include groups having active hydrogen, e.g., an alkyl group, a cycloalkyl group, an aryl group, an amino group, an amido group, a ureido group, a urethane group, a hydroxyl group, and a carboxyl group, a halogen atom (e.g., a fluorine atom, a chlorine atom, a bromine atom, and an iodine atom), an alkoxyl group (e.g., a methoxy group, an ethoxy group, a propoxy group, a butoxy group), a thioether group, an acyl group (e.g., an acetyl group, a propanoyl group, a benzoyl group), an acyloxy group (e.g., an acetoxy group, a propanoyloxy group, a benzoyloxy group), an alkoxycarbonyl group (e.g., a methoxycarbonyl group, an ethoxycarbonyl group, a propoxycarbonyl group), a cyano group, and a nitro group are exemplified.

Here, as the alkyl, cycloalkyl and aryl groups, those described above are exemplified, but the alkyl group may further be substituted with a fluorine atom or a cycloalkyl group.

As the groups capable of decomposing by the action of an acid to increase the solubility in an alkali developing solution contained in the fluorine-based acid-decomposable resins, e.g., —O—C($R_{36}$)($R_{37}$)($R_{38}$), —O—C($R_{36}$)($R_{37}$)(O$R_{39}$), —O—COO—C($R_{36}$)($R_{37}$)($R_{38}$), —O—C($R_{01}$)($R_{02}$)COO—C($R_{36}$)($R_{37}$)($R_{38}$), —COO—C($R_{36}$)($R_{37}$)($R_{38}$), and —COO—C($R_{36}$)($R_{37}$)(O$R_{39}$) can be exemplified.

$R_{36}$, $R_{37}$, $R_{38}$ and $R_{39}$ each independently represents an alkyl group, a cycloalkyl group, an aryl group, an aralkyl group, or an alkenyl group; $R_{01}$ and $R_{02}$ each independently represents a hydrogen atom, an alkyl group, a cycloalkyl group, an alkenyl group (e.g., a vinyl group, an allyl group, a butenyl group, a cyclohexenyl group), an aralkyl group (e.g., a benzyl group, a phenethyl group, a naphthylmethyl group), or an aryl group.

The preferred specific examples of the groups include the ether groups or the ester groups of tertiary alkyl groups such as a t-butyl group, a t-amyl group, a 1-alkyl-1-cyclohexyl group, a 2-alkyl-2-adamantyl group, a 2-adamantyl-2-propyl group, and a 2-(4-methylcyclohexyl)-2-propyl group, acetal groups or acetal ester groups such as a 1-alkoxy-1-ethoxy group and a tetrahydropyranyl group, a t-alkylcarbonate group and a t-alkylcarbonylmethoxy group.

The specific examples of the repeating units represented by formulae (FA) to (FG) are shown below, but the invention is not restricted thereto.

(F-1)

(F-2)

(F-3)

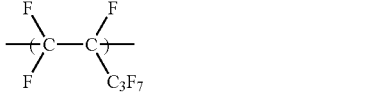

(F-4)

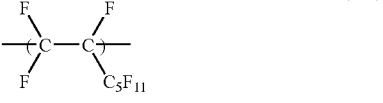

(F-5)

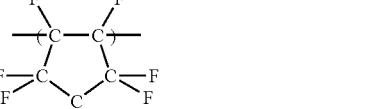

(F-6)

(F-7)

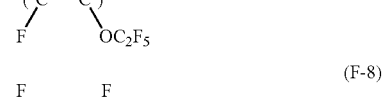

(F-8)

(F-9)

(F-10)

(F-11)

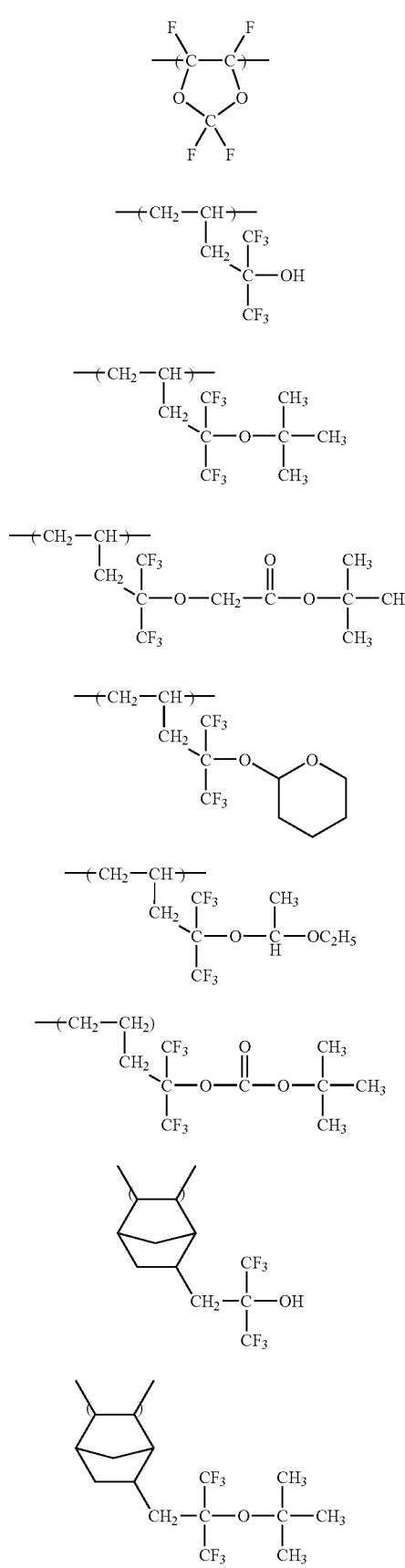
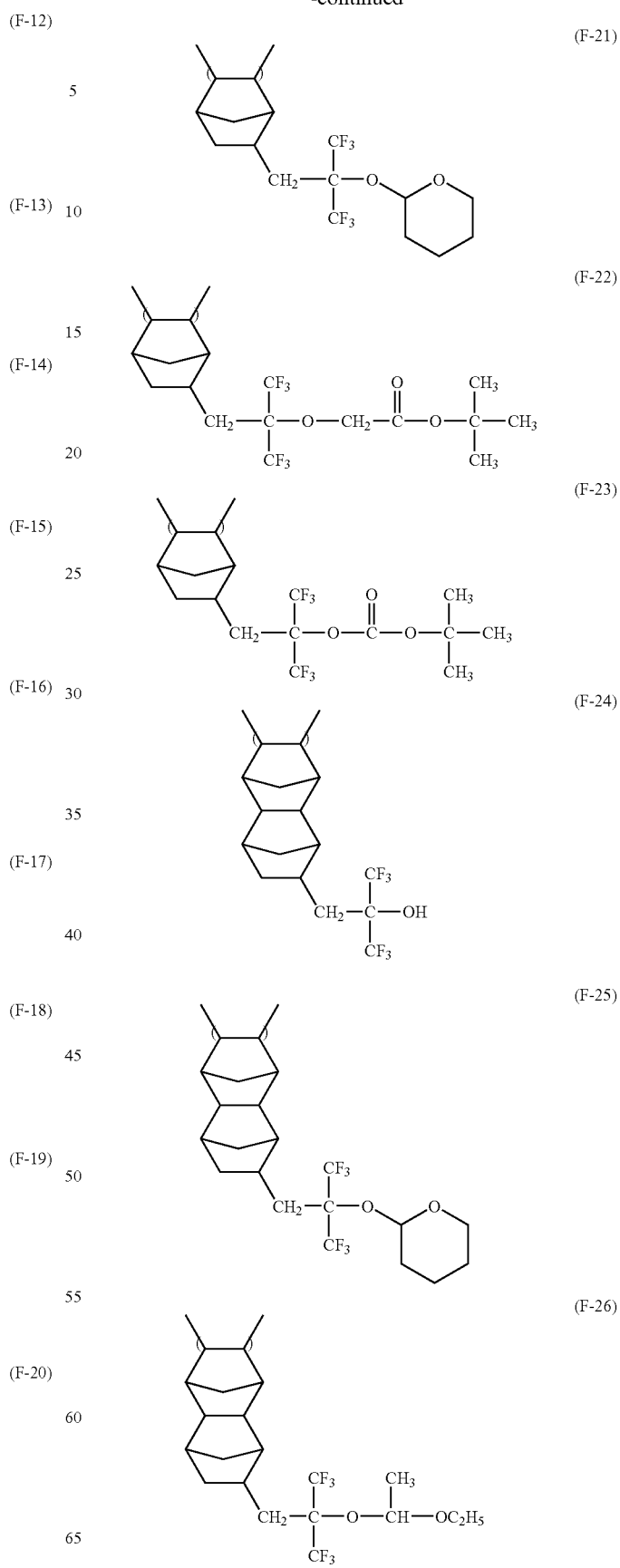

(F-27) 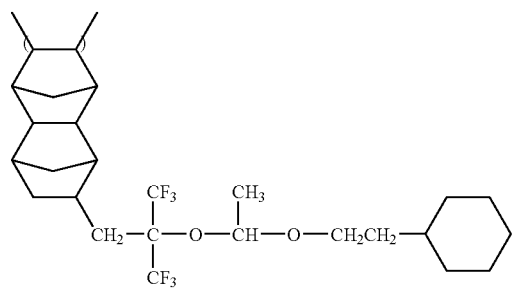
(F-28) 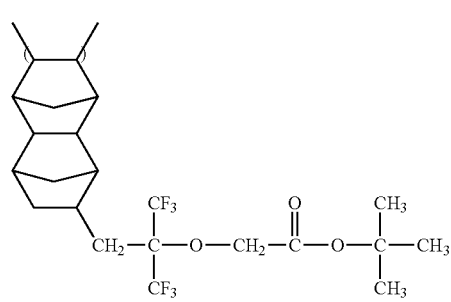
(F-29) 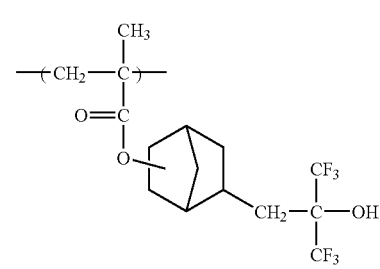
(F-30) 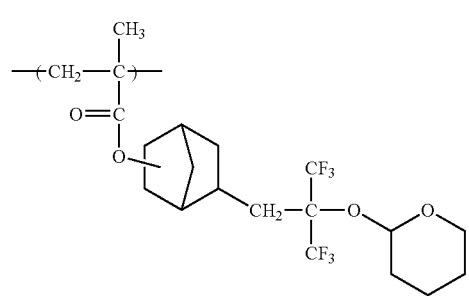
(F-31) 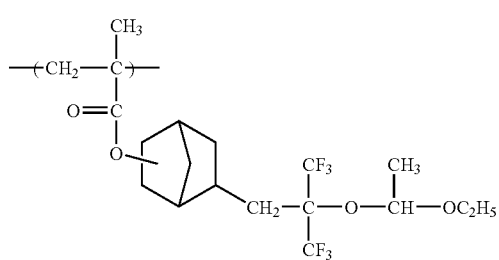
(F-32) 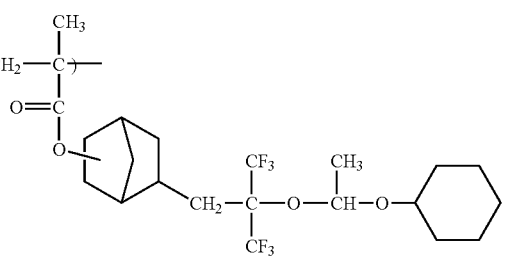
(F-33) 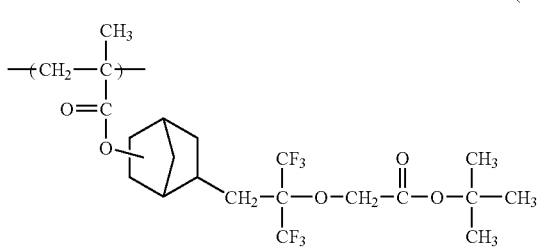
(F-34) 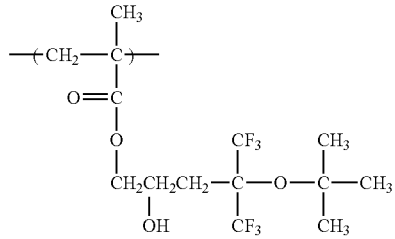
(F-35) 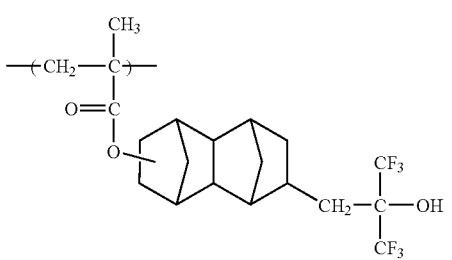
(F-36) 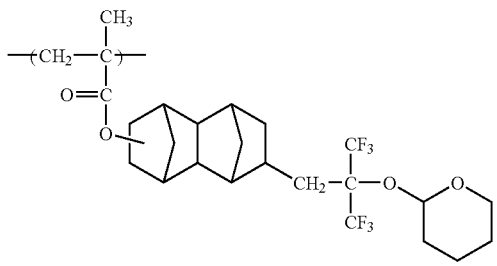
(F-37) 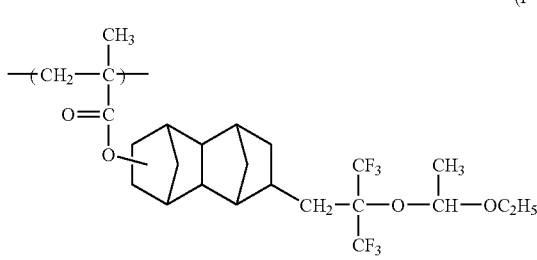

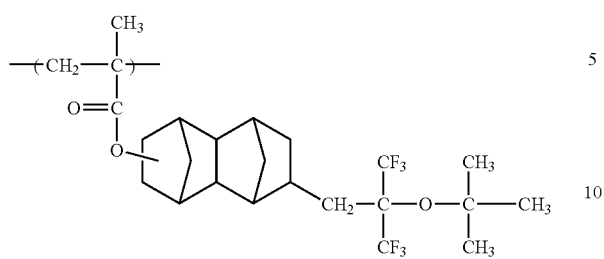 (F-38)
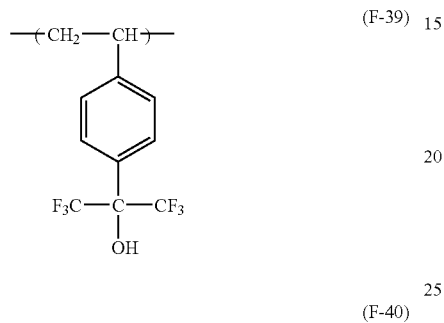 (F-39)
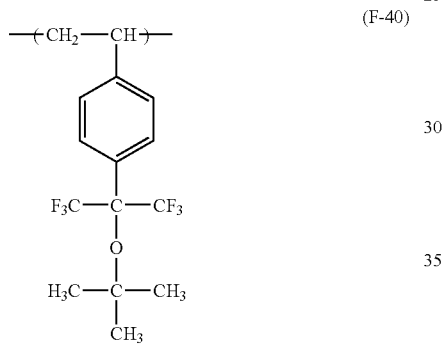 (F-40)
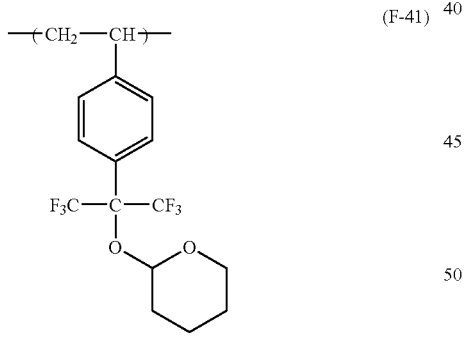 (F-41)
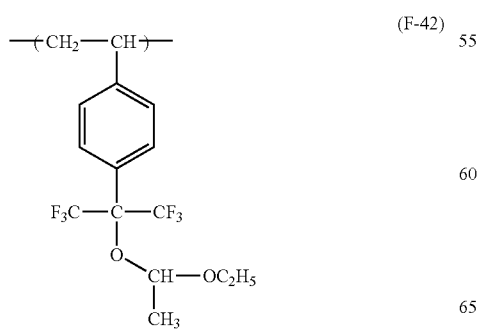 (F-42)
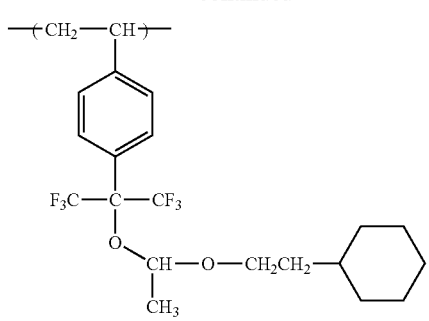 (F-43)
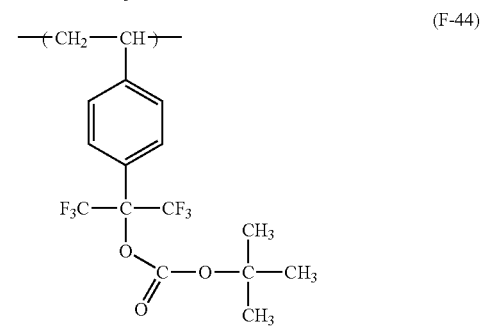 (F-44)
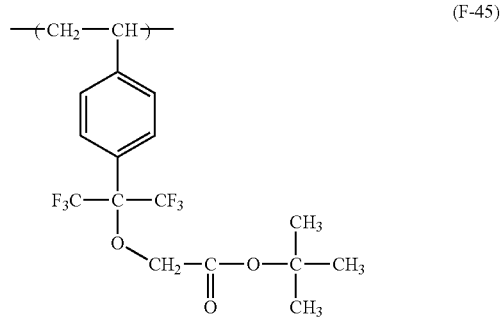 (F-45)
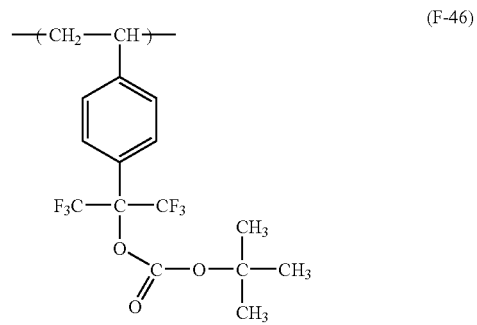 (F-46)
 (F-47)
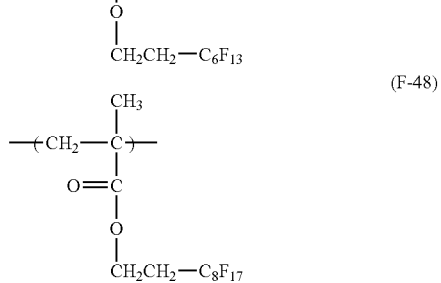 (F-48)

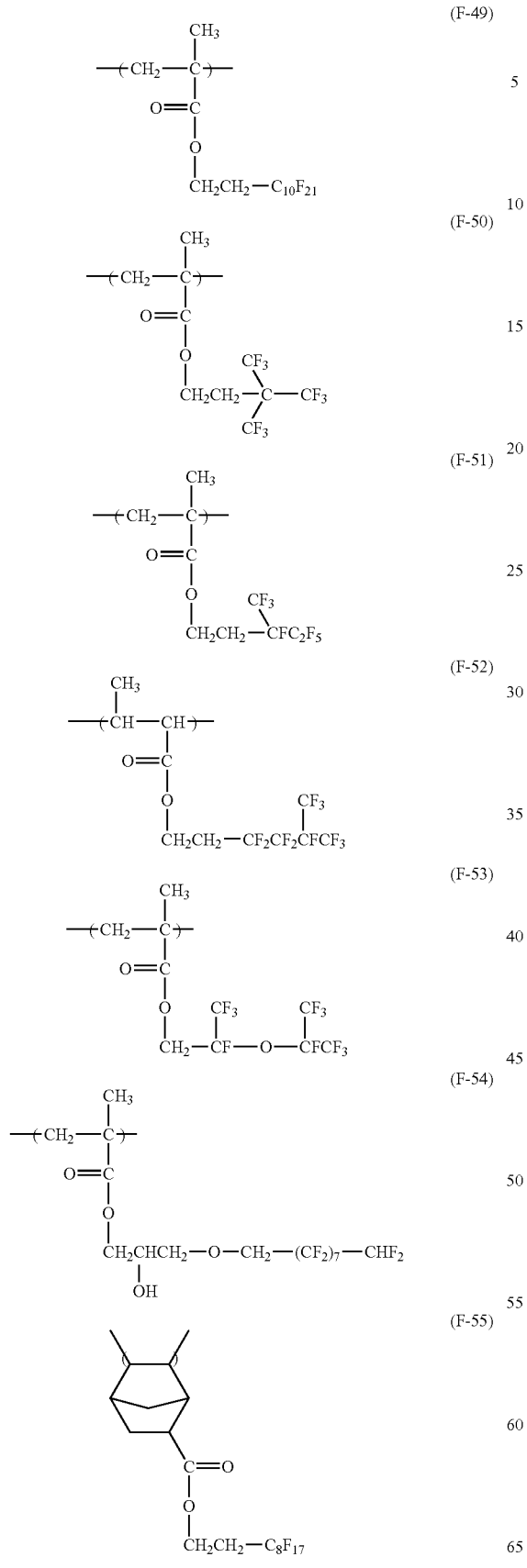

-continued (F-61)
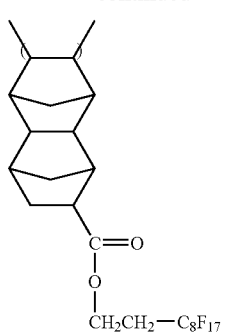

(F-62)
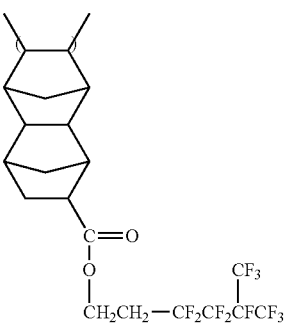

(F-63)
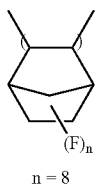
n = 8

(F-64)
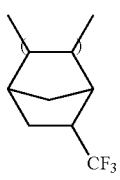

(F-65)
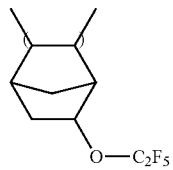

The total content of the repeating units represented by formulae (FA) to (FG) is generally from 10 to 80 mol % to all the repeating units constituting the resin, preferably from 30 to 70 mol %, and more preferably from 35 to 65 mol %.

For the purpose of further improving the performances of the resist of the invention, the fluorine-based acid-decomposable resins may further be copolymerized with other polymerizable monomers in addition to the above repeating structural units.

As the usable copolymerizable monomers, compounds having one addition polymerizable unsaturated bond selected from acrylic esters, acrylamides, methacrylic esters, methacrylamides, allyl compounds, vinyl ethers, vinyl esters, styrens, and crotonic esters other than described above are exemplified.

It is preferred that these fluorine-based acid-decomposable resins contain other repeating units as the copolymerization components besides the above repeating units having fluorine atoms from the points of improving dry etching resistance, adjusting alkali solubility, and improving adhesion with substrates. Preferred other repeating units are as follows.

1) The repeating units having an alicyclic hydrocarbon structure represented by any of formulae (pI) to (pVI) and formula (II-AB). Specifically the above exemplified repeating units 1 to 23 and repeating units [II-1 ] to [II-32] shown above. Preferably repeating units 1 to 23, wherein Rx represents $CF_3$.

2) The repeating units having a lactone structure represented by formula (Lc) and any of formulae (V-1) to (V-5). Specifically the above-exemplified repeating units, in particular, the above-exemplified repeating units represented by formula (Lc) and formulae (V-1) to (V-4).

3) The repeating units derived from the vinyl compounds having maleic anhydride, vinyl ether or a cyano group represented by the following formula (XV), (XVI) or (XVII). Specifically repeating units (C-1) to (C-15) shown below. These repeating units may or may not contain a fluorine atom.

(XV)
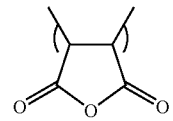

(XVI)
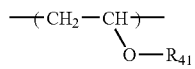

(XVII)
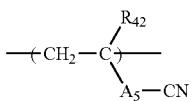

In the above formulae, $R_{41}$ represents an alkyl group, a cycloalkyl group, an aralkyl group, or an aryl group, and the alkyl group represented by $R_{41}$ may be substituted with an aryl group.

$R_{42}$ represents a hydrogen atom, a halogen atom, a cyano group, or an alkyl group.

$A_5$ represents a single bond, a divalent alkylene group, alkenylene group, cycloalkylene group, or arylene group, or —O—CO—$R_{22}$—, —CO—O—$R_{23}$—, or —CO—N ($R_{24}$)—$R_{25}$—.

$R_{22}$, $R_{23}$ and $R_{25}$, which may be the same or different, each independently represents a single bond, or a divalent alkylene group, alkenylene group, cycloalkylene group or arylene group which may have an ether group, an ester group, an amido group, a urethane group or a ureido group.

$R_{24}$ represents a hydrogen atom, an alkyl group, a cycloalkyl group, an aralkyl group, or an aryl group.

Here, as the examples of the substituents, the same groups as the substituents in formulae (FA) to (FG) can be exemplified.

The specific examples of the repeating structural units represented by formulae (XV) to (XVII) are shown below, but the invention is not restricted thereto.

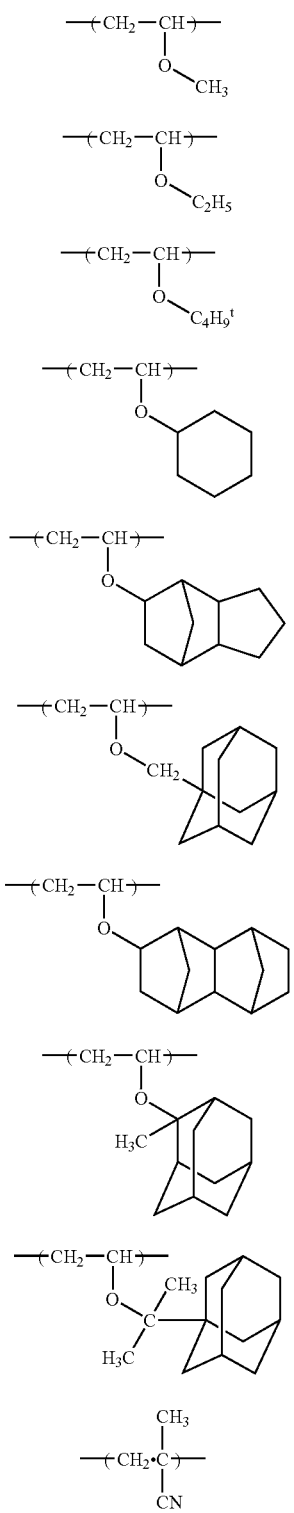

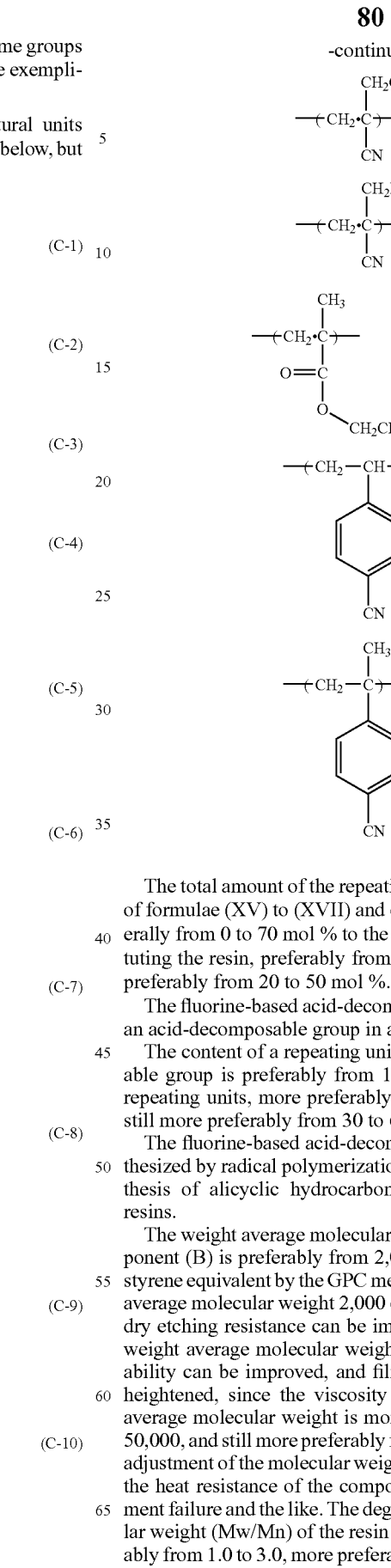

The total amount of the repeating units represented by any of formulae (XV) to (XVII) and other repeating units is generally from 0 to 70 mol % to the total repeating units constituting the resin, preferably from 10 to 60 mol %, and more preferably from 20 to 50 mol %.

The fluorine-based acid-decomposable resins may contain an acid-decomposable group in any repeating unit.

The content of a repeating unit having an acid decomposable group is preferably from 10 to 70 mol % to the total repeating units, more preferably from 20 to 60 mol %, and still more preferably from 30 to 60 mol %.

The fluorine-based acid-decomposable resins can be synthesized by radical polymerization almost similar to the synthesis of alicyclic hydrocarbon-based acid-decomposable resins.

The weight average molecular weight of the resin of component (B) is preferably from 2,000 to 200,000 as the polystyrene equivalent by the GPC method. By making the weight average molecular weight 2,000 or more, heat resistance and dry etching resistance can be improved, and by making the weight average molecular weight 200,000 or less, developability can be improved, and film-forming property can be heightened, since the viscosity becomes low. The weight average molecular weight is more preferably from 5,000 to 50,000, and still more preferably from 7,000 to 30,000. By the adjustment of the molecular weight, it is possible to reconcile the heat resistance of the composition, resolution, development failure and the like. The degree of dispersion of molecular weight (Mw/Mn) of the resin of component (B) is preferably from 1.0 to 3.0, more preferably from 1.2 to 2.5, and still more preferably from 1.2 to 1.6. By the adjustment of the degree of dispersion to a proper range, the performance of line edge roughness can be increased.

In the positive photosensitive composition in the invention, the proportion of the resin of component (B) of the invention in the entire composition is preferably from 40 to 99.99 mass % in the total solids content, more preferably from 50 to 99 mass %, and still more preferably from 80 to 96 mass %.

[4] Resin (C) Soluble in an Alkali Developing Solution:

The resin is hereinafter referred to as "component (C)" or "alkali-soluble resin", also.

The alkali dissolution rate of alkali-soluble resins is preferably 20 Å/sec or more when measured with 0.261 N tetramethylammonium hydroxide (TMAH) at 23° C., and especially preferably 200 Å/sec or more.

As alkali-soluble resins for use in the invention, e.g., novolak resins, hydrogenated novolak resins, acetonepyrogallol resins, o-polyhydroxystyrene, m-polyhydroxystyrene, p-polyhydroxystyrene, hydrogenated polyhydroxystyrene, halogen-or alkyl-substituted polyhydroxystyrene, hydroxystyrene-N-substituted maleimide copolymers, o/p- and m/p-hydroxystyrene copolymers, partially O-alkylated products of the hydroxyl group of polyhydroxystyrene (e.g., from 5 to 30 mol % O-methylated, O-(1-methoxy)ethylated, O-(1-ethoxy)ethylated, O-2-tetrahydropyranylated, and O-(t-butoxycarbonyl)methylated products), and partially O-acylated products (e.g., from 5 to 30 mol % o-acetylated and O-(t-butoxy)carbonylated products), styrene-maleic anhydride copolymers, styrene-hydroxystyrene copolymers, α-methyl-styrene-hydroxystyrene copolymers, carboxyl group-containing methacrylic resins and derivatives thereof, and polyvinyl alcohol derivatives can be exemplified, but the invention is not limited to these resins.

Particularly preferred alkali-soluble resins are novolak resins, o-polyhydroxystyrene, m-polyhydroxystyrene p-polyhydroxystyrene, copolymers of them, alkyl-substituted polyhydroxystyrene, partially O-alkylated or O-acylated products of polyhydroxystyrene, styrene-hydroxystyrene copolymers, and α-methylstyrene-hydroxystyrene copolymers.

The novolak resins can be obtained by addition condensation to aldehydes with the prescribed monomers as main components in the presence of an acid catalyst.

The weight average molecular weight of alkali-soluble resins is 2,000 or more, preferably from 5,000 to 200,000, and more preferably from 5,000 to 100,000.

Here, the weight average molecular weight is defined as the polystyrene equivalent by gel permeation chromatography.

Alkali-soluble resins (C) in the invention may be used in combination of two kinds or more.

The use amount of alkali-soluble resins is from 40 to 97 mass % based on all the solids content of the photosensitive composition, and preferably from 60 to 90 mass %.

[5] Dissolution Inhibiting Compound (E) Capable of Decomposing by the Action of an Acid to Increase Solubility in an Alkali Developing Solution having a Molecular Weight of 3,000 or less:

The compound is hereinafter referred to as "component (E)" or also "dissolution-inhibiting compound".

As dissolution inhibiting compound (E) capable of decomposing by the action of an acid to thereby increase the solubility in an alkali developing solution having a molecular weight of 3,000 or less, alicyclic or aliphatic compounds containing an acid-decomposable group, such as cholic acid derivatives containing an acid-decomposable group described in Proceeding of SPIE, 2724, 355 (1996) are preferred so as not to reduce the permeability to lights of 220 nm or less. As the acid-decomposable groups and alicyclic structures, the same as those described above in the alicyclic hydrocarbon-based acid-decomposable resin are exemplified.

When the photosensitive composition of the invention is exposed with a KrF excimer laser or irradiated with electron beams, a phenolic compound having a structure that the phenolic hydroxyl group is substituted with an acid-decomposable group is preferably used. As the phenolic compounds, compounds having from 1 to 9 phenolic skeletons are preferred, and those having from 2 to 6 are more preferred.

The molecular weight of the dissolution-inhibiting compound in the invention is 3,000 or less, preferably from 300 to 3,000, and more preferably from 500 to 2,500.

The addition amount of the dissolution-inhibiting compound is preferably from 3 to 50 mass % based on the solids content of the photosensitive composition, and more preferably from 5 to 40 mass %.

The specific examples of the dissolution-inhibiting compounds are shown below, but the invention is not restricted thereto.

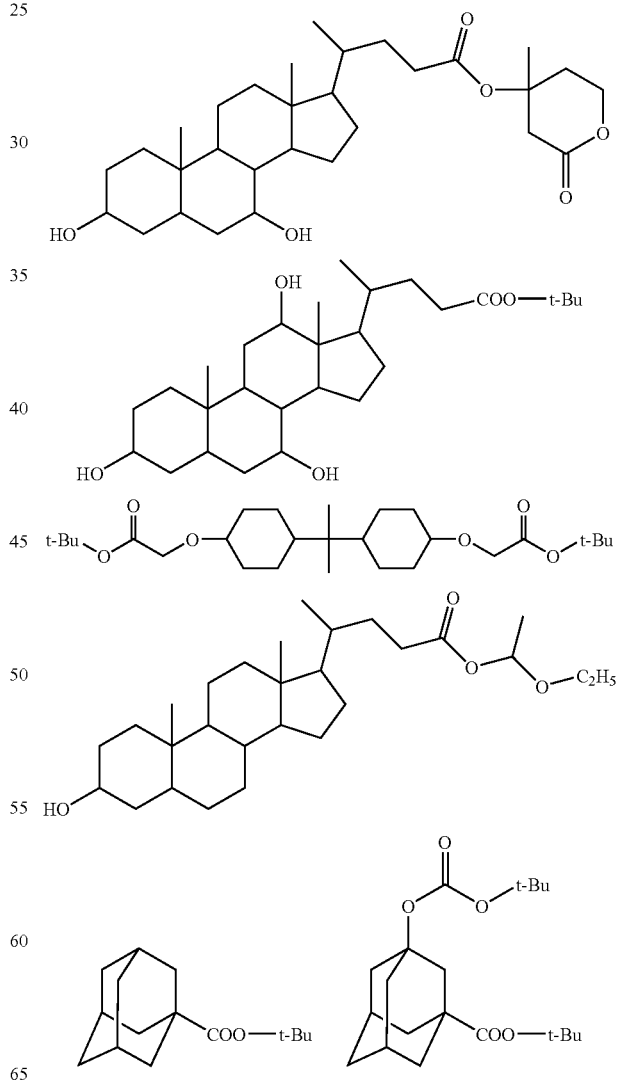

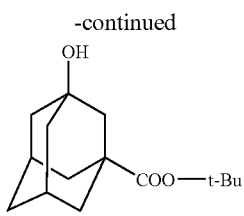

[6] Acid Crosslinking Agent (D) Capable of Crosslinking with the Alkali-Soluble Resin by the Action of an Acid:

The acid crosslinking agent is hereinafter referred to as "component (D)" or also "crosslinking agent".

A crosslinking agent is used in the negative photosensitive composition of the invention.

Every compound capable of crosslinking the resins soluble in an alkali developing solution by the action of an acid can be used as crosslinking agents, but the following (1) to (3) are preferably used.

(1) Hydroxymethyl body, alkoxymethyl body and acyloxymethyl body of phenol derivatives
(2) Compounds having an N-hydroxymethyl group, an N-alkoxymethyl group or an N-acyloxymethyl group
(3) Compounds having an epoxy group As the alkoxymethyl groups, those having 6 or less carbon atoms, and as the acyloxymethyl groups, those having 6 or less carbon atoms are preferred.

Of these crosslinking agents, particularly preferred compounds are shown below.

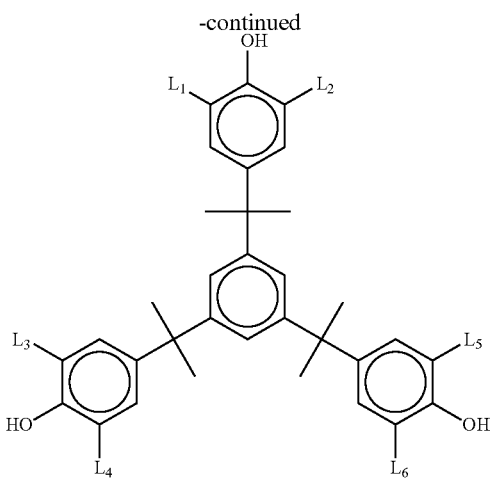

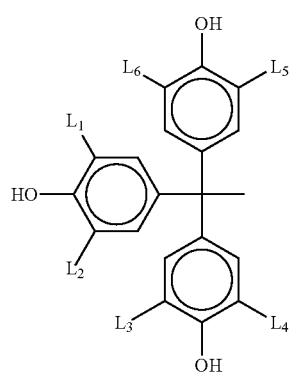

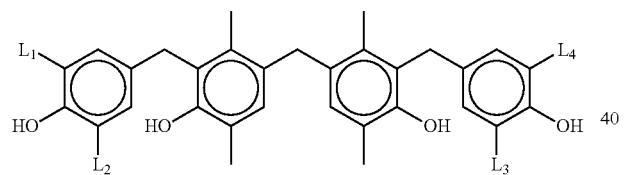

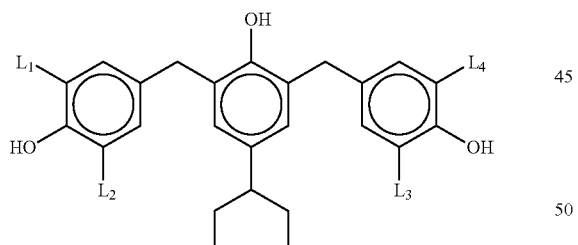

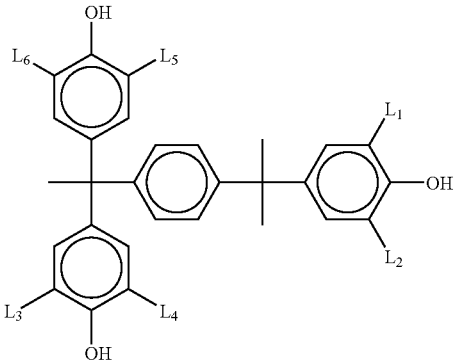

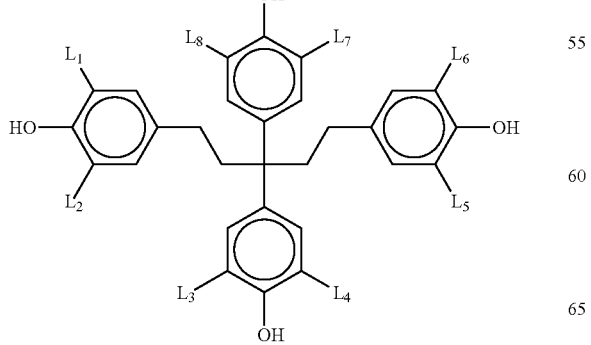

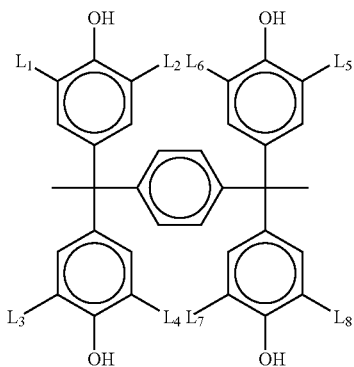

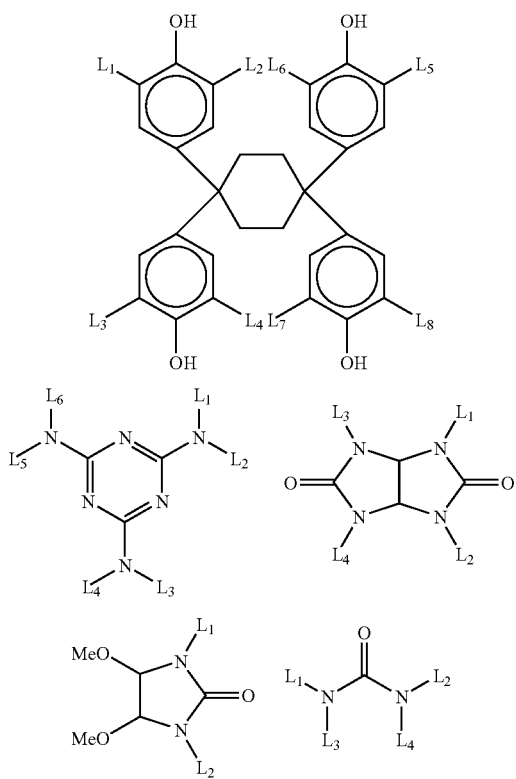

In the above formulae, $L_1$ to $L_8$, which may be the same or different, each independently represents a hydrogen atom, a hydroxymethyl group, a methoxymethyl group, an ethoxymethyl group, or an alkyl group having from 1 to 6 carbon atoms.

Crosslinking agents are used generally in proportion of from 3 to 70 mass % in the solids content of the photosensitive composition, and preferably from 5 to 50 mass %.

[7] Basic Compound (F):

For decreasing the fluctuation of performances during the period of time from exposure to heating, it is preferred for the photosensitive composition of the invention to contain (F) a basic compound.

As the preferred structures of basic compounds, the structures represented by any of the following formulae (A) to (E) can be exemplified.

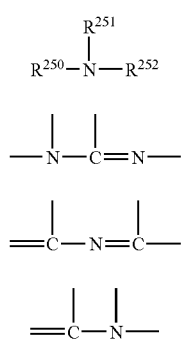

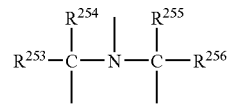

In formula (A), $R_{250}$, $R_{251}$ and $R_{252}$ each independently represents a hydrogen atom, an alkyl group having from 1 to 20 carbon atoms, a cycloalkyl group having from 3 to 20 carbon atoms, or an aryl group having from 6 to 20 carbon atoms, and $R_{250}$ and $R_{251}$ may be bonded to each other to form a ring. These groups may have a substituent, and as the alkyl group and cycloalkyl group having a substituent, an aminoalkyl group having from 1 to 20 carbon atoms or an aminocycloalkyl group having from 3 to 20 carbon atoms, a hydroxyalkyl group having from 1 to 20 carbon atoms or a hydroxycycloalkyl group having from 3 to 20 carbon atoms are preferred.

These groups may contain an oxygen atom, a sulfur atom or a nitrogen atom in the alkyl chain.

In formula (E), $R_{253}$, $R_{254}$, $R_{255}$ and $R_{256}$ each independently represents an alkyl group having from 1 to 6 carbon atoms, or a cycloalkyl group having from 3 to 6 carbon atoms.

As the preferred examples of basic compounds, guanidine, aminopyrrolidine, pyrazole, pyrazoline, piperazine, aminomorpholine, aminoalkylmorpholine, and piperidine can be exemplified, and these compounds may have a substituent. As further preferred compounds, compounds having an imidazole structure, a diazabicyclo structure, an onium hydroxide structure, an onium carboxylate structure, a trialkylamine structure, an aniline structure, or a pyridine structure, alkylamine derivatives having a hydroxyl group and/or an ether bond, and aniline derivatives having a hydroxyl group and/or an ether bond can be exemplified.

As the compounds having an imidazole structure, imidazole, 2,4,5-triphenylimidazole, and benzimidazole can be exemplified. As the compounds having a diazabicyclo structure, 1,4-diazabicyclo[2.2.2]octane, 1,5-diazabicyclo[4.3.0]non-5-ane, and 1,8-diazabicyclo[5.4.0]undeca-7-ene can be exemplified. As the compounds having an onium hydroxide structure, triarylsulfonium hydroxide, phenacylsulfonium hydroxide, sulfonium hydroxide having a 2-oxoalkyl group, specifically triphenylsulfonium hydroxide, tris(t-butylphenyl)sulfonium hydroxide, bis(t-butylphenyl)iodonium hydroxide, phenacylthiophenium hydroxide, and 2-oxopropylthiophenium hydroxide can be exemplified. The compounds having an onium carboxylate structure are compounds having an onium hydroxide structure in which the anionic part is carboxylated, e.g., acetate, adamantane-1-carboxylate, and perfluoroalkyl carboxylate are exemplified. As the compounds having a trialkylamine structure, tri(n-butyl)amine and tri(n-octyl)amine can be exemplified. As the aniline compounds, 2,6-diisopropylaniline and N,N-dimethylaniline can be exemplified. As the alkylamine derivatives having a hydroxyl group and/or an ether bond, ethanolamine, diethanolamine, triethanolamine, and tris(methoxyethoxyethyl)amine can be exemplified. As the aniline derivatives having a hydroxyl group and/or an ether bond, N,N-bis(hydroxyethyl)-aniline can be exemplified.

These basic compounds are used alone or in combination of two or more. However, when the use amount of component (B) is 0.05 mass % or more, a basic compound may not be used. When a basic compound is used, the use amount of the basic compound is generally from 0.001 to 10 mass % based on the solids content of the photosensitive composition, and preferably from 0.01 to 5 mass %. For obtaining a sufficient addition effect, the addition amount is preferably 0.001 mass % or more, and in view of sensitivity and the developability of a non-exposed area, the addition amount is preferably 10 mass % or less.

[8] Fluorine and/or Silicon Surfactant (G):

It is preferred for the photosensitive composition in the invention to further contain a surfactant either one, or two or more, of fluorine and/or silicon surfactants (a fluorine surfactant, a silicon surfactant, a surfactant containing both a fluorine atom and a silicon atom).

By containing fluorine and/or silicon surfactants, it becomes possible for the photosensitive composition in the invention to provide a resist pattern excellent in sensitivity and resolution, and low in defects in adhesion and development in using an exposure light source of 250 nm or lower, in particular 220 nm or lower.

These fluorine and/or silicon surfactants are disclosed, e.g., in JP-A-62-36663, JP-A-61-226746, JP-A-61-226745, JP-A-62-170950, JP-A-63-34540, JP-A-7-230165, JP-A-8-62834, JP-A-9-54432, JP-A-9-5988, JP-A-2002-277862, U.S. Pat. Nos. 5,405,720, 5,360,692, 5,529,881, 5,296,330, 5,436,098, 5,576,143, 5,294,511 and 5,824,451. The commercially available surfactants shown below can also be used as they are.

As the commercially available fluorine or silicon surfactants usable in the invention, e.g., Eftop EF301 and EF303 (manufactured by Shin-Akita Kasei Co., Ltd.), Fluorad FC 430 and 431 (manufactured by Sumitomo 3M Limited), Megafac F171, F173, F176, F189, and R08 (manufactured by Dainippon Ink and Chemicals Inc.), Sarfron S-382, SC 101, 102, 103, 104, 105 and 106 (manufactured by ASAHI GLASS CO., LTD.), Troy Sol S-366 (manufactured by Troy Chemical Co., Ltd.) are exemplified. In addition, polysiloxane polymer KP-341 (manufactured by Shin-Etsu Chemical Co., Ltd.) can also be used as a silicon surfactant.

In addition to these known surfactants as exemplified above, surfactants using polymers having fluoro-aliphatic groups derived from fluoro-aliphatic compounds manufactured by a telomerization method (also called a telomer method) or an oligomerization method (also called an oligomer method) can be used. The fluoro-aliphatic compounds can be synthesized by the method disclosed in JP-A-2002-90991.

As the polymers having fluoro-aliphatic groups, copolymers of monomers having fluoro-aliphatic groups and (poly(oxyalkylene)) acrylate and/or (poly(oxyalkylene)) methacrylate are preferred, and they may be distributed at random or block copolymerized. As the poly(oxyalkylene) groups, a poly(oxyethylene) group, a poly(oxypropylene) group, and a poly(oxybutylene) group are exemplified. Further, the polymers may be units having alkylenes different in chain length in the same chain length, such as a block combination of poly(oxyethylene and oxypropylene and oxyethylene), and a block combination of poly(oxyethylene and oxypropylene). In addition, copolymers of monomers having fluoro-aliphatic groups and poly(oxyalkylene) acrylate (or methacrylate) may be not only bipolymers but also terpolymers or higher polymers obtained by copolymerization of monomers having different two or more kinds of fluoro-aliphatic groups and different two or more kinds of poly(oxyalkylene) acrylates (or methacrylates) at the same time.

For example, as commercially available surfactants, Megafac F178, F470, F473, F475, F476 and F472 (manufactured by Dainippon Ink and Chemicals Inc.) can be exemplified. Further, copolymers of acrylate (or methacrylate) having a $C_6F_{13}$ group and (poly(oxyalkylene))acrylate (or methacrylate), copolymers of acrylate (or methacrylate) having a $C_6F_{13}$ group, (poly(oxyethylene))acrylate (or methacrylate), and (poly(oxypropylene))acrylate (or methacrylate), copolymers of acrylate (or methacrylate) having a $C_8F_{17}$ group and (poly(oxyalkylene))acrylate (or methacrylate), and copolymers of acrylate (or methacrylate) having a $C_8F_{17}$ group, (poly(oxyethylene))acrylate (or methacrylate), and poly(oxypropylene)acrylate (or methacrylate) are exemplified.

The addition amount of fluorine and/or silicon surfactant is preferably from 0.0001 to 2 mass % to the total amount of the photosensitive composition (excluding solvents), and more preferably from 0.001 to 1 mass %.

[9] Organic Solvent (H):

The above components of the photosensitive composition of the invention are dissolved in a prescribed organic solvent.

As the organic solvents usable in the invention, ethylene dichloride, cyclohexanone, cyclopentanone, 2-heptanone, γ-butyrolactone, methyl ethyl ketone, ethylene glycol monomethyl ether, ethylene glycol monoethyl ether, 2-methoxyethyl acetate, ethylene glycol monoethyl ether acetate, propylene glycol monomethyl ether, propylene glycol monomethyl ether acetate, toluene, ethyl acetate, methyl lactate, ethyl lactate, methyl methoxypropionate, ethyl ethoxypropionate, methyl pyruvate, ethyl pyruvate, propyl pyruvate, N,N-dimethylformamide, dimethyl sulfoxide, N-methylpyrrolidone, and tetrahydrofuran are exemplified.

(Ia) Ketone Solvents:

Solvents containing at least a ketone structure are preferably used in the invention.

As the solvents containing a ketone structure, chain-like ketone solvents and cyclic ketone solvents are exemplified, and those having from 5 to 8 carbon atoms are preferred for capable of obtaining good coating property.

As the chain-like ketone solvents, e.g., 2-heptanone, methyl ethyl ketone, methyl isobutyl ketone, etc., are exemplified, and 2-heptanone is preferred.

As the cyclic ketone solvents, e.g., cyclopentanone, 3-methyl-2-cyclopentanone, cyclohexanone, 2-methylcyclohexanone, 2,6-dimethylcyclohexanone, cycloheptanone, cyclooctanone, isophorone, etc., are exemplified, and cyclohexanone and cycloheptanone are preferred.

It is preferred that the solvents having a ketone structure are used alone, or as mixed solvents with other solvents. As the solvents to be mixed (combined use solvents), propylene glycol monoalkyl ether carboxylate, alkyl lactate, propylene glycol monoalkyl ether, alkyl alkoxypropionate, lactone compounds, etc., can be exemplified.

As the propylene glycol monoalkyl ether carboxylate, e.g., propylene glycol monomethyl ether acetate, propylene glycol monomethyl ether propionate, propylene glycol monoethyl ether acetate, etc., can be exemplified.

As the alkyl lactate, e.g., methyl lactate, ethyl lactate, etc., can be exemplified.

As the propylene glycol monoalkyl ether, e.g., propylene glycol monomethyl ether and propylene glycol monoethyl ether, etc., can be exemplified.

As the alkyl alkoxypropionate, e.g., methyl methoxypropionate, ethyl methoxypropionate, methyl ethoxypropionate, ethyl ethoxypropionate, etc., can be exemplified.

As the lactone compounds, e.g., γ-butyrolactone, etc., can be exemplified.

As preferred combined use solvent, propylene glycol monoalkyl ether carboxylate, alkyl lactate and propylene glycol monoalkyl ether can be exemplified, and as more preferred combined use solvent, propylene glycol monomethyl ether acetate can be exemplified.

By the use of mixed solvents of ketone solvents and combined use solvents, substrate adhesion, developability and DOF are improved.

The ratio of the ketone solvent and the combined use solvent (mass ratio) is preferably from 10/90 to 95/5, more preferably from 20/80 to 80/20, and still more preferably from 30/70 to 70/30.

In view of heightening uniform film thickness and resistance to development failure, high boiling point solvents having a boiling point of 200° C. or higher, e.g., ethylene carbonate, propylene carbonate, etc., may be mixed.

The addition amount of these high boiling point solvents is generally from 0.1 to 15 mass % in all the solvents, preferably from 0.5 to 10 mass %, and more preferably from 1 to 5 mass %.

In the invention, a photosensitive composition having solids content concentration of generally from 3 to 25 mass %, preferably from 5 to 22 mass %, and more preferably from 5 to 15 mass % is prepared with a single solvent, preferably two or more solvents.

[10] Other Additives (I):

If necessary, dyes, plasticizers, surfactants other than the surfactants of component (G), photosensitizers, and compounds for expediting the dissolution of composition in a developing solution may be further added to the photosensitive composition in the present invention.

Compounds for expediting dissolution in a developing solution that can be used in the invention are low molecular weight compounds having a molecular weight of 1,000 or less and having two or more phenolic OH groups or one or more carboxyl groups. When carboxyl groups are contained, alicyclic or aliphatic compounds are preferred.

The preferred addition amount of these dissolution accelerating compounds is preferably from 2 to 50 mass % based on the resin of component (B) or the resin of component (C), and more preferably from 5 to 30 mass %. The amount is preferably 50 mass % or less in the point of restraint of development residue and prevention of pattern deformation in development.

These phenolic compounds having a molecular weight of 1,000 or less can be easily synthesized with referring to the methods disclosed, e.g., in JP-A-4-122938, JP-A-2-28531, U.S. Pat. No. 4,916,210, and EP 219294.

As the specific examples of the alicyclic or aliphatic compounds having a carboxyl group, carboxylic acid derivatives having a steroid structure, e.g., cholic acid, deoxycholic acid, and lithocholic acid, adamantanecarboxylic acid derivatives, adamantanedicarboxylic acid, cyclohexanecarboxylic acid, and cyclohexanedicarboxylic acid are exemplified, but the invention is not restricted to these compounds.

In the invention, surfactants other than fluorine and/or silicon surfactants (G) can also be used. Specifically, nonionic surfactants, such as polyoxyethylene alkyl ethers, polyoxyethylene alkylallyl ether, polyoxyethylene-polyoxypropylene block copolymers, sorbitan aliphatic esters, and polyoxyethylene sorbitan aliphatic esters can be exemplified.

These surfactants may be used alone or may be used in combination of some kinds.

[11] Pattern-Forming Method (J):

The photosensitive composition in the invention is used by dissolving the above components in a prescribed organic solvent, preferably a mixed solvent as described above, and coating the solution on a prescribed support as follows.

For example, the photosensitive composition is coated on a substrate such as the one used in the manufacture of precision integrated circuit element (e.g., silicon/silicon dioxide coating) by an appropriate coating method with a spinner or a coater, and dried, to thereby form a photosensitive film. Incidentally, it is also possible to coat a known antireflection film.

The photosensitive film is irradiated with actinic ray or radiation through a prescribed mask, preferably subjected to baking (heating), and then development. Thus, a good pattern can be obtained.

At the time of irradiation with actinic ray or radiation, exposure (immersion exposure) may be performed by filling a liquid having higher refractive index than that of air between a photosensitive film and a lens, by which resolution can be raised.

As actinic rays or radiation, infrared rays, visible rays, ultraviolet rays, far ultraviolet rays, X-rays and electron beams can be exemplified, and preferably far ultraviolet rays of wavelengths of 250 nm or less, and more preferably 220 nm or less. Specifically, a KrF excimer laser (248 nm), an ArF excimer laser (193 nm), an $F_2$ excimer laser (157 nm), X-rays and electron beams are exemplified, and ArF excimer lasers, $F_2$ excimer lasers, EUV (13 nm), and electron beams are preferred.

(Immersion Exposure):

When the photosensitive composition in the invention is subjected to immersion exposure, it is preferred that the photosensitive composition is used in a thickness of from 30 to 250 nm in view of the improvement of resolution, and more preferably a thickness of from 30 to 100 nm. Such a desired thickness can be realized by setting the concentration of solids content in the photosensitive composition in a proper range and giving appropriate viscosity to thereby improve the coating property and film forming property.

The concentration of all the solids content in the photosensitive composition is generally from 1 to 10 mass %, more preferably from 1 to 8 mass %, and still more preferably from 1.0 to 6.0 mass %.

When the photosensitive composition in the invention is subjected to immersion exposure, the photosensitive composition is used by dissolving each of the above components in a prescribed organic solvent, preferably in a mixed solvent as described above, and coating the solution on a prescribed support as follows.

That is, the photosensitive composition is coated on a substrate such as the one used in the production of precision integrated circuit elements (e.g., silicon/silicon dioxide coating) by an appropriate coating method with a spinner or a coater in an arbitrary thickness (generally from 30 to 500 nm). After coating, if necessary, a resist film is washed with the immersion liquid. The washing time is generally from 5 seconds to 5 minutes.

Subsequently, the coated photosensitive composition is dried by spin or bake to form a photosensitive film (hereafter also called resist film), and the resist film formed is subjected to exposure (immersion exposure) for pattern formation through a mask via an immersion liquid. For example, exposure is performed in the state of filling an immersion liquid between a resist film and an optical lens. The exposure dose can be optionally set, but is generally from 1 to 100 mJ/cm$^2$. After exposure, if necessary, the resist film is washed with the immersion liquid. The washing time is generally from 5 seconds to 5 minutes. After that, the resist film is preferably subjected to spin or/and bake, development and rinsing, whereby a good pattern can be obtained. It is preferred to perform bake, and the temperature of bake is generally from 30 to 300° C. The time from exposure to bake process is preferably shorter from the viewpoint of PED.

The exposure rays here are far ultraviolet rays of wavelengths of preferably 250 nm or less, and more preferably 220 nm or less. Specifically, a KrF excimer laser (248 nm), an ArF excimer laser (193 nm), an $F_2$ excimer laser (157 nm), and X-rays are exemplified.

Incidentally, the variation of performances of a resist at the time when subjected to immersion exposure is thought to be resulting from the contact of a resist surface with an immersion liquid.

An immersion liquid for use in immersion exposure is described below.

An immersion liquid for use in immersion exposure preferably has a temperature coefficient of refractive index as small as possible so as to be transparent to the exposure wavelength and to hold the distortion of an optical image reflected on the resist at the minimum. In particular, when the exposure light source is an ArF excimer laser (wavelength: 193 nm), it is preferred to use water as the immersion liquid for easiness of availability and capable of handling easily, in addition to the above points.

It is also possible to use a medium having a refractive index of 1.5 or more for capable of improving the refractive index. The medium may be an aqueous solution or an organic solvent.

When water is used as the immersion liquid, to reduce the surface tension of water and to increase the surface activity, a trace amount of additive (a liquid) that does not dissolve the resist layer on a wafer and has a negligible influence on the optical coating of the underside of a lens element may be added. As such additives, aliphatic alcohols having a refractive index almost equal to the refractive index of water are preferred, specifically methyl alcohol, ethyl alcohol and isopropyl alcohol are exemplified. By adding an alcohol having a refractive index almost equal to that of water, even if the alcohol component in water is evaporated and the concentration of the content is changed, the refractive index variation of the liquid as a whole can be made extremely small. On the other hand, when impurities opaque to the light of 193 nm or substances largely different from water in a refractive index are mixed, these substances bring about the distortion of an optical image reflected on the resist. Accordingly the water to be used is preferably distilled water. Further, pure water filtered through an ion exchange filter may be used.

The electric resistance of water is preferably 18.3 MΩ·cm or higher, and TOC (total organic material concentration) is preferably 20 ppb or lower, and it is preferred that water has been subjected to deaeration treatment.

It is possible to heighten lithographic performance by increasing the refractive index of an immersion liquid. From such a point of view, additives capable of increasing the refractive index may be added to water, or heavy water ($D_2O$) may be used in place of water.

A film hardly soluble in an immersion liquid (hereinafter also referred to as "topcoat") may be provided between a resist film by the photosensitive composition of the invention and an immersion liquid so as not to bring the resist film into direct contact with the immersion liquid. The necessary functions required of the topcoat are the aptitude for coating on the upper layer of a resist, the transparency to radiation, in particular the transparency to the ray of 193 nm, and the insolubility in an immersion liquid. It is preferred that the topcoat is not mixed with a resist and can be coated uniformly on a resist upper layer.

From the viewpoint of the transparency to 193 nm, a polymer not containing an aromatic group is preferred as the topcoat. Specifically, hydrocarbon polymers, acrylic ester polymers, polymethacrylic acid, polyacrylic acid, polyvinyl ether, silicon-containing polymers, and fluorine-containing polymers are exemplified.

To peel off the topcoat, a developing solution may be used, or a remover may be used separately. As the remover, a solvent low in penetration into a resist is preferred. In view of capable of performing a peeling process at the same time with the development process of a resist, it is preferred that the topcoat can be peeled off by an alkali developing solution. From the viewpoint of performing peeling by an alkali developing solution, the topcoat is preferably acidic, but from the viewpoint of non-intermixture with the resist, the topcoat may be neutral or alkaline.

Resolution increases when there is no difference in the refractive indexes between the topcoat and the immersion liquid. In the case where the exposure light source is an ArF excimer laser (wavelength: 193 nm), it is preferred to use water as the immersion liquid. Accordingly, the refractive index of the topcoat for ArF immersion exposure is nearer the refractive index of water (1.44). Further, from the viewpoint of the transparency and refractive index, the thickness of the topcoat is preferably thinner.

When an organic solvent is used as the immersion liquid, the topcoat is preferably water-soluble.

In a development process, an alkali developing solution is used as follows. As the alkali developing solution of a resist composition, alkaline aqueous solutions of inorganic alkalis, e.g., sodium hydroxide, potassium hydroxide, sodium carbonate, sodium silicate, sodium metasilicate, aqueous ammonia, etc., primary amines, e.g., ethylamine, n-propylamine, etc., secondary amines, e.g., diethylamine, di-n-butylamine, etc., tertiary amines, e.g., triethylamine, methyldiethylamine, etc., alcohol amines, e.g., dimethylethanolamine, triethanolamine, etc., quaternary ammonium salts, e.g., tetramethylammonium hydroxide, tetraethylammonium hydroxide, etc., and cyclic amines, e.g., pyrrole, piperidine, etc., can be used.

An appropriate amount of alcohols and surfactants may be added to the above alkali developing solutions.

The alkali concentration of an alkali developing solution is generally from 0.1 to 20 mass %.

The pH of an alkali developing solution is generally from 10.0 to 15.0.

EXAMPLE

The invention will be described in further detail with reference to examples, but the invention is not restricted thereto. Compound (A1):

(1) Synthesis of Dibenzothiophene-S-oxide

Dibenzothiophene (20.0 g) is suspended in 80.0 ml of trifluoroacetic acid at room temperature. To the suspension is slowly dropped 12.4 ml of 30% aqueous hydrogen peroxide while cooling with ice so as to maintain the reaction temperature around 60° C. After completion of dropping, the reaction solution is stirred at room temperature for 30 minutes. After the reaction, the reaction solution is added to 1,000 ml of water to precipitate crystals. The crystals are recovered by filtration and washed with water. The obtained crystals are recrystallized with acetonitrile to obtain 19.2 g of dibenzothiophene-S-oxide.

$^1$H-NMR (400 MHz, $CDCl_3$) δ 7.51 (t, 2H), 7.59 (t, 2H), 7.81 (d, 2H), 8.00 (d, 2H)

(2) Synthesis of
5-[4-(2-hydroxyethyl)phenyl]dibenzothiophenium
2,4,6-triisopropylbenzenesulfonate (A1)

While cooling with ice, 10.0 g of dibenzothiophene-S-oxide synthesized in the above step (1) is added to 30 g of diphosphorus pentoxide/methanesulfonic acid (9/1), and further 10 ml of 2-phenylethyl acetate is added thereto. The reaction solution is stirred at room temperature for 6 hours, and then poured into ice water. The obtained aqueous solution is filtered, and 23 g of potassium iodide is added. Crystals precipitated are recovered by filtration to obtain 11.1 g of 5-[4-(2-acetoxyethyl)phenyl]dibenzothiophenium iodide. The obtained 11.1 g of 5-[4-(2-acetoxyethyl)phenyl]dibenzothiophenium iodide is dissolved in 200 ml of methanol, and 10.7 g of a 20% aqueous solution of tetramethylammonium hydroxide is added to the solution. After stirring the solution at room temperature for 2 hours, 9.6 g of triisopropylbenzenesulfonic acid is aded and the reaction solution is further stirred at room temperature for 30 minutes. Silver acetate (3.9 g) is added to the reaction solution and stirred at room temperature for 1 hour. After filtering the reaction solution, the mother liquor is distilled under reduced pressure. The crystals obtained are dissolved in chloroform, and washed with water three times. After distilling off chloroform under reduced pressure, the reaction product is recrystallized with ethyl acetate/acetonitrile (5/1), whereby 7.0 g of 5-[4-(2-hydroxyethyl)phenyl]dibenzothiophenium 2,4,6-triisopropylbenzene-sulfonate is obtained.

$^1$H-NMR (400 MHz, CDCl$_3$) δ 1.20 (d, 18H), 2.78 (m, 3H), 3.71 (t, 2H), 4.68 (m, 2H), 7.02 (s, 2H), 7.29 (d, 2H), 7.51 (t, 2H), 7.64 (d, 2H), 7.76 (t, 2H), 8.14 (d, 2H), 8.22 (d, 2H)

(3) Synthesis of
5-[4-(2-hydroxyethyl)phenyl]dibenzo-thiophenium nonafluorobutanesulfonate (A2)

While cooling with ice, 10.0 g of dibenzothiophene-S-oxide synthesized in the above step (1) is stirred in 10 ml of 2-phenylethyl acetate, and 5.7 ml of trifluoroacetic anhydride is added thereto. The reaction solution is stirred at room temperature for 1 hour. After the reaction, 20 ml of diisopropyl ether is added thereto to precipitate crystals, and the crystals are recovered by filtration. The crystals obtained (9.3 g) are dissolved in 200 ml of methanol, and 10.7 g of a 20% aqueous solution of tetramethylammonium hydroxide is added to the solution. The solution is stirred at room temperature for 2 hours. After the reaction, the methanol is distilled off under reduced pressure, and the crystals obtained are dissolved in chloroform, and washed with water three times. After distilling off a chloroform layer under reduced pressure, the reaction product is recrystallized with ethyl acetate/acetonitrile (5/1), whereby 8.5 g of 5-[4-(2-hydroxyethyl)-phenyl] dibenzothiophenium nonafluorobutanesulfonate is obtained.

$^1$H-NMR (400 MHz, CDCl$_3$) δ 2.80 (t, 2H), 3.73 (t, 2H), 7.29 (d, 2H), 7.53 (t, 2H), 7.60 (d, 2H), 7.80 (t, 2H), 8.16 (d, 2H), 8.25 (d, 2H)

Resin (B):

The structure, molecular weight and degree of molecular weight dispersion of each resin (B) used in Examples are shown below. The number on the right hand of each repeating unit is a molar ratio, and the rest is the same as above.

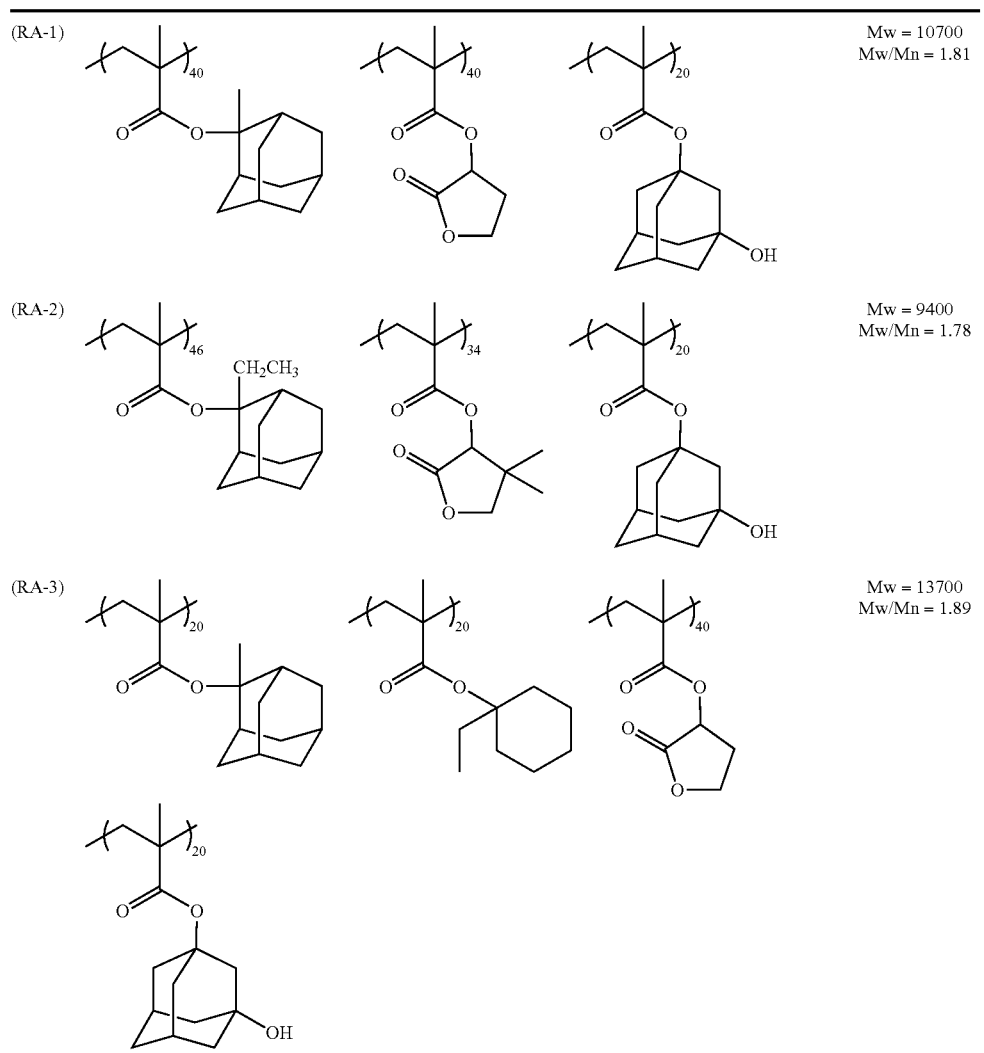

(RA-4) 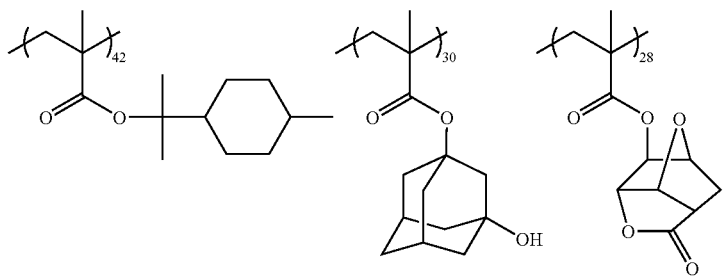
Mw = 10300
Mw/Mn = 1.90
(RA-5) 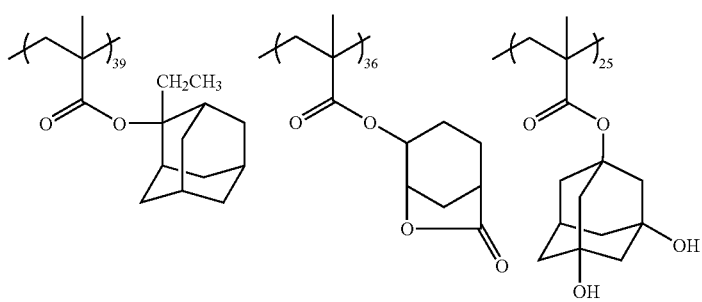
Mw = 8900
Mw/Mn = 1.80
(RA-6) 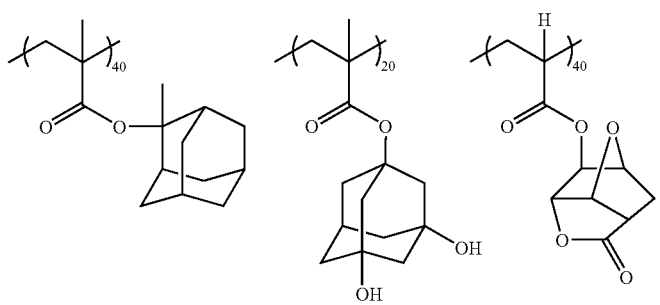
Mw = 7900
Mw/Mn = 1.73
(RA-7) 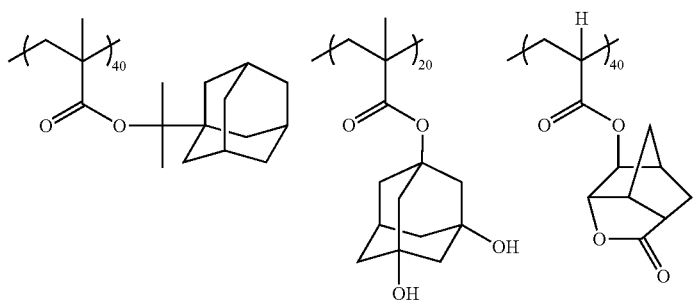
Mw = 8300
Mw/Mn = 1.81

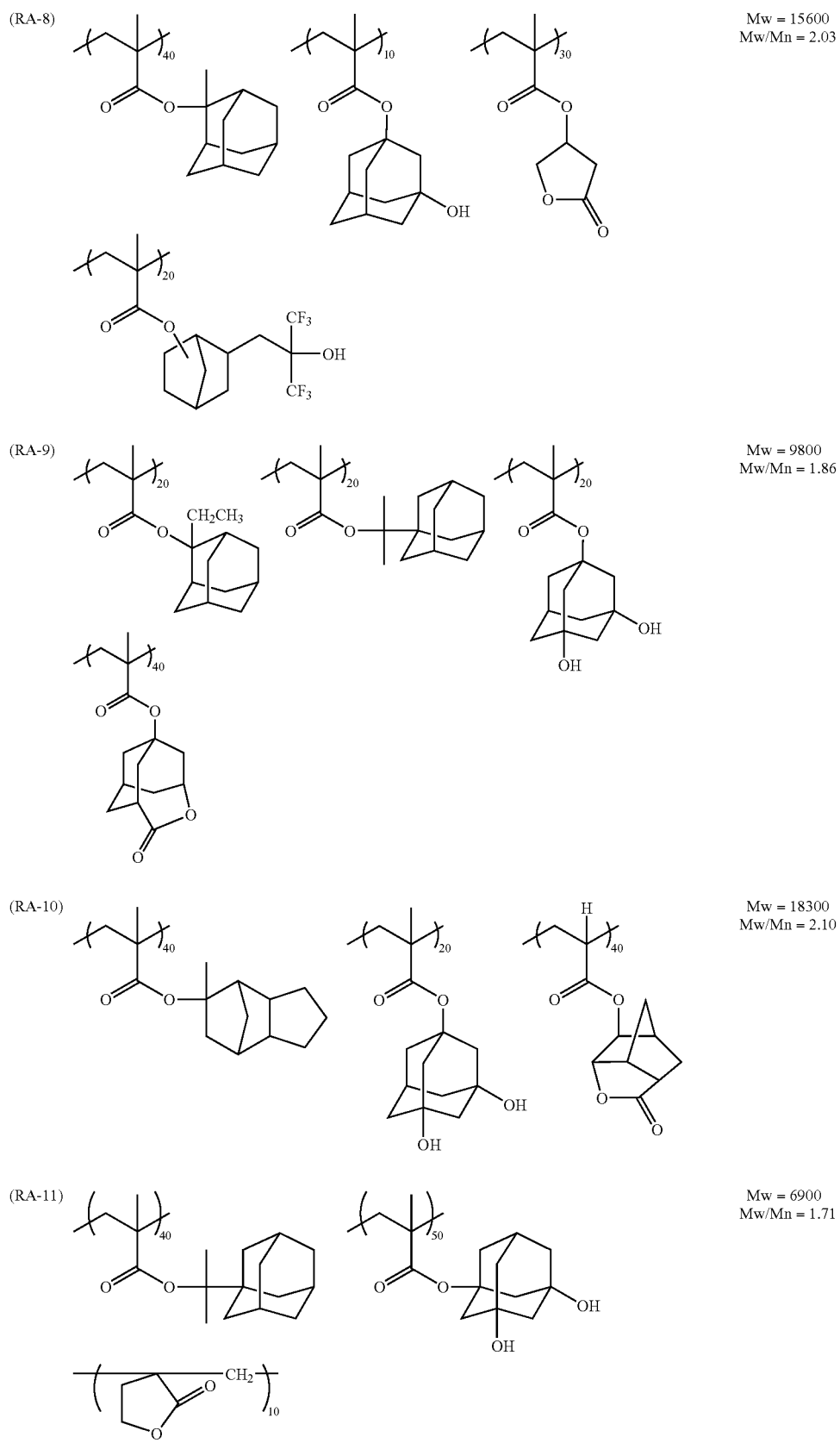

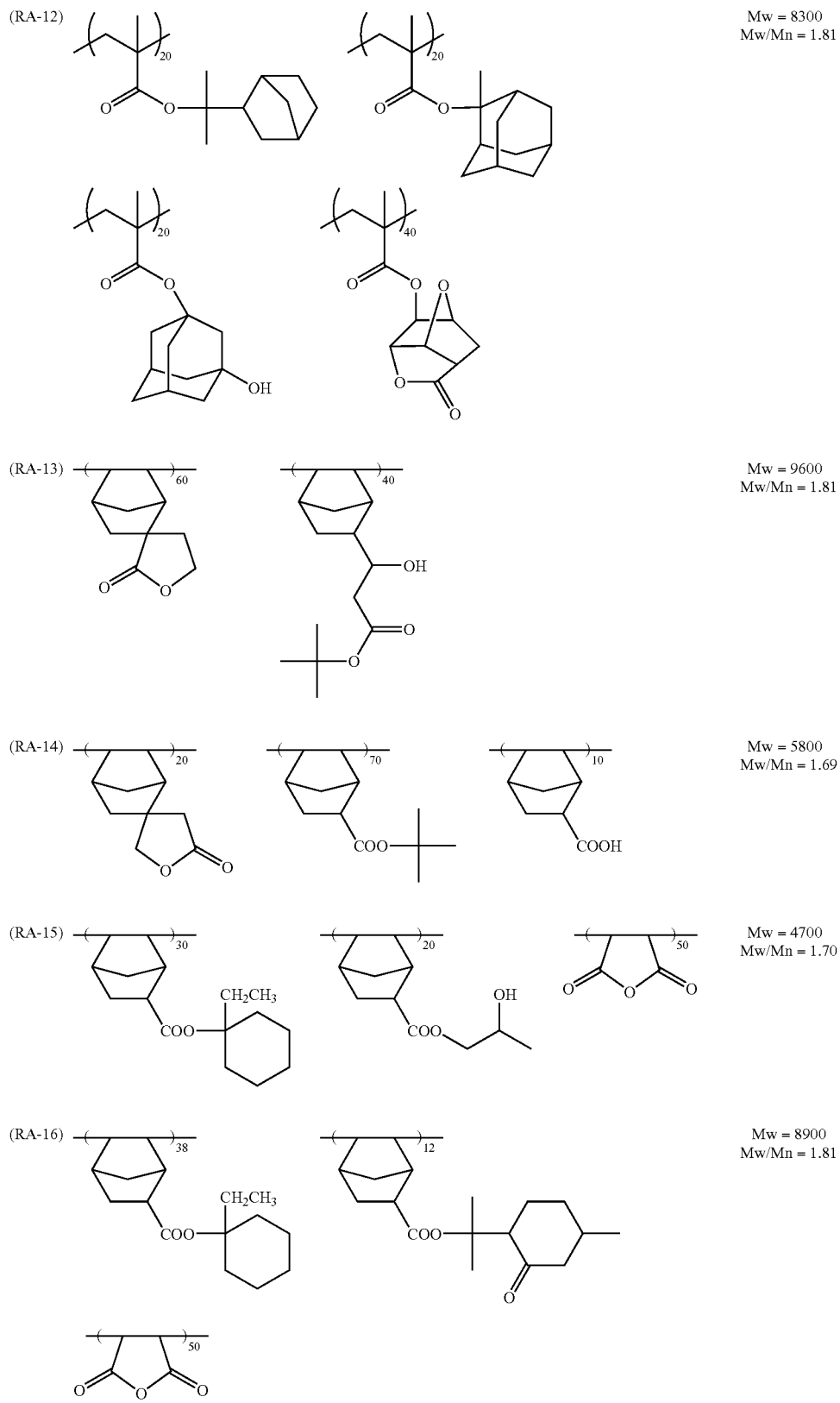

-continued
(RA-17) 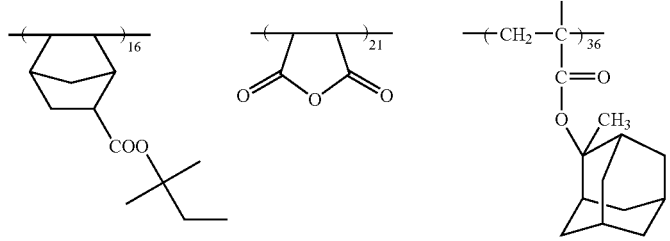 Mw = 13900
Mw/Mn = 1.98
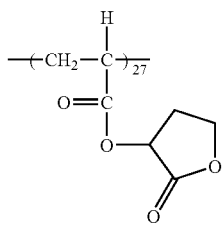
(RA-18) 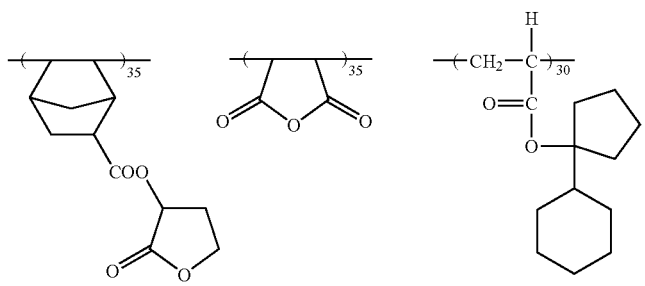 Mw = 12700
Mw/Mn = 1.99
(RA-19) 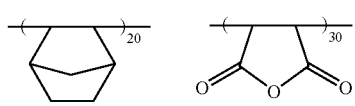 Mw = 9300
Mw/Mn = 1.81
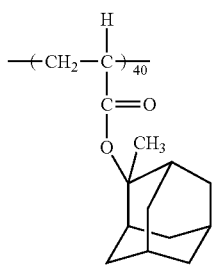
(RA-20) 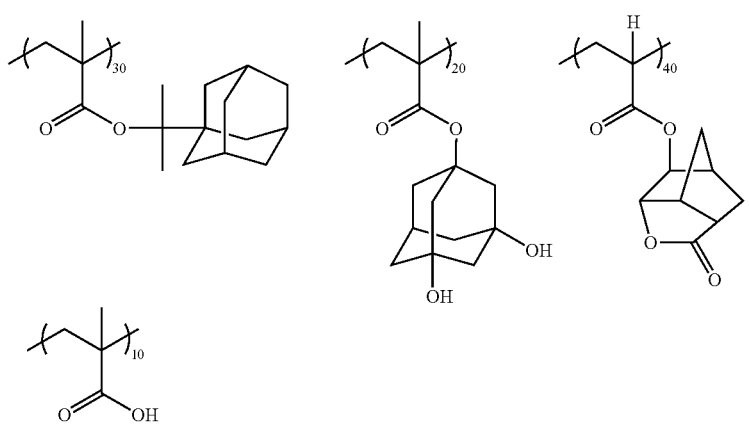 Mw = 7600
Mw/Mn = 1.76

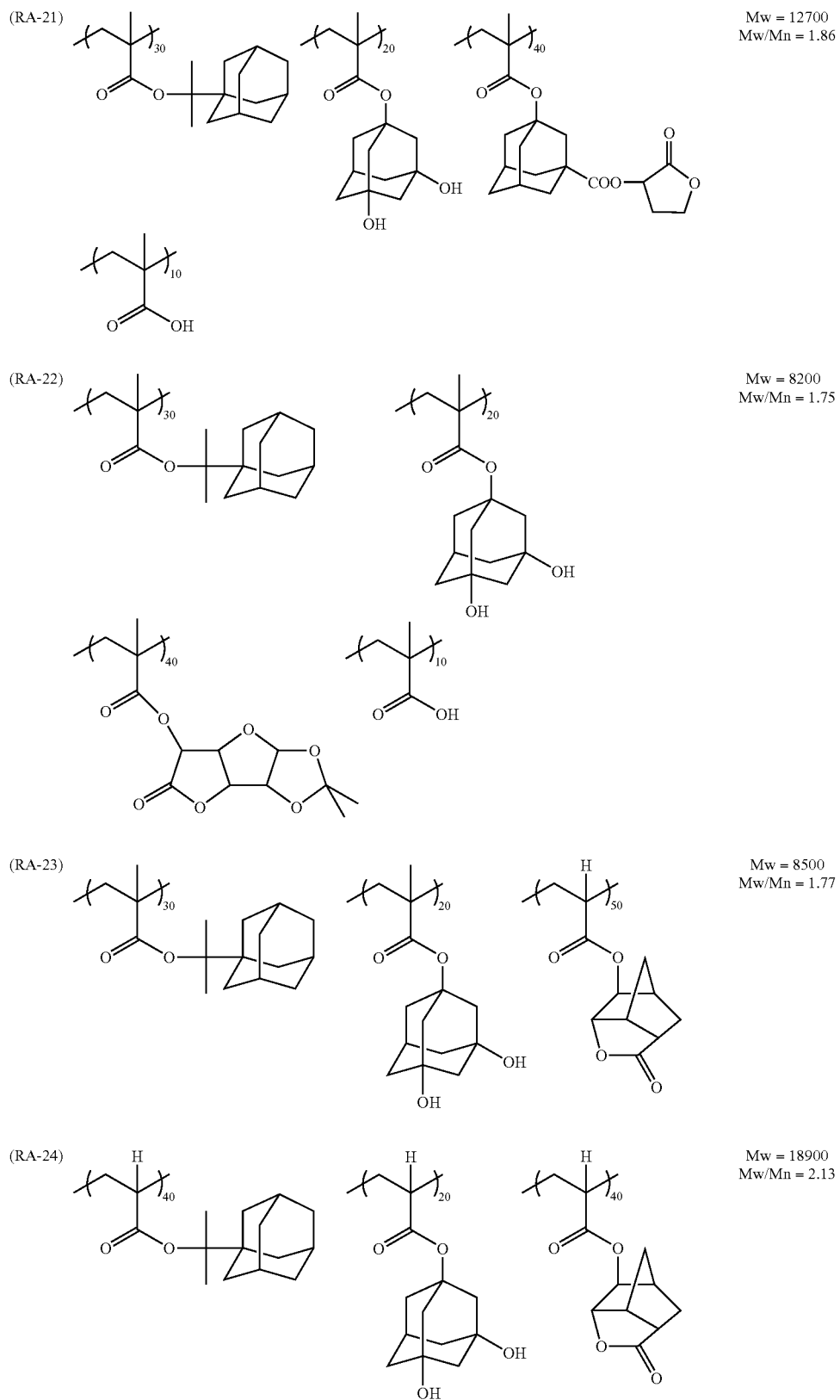

(RA-25) 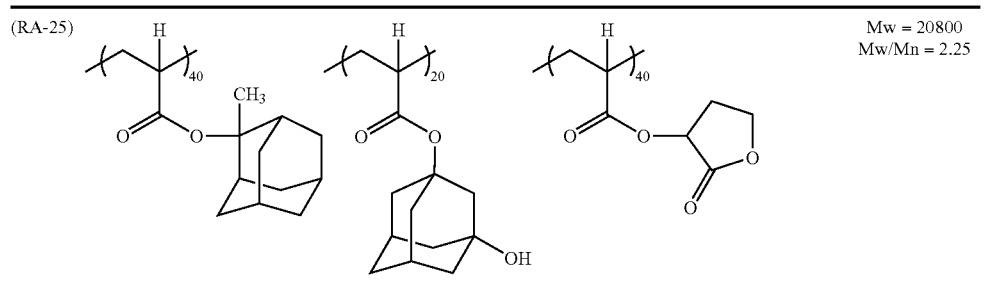

Examples 1 to 8 and Comparative Example 1

Preparation of resist:

A solution having the concentration of solids content of 12 mass % was prepared by dissolving the components in the solvents respectively shown in Table 1, and a positive resist solution was prepared by filtrating the above-prepared solution through a polytetrafluoroethylene filter or a polyethylene filter having a pore size of 0.1 μm. The thus prepared positive resist solution was evaluated as follows. The results obtained are shown in Table 1.

Evaluation of Resist:

An antireflection film DUV-42 (manufactured by Brewer Science) was uniformly coated on a silicon substrate having been subjected to hexamethyldisilazane treatment in a thickness of 600 Å by a spin coater, and dried on a hot plate at 100° C. for 90 seconds, and then dried by heating at 190° C. for 240 seconds. After that, each positive resist solution was coated thereon by a spin coater and dried at 120° C. for 90 seconds to form a resist film having a thickness of 0.25 μm.

The resist film was subjected to exposure through a mask with an ArF excimer laser stepper (NA: 0.6, manufactured by ISI Co.), and heated on a hot plate at 120° C. for 90 seconds just after exposure. Further, the resist film was developed with a 2.38 mass % tetramethylammonium hydroxide aqueous solution at 23° C. for 60 seconds, rinsed with pure water for 30 seconds, and then dried, whereby a line pattern was formed.

Sensitivity and Resolution (γ Value):

The resist film was subjected to a real exposure with varying the exposure amount 0.5 by 0.5 mJ within the range of exposure amount of from 10 to 40 mJ/cm$^2$, and further baking at 110° C. for 90 seconds. After that, a dissolving rate of the resist film at each exposure amount was measured with a 2.38 mass % tetramethylammonium hydroxide (TMAH) aqueous solution, and a sensitivity curve was obtained.

In the sensitivity curve, the exposure amount at the time when the dissolving rate of the resist was saturated was taken as sensitivity, and dissolving contrast (γ value) was computed from the gradient of the straight line part of the sensitivity curve. The greater the γ value, the better is the dissolving contrast.

Line Edge Roughness:

In regard to 50 μm in the machine direction of the line pattern of 150 nm in the irradiation amount showing the above sensitivity, the distance from the intrinsic base line of the edge was measured at arbitrary 30 points with a scanning electron microscope (S-9220, manufactured by Hitachi, Ltd.), and the standard deviation was found, from which 3 σ was computed.

Pattern Profile:

Taking the exposure amount required to reproduce the mask pattern of line and space of line width of 150 nm as the optimal exposure amount, a pattern profile at the optimal exposure amount was observed with a scanning electron microscope (SEM).

TABLE 1

| | ArF Positive Exposure | | | | | | | | | |
|---|---|---|---|---|---|---|---|---|---|---|
| | Composition | | | | | | Evaluation | | | |
| | Acid Generator | | | | | | | | Line Edge | |
| Example No. | Acid Generator (g) | Used in Combination (g) | Resin (10 g) | Basic Compound (g) | Surfactant | Solvent (mass ratio) | Sensitivity (mJ/cm$^2$) | γ Value | Roughness (nm) | Pattern Profile |
| Example 1 | A2 (0.3) | — | RA-20 | C-1 (0.02) | W-1 | A1/B1 (60/40) | 23.6 | 6.2 | 4.3 | Rectangle |
| Example 2 | A9 (0.3) | — | RA-23 | C-3 (0.03) | W-2 | A2/B2 (60/40) | 25.6 | 6.3 | 4.2 | Rectangle |
| Example 3 | A12 (0.4) | z42 (0.1) | RA-9 | C-4 (0.03) | W-1 | A3/B1 (80/20) | 26.9 | 6.1 | 4.6 | Rectangle |
| Example 4 | A16 (0.2) | — | RA-24 | C-6 (0.02) | W-3 | A4/B1 (50/50) | 21.5 | 6.3 | 4.0 | Rectangle |
| Example 5 | A23 (0.4) | z26 (0.1) | RA-25 | C-7 (0.02) | W-1 | A1/B1 (60/40) | 25.5 | 5.5 | 5.3 | Rectangle |
| Example 6 | A28 (0.3) | z13 (0.2) | RA-8 | C-2 (0.04) | W-3 | A2/B2 (60/40) | 22.2 | 5.3 | 5.6 | Rectangle |
| Example 7 | A32 (0.3) | z5 (0.1) | RA-2 | C-3 (0.02) | W-1 | A1/B1 (60/40) | 26.6 | 5.6 | 5.8 | Rectangle |
| Example 8 | A35 (0.3) | z32 (0.1) | RA-23 | C-1 (0.03) | W-4 | A1/B2 (70/30) | 24.3 | 5.4 | 5.5 | Rectangle |
| Comparative Example 1 | A'-1 (0.3) | — | RA-20 | C-1 (0.02) | W-1 | A1/B1 (60/40) | 31.0 | 3.3 | 8.5 | Taper |

The abbreviations of the components are as follows.
Acid Generators:
  Acid generators are as shown above.
  Acid generator (A'-1) used in Comparative Example is a compound shown below.

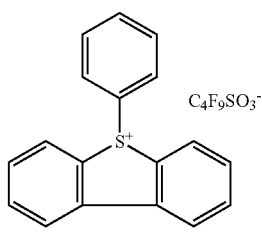

(A'-1)

Basic compounds:
C-1: 2,4,5-Triphenylimidazole
C-2: Triphenylsulfonium acetate
C-3: N-Hydroxyethylpiperidine
C-4: 2,6-Diisopropylaniline
C-5: Dicyclohexylmethylamine
C-6: Tripentylamine
C-7: Hydroxyantipyrine
C-8: Tetrabutylammonium hydroxide
C-9: Tris(methoxyethoxyethyl)amine
C-10: N-Phenyldiethanolamine
C-11: Trioctylamine
C-12: 1,5-Diazabicyclo[4.3.0]nona-5-ene
Surfactants:
W-1: Megafac F176 (fluorine surfactant, manufactured by Dainippon Ink and Chemicals Inc.)
W-2: Megafac R08 (fluorine/silicon surfactant, manufactured by Dainippon Ink and Chemicals Inc.)
W-3: Polysiloxane polymer KP-341 (silicon surfactant, manufactured by Shin-Etsu Chemical Co., Ltd.)
W-4: Troy Sol S-366 (manufactured by Troy Chemical Co., Ltd.)
Solvents:
A1: Propylene glycol monomethyl ether acetate
A2: 2-Heptanone
A3: Cyclohexanone
A4: γ-Butyrolactone
B1: Propylene glycol monomethyl ether
B2: Ethyl lactate From the results shown in Table 1, it is apparent that the photosensitive compositions in the invention are excellent in sensitivity, γ value and pattern profile in ArF exposure.
Evaluation of Immersion Exposure:
Preparation of Resist:
  A solution having the concentration of solids content of 8 mass % was prepared by dissolving each of the components in Examples 1 to 8 in the solvents respectively shown in Table 1, and a positive resist solution was prepared by filtrating the above-prepared solution through a polyethylene filter having a pore size of 0.1 μm. The positive resist solution prepared was evaluated according to the following method.
Evaluation of Resolution:
  An organic antireflection film ARC29A (manufactured by Nissan Chemical Industries, Ltd.) was coated on a silicon wafer, and the coating was baked at 205° C. for 60 seconds to thereby form an antireflection film having a thickness of 78 nm. The above-prepared positive resist solution was coated on the antireflection film and baked at 120° C. for 60 seconds, whereby a resist film having a thickness of 150 nm was formed. The obtained wafer was subjected to two-beam interference exposure with pure water as the immersion liquid (wet exposure). In the two-beam interference exposure (wet exposure), as shown in FIG. 1, wafer 10 having the antireflection film and the resist film was exposed via prism 8 and immersion liquid 9 (pure water) with laser 1, diaphragm 2, shutter 3, three reflection mirrors 4, 5 and 6, and condenser lens 7. The wavelength of laser 1 was 193 nm, and prism 8 was used for forming line and space pattern of 65 nm. Immediately after exposure, the wafer was baked at 120° C. for 60 seconds, and then developed with a 2.38 mass % of tetramethylammonium hydroxide aqueous solution for 60 seconds, rinsed with pure water, and dried with spinning to obtain a resist pattern. It was confirmed that line and space of 65 nm was resolved from the observation of the obtained resist pattern with a scanning electron microscope S-9260 (manufactured by Hitachi, Ltd.).

The compositions in Examples 1 to 8 showed good image forming performance even in the exposure method via an immersion liquid.

Examples 9 to 14 and Comparative Example 2

(1) Formation of Lower Resist Layer
  FHi-028DD resist (resist for i-ray, manufactured by Fuji Film Olin Co., Ltd.) was coated on a 6 inch silicon wafer with a spin coater Mark 8 (manufactured by Tokyo Electron Limited), baked at 90° C. for 90 seconds, whereby a uniform film having a thickness of 0.55 μm was obtained.
  The obtained film was further baked at 200° C. for 3 minutes to thereby form a lower resist layer having a thickness of 0.40 μm.
(2) Formation of Upper Resist Layer
  A solution having the concentration of solids content of 11 mass % was prepared by dissolving the components in the solvents respectively shown in Table 2 below. The solution was filtrated through a membrane filter having a pore diameter of 0.1 μm, whereby a composition for an upper resist layer was prepared.
  The upper resist layer composition was coated on the lower resist layer in the same manner as in the lower layer, and heated at 130° C. for 90 seconds, whereby an upper resist layer having a thickness of 0.20 μm was formed.
  Resins (SI-1) to (SI-5) in Table 2 are as follows.

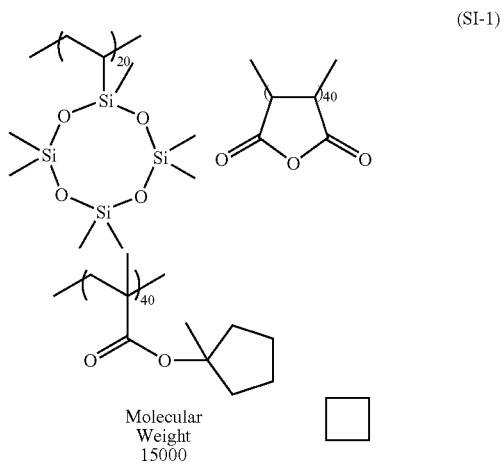

(SI-1)

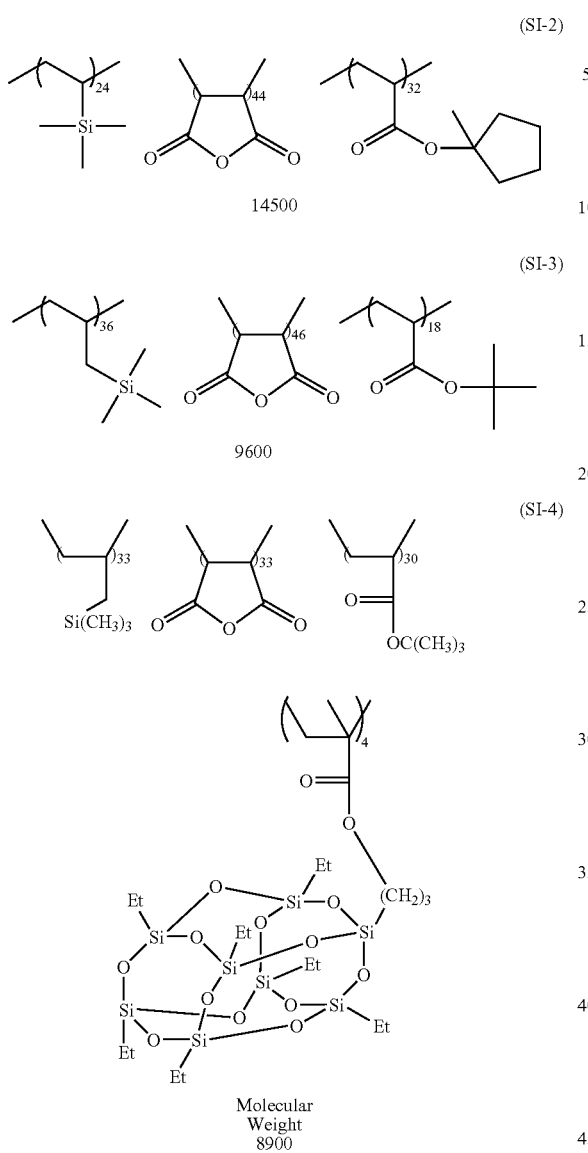

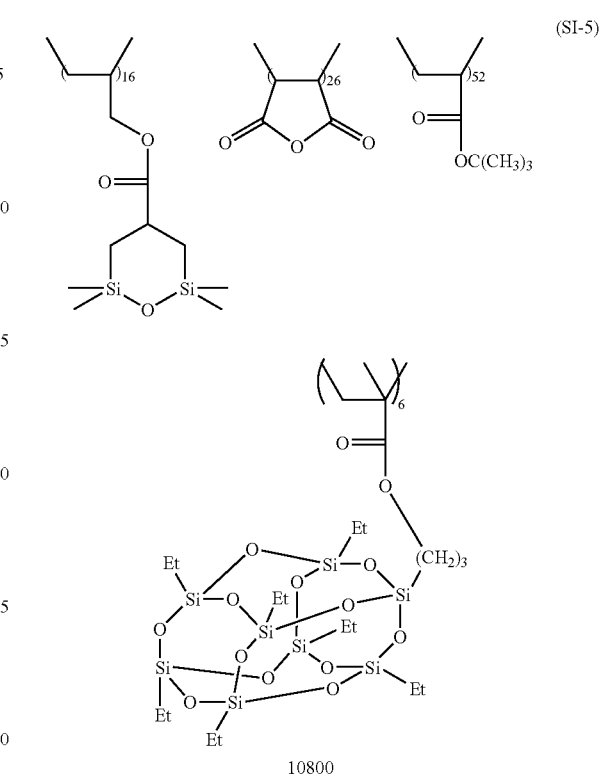

(3) Evaluation of Resist

The thus-obtained wafer was subjected to exposure with ArF Excimer Stepper 9300 (manufactured by ISI Co.) attached with a resolution mask with varying the exposure amount.

Subsequently, after heating at 120° C. for 90 seconds, the wafer was developed with a 2.38 mass % tetrahydroammonium hydroxide developing solution for 60 seconds, rinsed with distilled water and dried to form an upper layer pattern. The resist was evaluated in the same manner as in Example 1 (ArF positive exposure).

The results obtained are shown in Table 2.

TABLE 2

Positive Exposure Containing Silicon

| | Composition | | | | | | Evaluation | | | |
|---|---|---|---|---|---|---|---|---|---|---|
| | Acid Generator | | | | | | | | | |
| Example No. | Acid Generator (g) | Used in Combination (g) | Resin (10 g) | Basic Compound (g) | Surfactant | Solvent (mass ratio) | Sensitivity (mJ/cm$^2$) | γ Value | Line Edge Roughness (nm) | Pattern Profile |
| Example 9 | A2 (0.3) | — | SI-1 | C-1 (0.02) | W-1 | A1/A3 (60/40) | 24.5 | 5.2 | 5.3 | Rectangle |
| Example 10 | A9 (0.2) | z12 (0.1) | SI-1 | C-4 (0.03) | W-1 | A2/A3 (70/30) | 26.3 | 5.5 | 5.4 | Rectangle |
| Example 11 | A12 (0.3) | z25 (0.1) | SI-2 | C-7 (0.03) | W-2 | A1/A2 (60/40) | 25.9 | 5.1 | 6.0 | Rectangle |
| Example 12 | A16 (0.4) | z46 (0.1) | SI-3 | C-9 (0.02) | W-3 | A1/A4 (80/20) | 22.5 | 5.5 | 5.2 | Rectangle |
| Example 13 | A23 (0.3) | z39 (0.2) | SI-4 | C-11 (0.02) | W-2 | A2/A4 (60/40) | 25.6 | 5.1 | 6.2 | Rectangle |
| Example 14 | A28 (0.3) | z46 (0.1) | SI-5 | C-12 (0.04) | W-1 | A2/A3 (70/30) | 23.3 | 5.0 | 6.3 | Rectangle |
| Compartive Example 2 | A'-1 (0.3) | — | SI-1 | C-1 (0.02) | W-1 | A1/A3 (60/40) | 32.5 | 3.4 | 9.5 | Taper |

From the results shown in Table 2, it is apparent that the photosensitive compositions in the invention have also excellent performances when used as two-layered resists.

Examples to 15 to 20 and Comparative Example 3

Preparation of Resist:

A positive resist solution having the concentration of solids content of 14 mass % was prepared by dissolving the components in the solvents respectively shown in Table 3 below, and filtrating the solution through a polytetrafluoroethylene filter having a pore size of 0.1 µm.

was measured at arbitrary 30 points with a scanning electron microscope (S-9220, manufactured by Hitachi, Ltd.), and the standard deviation was found, from which 3 σ was computed.

Pattern Profile:

Taking the exposure amount required to reproduce the mask pattern of line and space of line width of 180 nm as the optimal exposure amount, a pattern profile at the optimal exposure amount was observed with a scanning electron microscope (SEM).

The results obtained are shown in Table 3 below.

TABLE 3

| | Composition | | | | | | Evaluation | | | |
|---|---|---|---|---|---|---|---|---|---|---|
| | Acid Generator | | | | | | | | | |
| Example No. | Acid Generator (g) | Used in Combination (g) | Resin (10 g) | Basic Compound (g) | Surfactant | Solvent (mass ratio) | Sensitivity (mJ/cm$^2$) | γ Value | Line Edge Roughness (nm) | Pattern Profile |
| Example 15 | A1 (0.3) | — | R-2 | C-1 (0.02) | W-1 | A1/B1 (60/40) | 20.0 | 6.1 | 4.5 | Rectangle |
| Example 16 | A4 (0.3) | z5 (0.1) | R-7 | C-3 (0.02) | W-2 | A1/B1 (80/20) | 22.3 | 6.3 | 4.2 | Rectangle |
| Example 17 | A10 (0.2) | z26 (0.1) | R-8 | C-5 (0.03) | W-1 | A2/B2 (70/30) | 19.5 | 6.2 | 4.6 | Rectangle |
| Example 18 | A14 (0.4) | z35 (0.2) | R-9 | C-7 (0.03) | W-3 | A2/B2 (60/40) | 19.8 | 6.2 | 4.5 | Rectangle |
| Example 19 | A18 (0.2) | z42 (0.1) | R-14 | C-10 (0.03) | W-1 | A3/B2 (60/40) | 21.2 | 5.8 | 5.0 | Rectangle |
| Example 20 | A25 (0.2) | z28 (0.2) | R-17 | C-11 (0.03) | W-3 | A4/B1 (60/40) | 23.2 | 5.9 | 5.3 | Rectangle |
| Comparative Example 3 | A'-1 (0.3) | — | R-2 | C-1 (0.02) | W-1 | A1/B1 (70/30) | 27.5 | 3.5 | 7.8 | Taper |

Evaluation of Resist:

The prepared positive resist solution was uniformly coated on a silicone substrate having been subjected to hexamethyldisilazane treatment by a spin coater, and dried by heating on a hot plate at 120° C. for 90 seconds to form a resist film having a thickness of 0.4 µm.

The resist film was subjected to pattern exposure through a mask for line and space with a KrF excimer laser stepper (NA: 0.63), and heated on a hot plate at 110° C. for 90 seconds just after exposure. Further, the resist film was developed with a 2.38 mass % tetramethylammonium hydroxide aqueous solution at 23° C. for 60 seconds, rinsed with pure water for 30 seconds, and then dried, whereby a line pattern was formed.

Sensitivity and Resolution (γ Value):

The resist film was subjected to a real exposure with varying the exposure amount 0.5 by 0.5 mJ within the range of exposure amount of from 10 to 40 mJ/cm$^2$, and further baking at 110° C. for 90 seconds. After that, a dissolving rate of the resist film at each exposure amount was measured with a 2.38 mass % tetramethylammonium hydroxide (TMAH) aqueous solution, and a sensitivity curve was obtained.

In the sensitivity curve, the exposure amount at the time when the dissolving rate of the resist was saturated was taken as sensitivity, and dissolving contrast (γ value) was computed from the gradient of the straight line part of the sensitivity curve. The greater the γ value, the better is the dissolving contrast.

Line Edge Roughness:

In regard to 50 µm in the machine direction of the line pattern of 180 nm in the irradiation amount showing the above sensitivity, the distance from the intrinsic base line of the edge Resins (R-2), (R-7), (R-8), (R-9), (R-14) and (R-17) shown in Table 3 are the resins exemplified above. The molar ratio of repeating units and weight average molecular weight of each resin are shown in Table 4 below.

TABLE 4

| Resin | Molar Ratio of Repeating Units (correspondent from the left hand in order) | Weight Average Molecular Weight |
|---|---|---|
| R-2 | 60/20/20 | 12,000 |
| R-7 | 60/30/10 | 18,000 |
| R-8 | 60/20/20 | 12,000 |
| R-9 | 60/40 | 13,000 |
| R-14 | 60/15/25 | 12,000 |
| R-17 | 80/20 | 15,000 |

From the results shown in Table 3, it is apparent that the photosensitive compositions in the invention have also excellent performances as the positive resist compositions in KrF excimer laser exposure.

Examples 12 to 26 and Comparative Example 4

Preparation of Resist:

A negative resist solution having the concentration of solids content of 14 mass % was prepared by dissolving the components in the solvents respectively shown in Table 5 below, and filtrating the solution through a polytetrafluoroethylene filter having a pore size of 0.1 µm.

Each of the prepared negative resist solutions was evaluated in the same manner as in Example 15 (KrF positive exposure), and the results obtained are shown in Table 5.

TABLE 5

| | Composition | | | | | | | Evaluation | | | |
|---|---|---|---|---|---|---|---|---|---|---|---|
| | Acid | | | | | | | | | | |
| Ex. No. | Acid Generator (g) | Generator Used in Combination | Resin (10 g) | Crosslinking Agent (g) | Basic Compound (g) | Sufactant | Solvent (mass ratio) | Sensitivity (mJ/cm$^2$) | γ Value | Line Edge Roughness (nm) | Pattern Profile |
| Ex. 21 | A1 (0.3) | — | P-1 | CL-1 (3.0) | C-1 (0.02) | W-1 | A1/B1 (60/40) | 21.2 | 6.3 | 10.2 | Rectangle |
| Ex. 22 | A4 (0.3) | z4 (0.1) | P-1 | CL-2 (2.5) | C-3 (0.02) | W-2 | A1/B1 (80/20) | 23.5 | 6.5 | 11.2 | Rectangle |
| Ex. 23 | A10 (0.2) | z10 (0.05) | P-2 | CL-3 (2.0) | C-5 (0.03) | W-1 | A2/B2 (70/30) | 20.5 | 6.2 | 10.5 | Rectangle |
| Ex. 24 | A14 (0.4) | z27 (0.2) | P-2 | CL-4 (3.0) | C-7 (0.03) | W-3 | A2/B2 (60/40) | 21.0 | 6.1 | 12.3 | Rectangle |
| Ex. 25 | A18 (0.2) | z31 (0.05) | P-3 | CL-5 (3.0) | C-10 (0.03) | W-1 | A3/B2 (60/40) | 22.1 | 6.2 | 12.0 | Rectangle |
| Ex. 26 | A25 (0.2) | z38 (0.2) | P-3 | CL-6 (2.5) | C-11 (0.03) | W-3 | A4/B1 (60/40) | 22.5 | 6.3 | 11.8 | Rectangle |
| Comp. Ex. 4 | A'-1 (0.3) | — | P-3 | CL-1 (3.0) | C-1 (0.02) | W-1 | A1/B1 (70/30) | 33.3 | 4.2 | 16.3 | Taper |

The structures, molecular weights, and molecular weight distributions of the alkali-soluble resins and crosslinking agents in Table 5 are shown below.

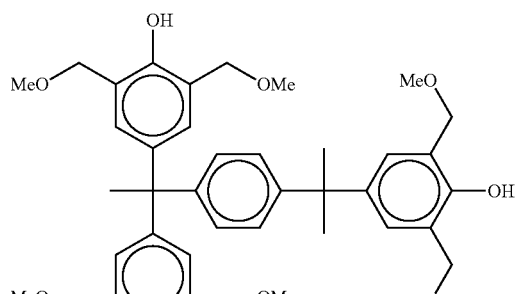

VP-5000 (manufactured by Nippon Soda Co., Ltd.)

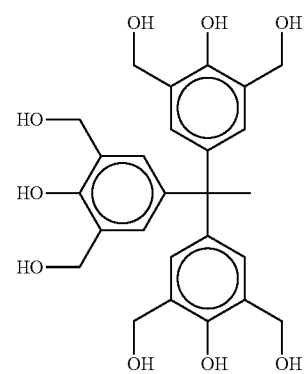

-continued

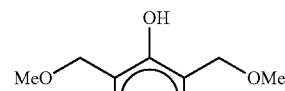

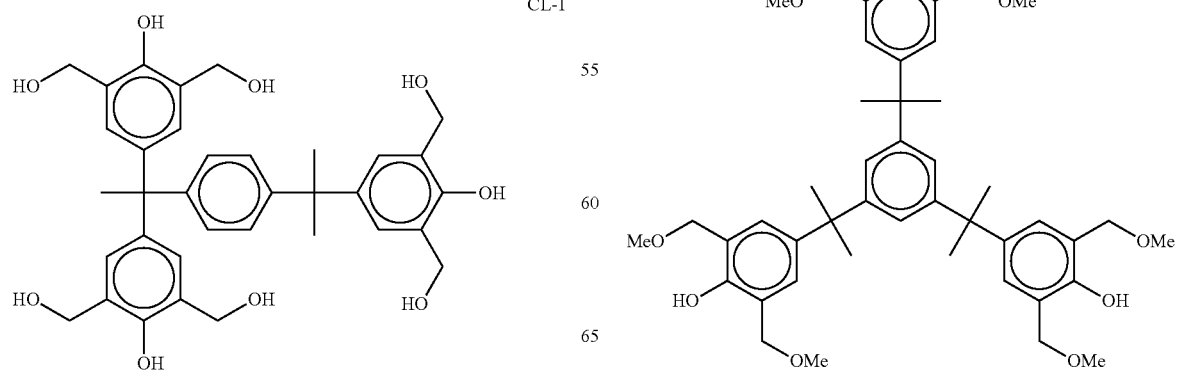

-continued

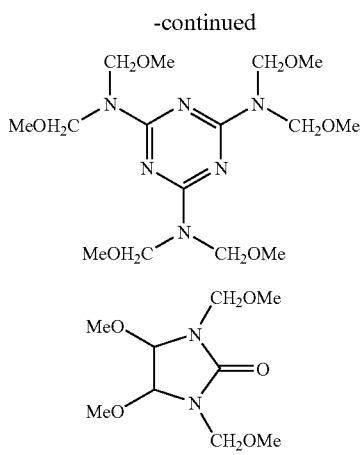

From the results shown in Table 5, it can be seen that the photosensitive compositions in the invention have also excellent performances as the negative resist compositions in KrF excimer laser exposure.

Examples 27 to 32 and Comparative Example 5

Preparation of Resist:

A positive resist solution having the concentration of solids content of 12 mass % was prepared by dissolving the components in the solvents respectively shown in Table 3, and filtrating the solution through a polytetrafluoroethylene filter having a pore size of 0.1 μm.

Evaluation of Resist:

The prepared positive resist solution was uniformly coated on a silicon substrate having been subjected to hexamethyldisilazane treatment by a spin coater, and dried by heating on a hot plate at 120° C. for 60 seconds to form a resist film having a thickness of 0.3 μm.

The resist film was irradiated with an electron beam projection lithographic apparatus (accelerating voltage: 100 keV, manufactured by Nikon Corporation), and heated on a hot plate at 110° C. for 90 seconds just after irradiation. Further, the resist film was developed with a 2.38 mass % tetramethylammonium hydroxide aqueous solution at 23° C. for 60 seconds, rinsed with pure water for 30 seconds, and then dried, whereby a line and space pattern was formed. Performances were evaluated in the same manner as in Example 1.

Sensitivity and Resolution (γ Value):

The resist film was subjected to a real exposure with varying the exposure amount 0.1 by 0.1 μC/cm² within the range of exposure amount of from 0 to 10 μC/cm², and further baking at 110° C. for 90 seconds. After that, a dissolving rate of the resist film at each exposure amount was measured with a 2.38 mass % tetrarnethylammonium hydroxide (TMAH) aqueous solution, and a sensitivity curve was obtained.

In the sensitivity curve, the exposure amount at the time when the dissolving rate of the resist was saturated was taken as sensitivity, and dissolving contrast (γ value) was computed from the gradient of the straight line part of the sensitivity curve.

Line Edge Roughness:

In regard to 50 μm in the machine direction of the line pattern of 150 nm in the irradiation amount showing the above sensitivity, the distance from the intrinsic base line of the edge was measured at arbitrary 30 points with a scanning electron microscope (S-9220, manufactured by Hitachi, Ltd.), and the standard deviation was found, from which 3σ was computed.

Outgassing Characteristics: the Coefficient of Fluctuation in the Film Thickness after Exposure:

The resist film was irradiated with 2.0 times the quantity of irradiation at sensitivity determined by a real exposure with electron beam (μC/cm²), and the thickness of the film after exposure (before post-baking) was measured, and the coefficient of fluctuation from the film thickness at unexposed time was found according to the following equation.

Coefficient of fluctuation in film thickness (%)=[(film thickness at unexposed time−film thickness after exposure)/film thickness at unexposed time]×100

The results of evaluation are shown in Table 6 below.

TABLE 6

| | Electron Beam Positive Exposure | | | |
|---|---|---|---|---|
| | Evaluation | | | |
| Example No. | Sensitivity (μC/cm²) | γ Value | Line Edge Roughness (nm) | Outgassing Characteristics (%) |
| Example 27 | 3.5 | 5.6 | 4.1 | 1.2 |
| Example 28 | 4.1 | 5.4 | 4.4 | 2.2 |
| Example 29 | 3.6 | 5.3 | 4.2 | 2.3 |
| Example 30 | 3.8 | 5.5 | 4.7 | 2.5 |
| Example 31 | 4.1 | 4.9 | 5.1 | 1.9 |
| Example 32 | 4.2 | 5.0 | 5.0 | 1.8 |
| Comparative Example 5 | 7.1 | 3.8 | 7.5 | 6.9 |

From the results shown in Table 6, it can be seen that the photosensitive compositions in the invention also have excellent performances as the positive resist compositions for electron beam irradiation.

Examples to 33 to 38 and Comparative Example 6

Preparation of Resist:

A negative resist solution having the concentration of solids content of 12 mass % was prepared by dissolving the components in the solvents respectively shown in Table 5, and filtrating the solution through a polytetrafluoroethylene filter having a pore size of 0.1 μm.

Evaluation of Resist:

The prepared negative resist solution was uniformly coated on a silicon substrate having been subjected to hexamethyldisilazane treatment by a spin coater, and dried by heating on a hot plate at 120° C. for 60 seconds to form a resist film having a thickness of 0.3 μm.

The resist film was irradiated with an electron beam projection lithographic apparatus (accelerating voltage: 100 keV, manufactured by Nikon Corporation), and heated on a hot plate at 110° C. for 90 seconds just after irradiation. Further, the resist film was developed with a 2.38 mass % tetramethylammonium hydroxide aqueous solution at 23° C. for 60 seconds, rinsed with pure water for 30 seconds, and then dried, whereby a line and space pattern was formed. Performances were evaluated in the same manner as in Example 27 (electron beam positive exposure).

The results obtained are shown in Table 7 below.

TABLE 7

Electron Beam Negative Exposure

| Example No. | Sensitivity (μC/cm²) | γ Value | Line Edge Roughness (nm) | Outgassing Characteristics (%) |
|---|---|---|---|---|
| Example 33 | 3.8 | 6.0 | 9.5 | 1.5 |
| Example 34 | 4.0 | 5.7 | 9.3 | 2.5 |
| Example 35 | 3.4 | 5.8 | 9.0 | 2.4 |
| Example 36 | 4.0 | 5.6 | 10.1 | 2.6 |
| Example 37 | 4.2 | 5.2 | 9.8 | 2.3 |
| Example 38 | 4.3 | 5.3 | 10.3 | 3.0 |
| Comparative Example 6 | 7.0 | 4.1 | 15.8 | 7.2 |

From the results shown in Table 7, it can be seen that the photosensitive compositions in the invention have also excellent performances as the negative resist compositions for electron beam irradiation.

Examples 39 to 44 and Comparative Example 7

A positive resist solution having the concentration of solids content of 8 mass % was prepared by dissolving the components in the solvents respectively shown in Table 3, and filtrating the solution through a polytetrafluoroethylene filter having a pore size of 0.1 μm. Evaluations were performed as follows.

Evaluation of Resist:

The prepared positive resist solution was uniformly coated on a silicon substrate having been subjected to hexamethyldisilazane treatment by a spin coater, and dried by heating on a hot plate at 120° C. for 60 seconds to form a resist film having a thickness of 0.15 μm.

Sensitivity and γ Value:

The obtained resist film was subjected to a real exposure with EUV ray (wavelength: 13 nm) with varying the exposure amount 0.5 by 0.5 mJ within the range of exposure amount of from 0 to 10.0 mJ, and the resist film was further baked at 110° C. for 90 seconds. After that, a dissolving rate of the resist film at each exposure amount was measured with a 2.38 mass % tetramethylammonium hydroxide (TMAH) aqueous solution, and a sensitivity curve was obtained.

In the sensitivity curve, the exposure amount at the time when the dissolving rate of the resist was saturated was taken as sensitivity, and dissolving contrast (γvalue) was computed from the gradient of the straight line part of the sensitivity curve. The greater the γ value, the better is the dissolving contrast.

Outgassing Characteristics: the Coefficient of Fluctuation in the Film Thickness after Exposure:

The resist film was irradiated with 2.0 times the quantity of irradiation at sensitivity determined by a real exposure with EUV (mJ/cm²), and the thickness of the film after exposure (before post-baking) was measured, and the coefficient of fluctuation from the film thickness at unexposed time was found according to the following equation.

Coefficient of fluctuation in film thickness (%)=[(film thickness at unexposed time−film thickness after exposure)/film thickness at unexposed time]×100

The results of evaluation are shown in Table 8 below.

TABLE 8

EUV Positive Exposure

| Example No. | Sensitivity (mJ/cm²) | γ Value | Outgassing Characteristics (%) |
|---|---|---|---|
| Example 39 | 3.5 | 6.3 | 1.6 |
| Example 40 | 3.9 | 6.2 | 2.6 |
| Example 41 | 3.2 | 6.3 | 3.0 |
| Example 42 | 3.7 | 5.9 | 2.4 |
| Example 43 | 4.0 | 6.0 | 2.2 |
| Example 44 | 4.1 | 5.8 | 2.0 |
| Comparative Example 7 | 7.2 | 3.4 | 8.5 |

Examples 45 to 50 and Comparative Example 8

A negative resist solution having the concentration of solids content of 8 mass % was prepared by dissolving the components in the solvents respectively shown in Table 5, and filtrating the solution through a polytetrafluoroethylene filter having a pore size of 0.1 μm. Each of the prepared resists are evaluated as follows.

The prepared negative resist solution was uniformly coated on a silicon substrate having been subjected to hexamethyldisilazane treatment by a spin coater, and dried by heating on a hot plate at 120° C. for 60 seconds to form a resist film having a thickness of 0.15 μm.

Sensitivity and γ Value:

The obtained resist film was subjected to a real exposure with EUV ray (wavelength: 13 nm) with varying exposure amount 0.5 by 0.5 mJ within the range of exposure amount of from 0 to 10.0 mJ, and the resist film was further baked at 110° C. for 90 seconds. After that, a dissolving rate of the resist film at each exposure amount was measured with a 2.38 mass % tetramethylammonium hydroxide (TMAH) aqueous solution, and a sensitivity curve was obtained.

Evaluation was performed in the same manner as in Example 39 (EUV positive exposure). The results obtained are shown in Table 9 below.

TABLE 9

EUV Negative Exposure

| Example No. | Sensitivity (mJ/cm²) | γ Value | Outgassing Characteristics (%) |
|---|---|---|---|
| Example 45 | 3.3 | 5.0 | 1.2 |
| Example 46 | 3.6 | 5.4 | 2.6 |
| Example 47 | 3.0 | 5.6 | 2.1 |
| Example 48 | 3.1 | 4.8 | 1.8 |
| Example 49 | 3.4 | 4.9 | 2.6 |
| Example 50 | 3.8 | 4.8 | 1.5 |
| Comparative Example 8 | 5.6 | 3.0 | 8.2 |

From the results shown in Tables 8 and 9, it can be seen that the resist compositions in the invention are high sensitivity, high contrast and excellent in outgassing characteristics in the characteristic evaluation by irradiation with EUV ray as compared with comparative compositions.

The invention can provide a photosensitive composition excellent in sensitivity, resolution, roughness, and outgassing characteristics, and a pattern-forming method using the photosensitive composition.

The entire disclosure of each and every foreign patent application from which the benefit of foreign priority has been claimed in the present application is incorporated herein by reference, as if fully set forth.

What is claimed is:

1. A photosensitive composition, which comprises (a) a compound represented by formula (I):

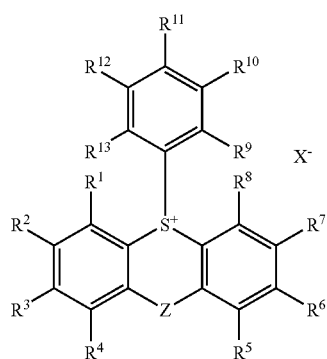

wherein $R^1$ to $R^{13}$ each independently represents a hydrogen atom or a substituent, and at least one of $R^1$ to $R^{13}$ is a substituent containing an alcoholic hydroxyl group, wherein the substituent containing an alcoholic hydroxyl group is represented by —W—Y, wherein Y is an alkyl group substituted with a hydroxyl group, and W is a single bond or a divalent linking group obtained by substituting an arbitrary hydrogen atom of a monovalent group with a single bond, the monovalent group being selected from the group consisting of an acyloxy group, a carbamoyloxy group, an alkoxycarbonyloxy group, an aryloxycarbonyloxy group, an acylamino group, an amino-carbonylamino group, an alkoxycarbonylamino group, an aryloxycarbonylamino group, a sulfamoylamino group, an alkylsulfonylamino group, an arylsulfonylamino group, an arylthio group, a sulfamoyl group, an alkylsulfinyl group, an arylsulfinyl group, an alkylsulfonyl group, an arylsulfonyl group, an acyl group, an aryloxycarbonyl group, an alkoxycarbonyl group, and a carbamoyl group;

Z represents a single bond or a divalent linking group; and X⁻ represents a counter anion, and (b) a resin capable of decomposing by an action of an acid to increase solubility in an alkali developing solution.

2. The photosensitive composition according to claim 1, wherein Y is an alkyl group substituted with a hydroxyl group, and W is a single bond.

3. The photosensitive composition according to claim 1, wherein $R^1$ to $R^{13}$ each independently represents a hydrogen atom or an alkyl group and at least one of $R^1$ to $R^{13}$ is an alkyl group substituted with an alcoholic hydroxyl group.

4. The photosensitive composition according to claim 1, wherein Z represents a single bond, an ether group or a thioether group.

5. The photosensitive composition according to claim 4, wherein Z represents a single bond.

6. The photosensitive composition according to claim 1, wherein the counter anion represented by X⁻ is an organic anion.

7. A pattern-forming method, which comprises:
forming a photosensitive film with the photosensitive composition according to claim 1; and
exposing and developing the photosensitive film.

8. A photosensitive composition, which comprises
(a) a compound represented by formula (I):

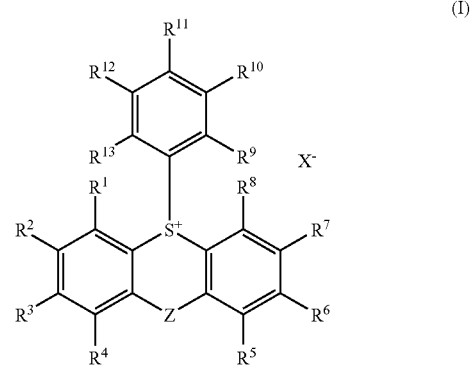

wherein $R^1$ to $R^{13}$ each independently represents a hydrogen atom or a substituent, and at least one of $R^1$ to $R^{13}$ is a substituent containing an alcoholic hydroxyl group, wherein the substituent containing an alcoholic hydroxyl group is represented by —W—Y, wherein Y is an alkyl group substituted with a hydroxyl group, and W is a single bond or a divalent linking group obtained by substituting an arbitrary hydrogen atom of a monovalent group with a single bond, the monovalent group being selected from the group consisting of an acyloxy group, a carbamoyloxy group, an alkoxycarbonyloxy group, an aryloxycarbonyloxy group, an acylamino group, an amino-carbonylamino group, an alkoxycarbonylamino group, an aryloxycarbonylamino group, a sulfamoylamino group, an alkylsulfonylamino group, an arylsulfonylamino group, an arylthio group, a sulfamoyl group, an alkylsulfinyl group, an arylsulfinyl group, an alkylsulfonyl group, an arylsulfonyl group, an acyl group, an aryloxycarbonyl group, an alkoxycarbonyl group, and a carbamoyl group;

Z represents a single bond or a divalent linking group; and X⁻ represents a counter anion, (b) a resin soluble in an alkali developing solution; and
(c) an acid crosslinking agent capable of crosslinking with the resin soluble in an alkali developing solution by an action of an acid.

9. The photosensitive composition according to claim 8, wherein Y is an alkyl group substituted with a hydroxyl group, and W is a single bond.

10. The photosensitive composition according to claim 8, wherein $R^1$ to $R^{13}$ each independently represents a hydrogen atom or an alkyl group and at least one of $R^1$ to $R^{13}$ is an alkyl group substituted with an alcoholic hydroxyl group.

11. The photosensitive composition according to claim 8, wherein Z represents a single bond, an ether group or a thioether group.

12. The photosensitive composition according to claim 11, wherein Z represents a single bond.

13. The photosensitive composition according to claim 8, wherein the counter anion represented by X⁻ is an organic anion.

14. A pattern-forming method, which comprises:
forming a photosensitive film with the photosensitive composition according to claim 8; and
exposing and developing the photosensitive film.

15. A compound represented by formula (I):

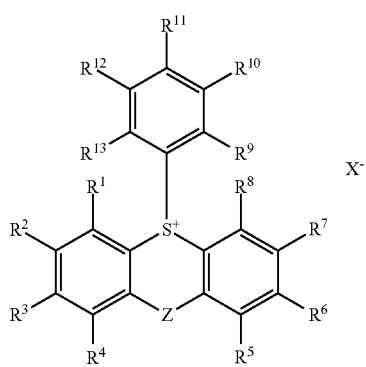

wherein $R^1$ to $R^{13}$ each independently represents a hydrogen atom or a substituent, and at least one of $R^1$ to $R^{13}$ is a substituent containing an alcoholic hydroxyl group, wherein the substituent containing an alcoholic hydroxyl group is represented by —W—Y, wherein Y is an alkyl group substituted with a hydroxyl group, and W is a single bond or a divalent linking group obtained by substituting an arbitrary hydrogen atom of a monovalent group with a single bond, the monovalent group being selected from the group consisting of an acyloxy group, a carbamoyloxy group, an alkoxycarbonyloxy group, an aryloxycarbonyloxy group, an acylamino group, an amino-carbonylamino group, an alkoxycarbonylamino group, an aryloxycarbonylamino group, a sulfamoylamino group, an alkylsulfonylamino group, an arylsulfonylamino group, an arylthio group, a sulfamoyl group, an alkylsulfinyl group, an arylsulfinyl group, an alkylsulfonyl group, an arylsulfonyl group, an acyl group, an aryloxycarbonyl group, an alkoxycarbonyl group, and a carbamoyl group;

Z represents a single bond or a divalent linking group; and $X^-$ represents an organic anion.

16. The compound according to claim 15, wherein Y is an alkyl group substituted with a hydroxyl group, and W is a single bond.

17. The compound according to claim 16, wherein Z is a single bond.

18. The compound according to claim 15, wherein $R^1$ to $R^{13}$ each independently represents a hydrogen atom or an alkyl group and at least one of $R^1$ to $R^{13}$ is an alkyl group substituted with an alcoholic hydroxyl group.

19. The compound according to claim 15, wherein Z represents a single bond, an ether group or a thioether group.

20. The compound according to claim 19, wherein Z represents a single bond.

* * * * *